US011667933B2

(12) United States Patent
Fredens et al.

(10) Patent No.: US 11,667,933 B2
(45) Date of Patent: Jun. 6, 2023

(54) GENOME EDITING

(71) Applicant: United Kingdom Research and Innovation, Swindon (GB)

(72) Inventors: Julius Fredens, Cambridge (GB); Kaihang Wang, Cambridge (GB); Jason W. Chin, Cambridge (GB)

( * ) Notice: Subject to any disclaimer, the term of this patent is extended or adjusted under 35 U.S.C. 154(b) by 1066 days.

(21) Appl. No.: 16/311,265

(22) PCT Filed: Jul. 27, 2017

(86) PCT No.: PCT/GB2017/052188
§ 371 (c)(1),
(2) Date: Dec. 19, 2018

(87) PCT Pub. No.: WO2018/020248
PCT Pub. Date: Feb. 1, 2018

(65) Prior Publication Data
US 2020/0063164 A1    Feb. 27, 2020

(30) Foreign Application Priority Data
Jul. 29, 2016    (GB) .................................... 1613135

(51) Int. Cl.
| | | |
|---|---|---|
| *C12N 15/90* | (2006.01) | |
| *C12N 9/22* | (2006.01) | |
| *C12N 15/10* | (2006.01) | |
| *C12N 15/70* | (2006.01) | |
| *C12N 15/85* | (2006.01) | |
| *C12N 15/66* | (2006.01) | |

(52) U.S. Cl.
CPC ............ *C12N 15/902* (2013.01); *C12N 9/22* (2013.01); *C12N 15/1082* (2013.01); *C12N 15/70* (2013.01); *C12N 15/85* (2013.01); *C12N 15/66* (2013.01)

(58) Field of Classification Search
None
See application file for complete search history.

(56) References Cited

FOREIGN PATENT DOCUMENTS

| WO | 2014/143381 | 9/2014 |
| WO | WO 2018/020248 | 2/2018 |

OTHER PUBLICATIONS

Sopher et al., "Efficient recombination-based methods for bacterial artificial chromosome fusion and mutagenesis" 371 Gene 136-143 (Year: 2006).*
Annaluru, et al., "Total synthesis of a functional designer eukaryotic chromosome." Science (2014); 344(6179): 55-58. Epub Mar. 27, 2014.
Baba, et al., "Construction of *Escherichia coli* K-12 in-frame, single-gene knockout mutants: the Keio collection." Mol Syst Biol (2006); 2:2006.0008. Epub Feb. 21, 2006.
Bryksin and Matsumura, "Rational design of a plasmid origin that replicates efficiently in both gram-positive and gram-negative bacteria." PLoS One (2010); 5(10): e13244.
Carson, et al., "The FtsQ protein of *Escherichia coli*: membrane topology, abundance, and cell division phenotypes due to overproduction and insertion mutations." J Bacteriol (1991); 173(7): 2187-2195.
Cello, et al., "Chemical synthesis of poliovirus cDNA: generation of infectious virus in the absence of natural template." Science (2002); 297(5583): 1016-1018 Epub Jul. 11, 2002.
Chan, et al., "Refactoring bacteriophage T7." Mol Syst Biol (2005); 1:2005.0018. Epub Sep. 13, 2005.
Chin, J.W., "Molecular biology. Reprogramming the genetic code." Science (2012); 336(6080): 428-429.
Cho, et al., "The transcription unit architecture of the *Escherichia coli* genome." Nat Biotechnol (2009); 27(11): 1043-9. Epub Nov. 1, 2009.
Cong, et al., "Multiplex genome engineering using CRISPR/Cas systems." Science (2013); 339(6121): 819-823. Epub Jan. 3, 2013.
Curran, J.F., "Decoding with the A:I wobble pair is inefficient." Nucleic Acids Res (1995); 23(4): 683-688.
Curran and Yarus, "Rates of aminoacyl-tRNA selection at 29 sense codons in vivo." J Mol Biol (1989); 209(1): 65-77.
Dai and Lutkenhaus, "The proper ratio of FtsZ to FtsA is required for cell division to occur in *Escherichia coli*." J Bacteriol (1992); 174(19): 6145-6151.
Datsenko and Wanner, "One-step inactivation of chromosomal genes in *Escherichia coli* K-12 using PCR products." Proc Natl Acad Sci U S A (2000); 97(12): 6640-6645.
Dewar, et al., "Inhibition of cell division initiation by an imbalance in the ratio of FtsA to FtsZ." J Bacteriol (1992); 174(19): 6314-6316.
Dong, et al., "Co-variation of tRNA abundance and codon usage in *Escherichia coli* at different growth rates." J Mol Biol (1996); 260(5): 649-663.
Dos Reis, et al., "Solving the riddle of codon usage preferences: a test for translational selection." Nucleic Acids Res (2004); 32(17): 5036-5044.

(Continued)

*Primary Examiner* — Nancy J Leith
(74) *Attorney, Agent, or Firm* — Clark & Elbing LLP

(57) ABSTRACT

The invention relates to a method comprising a) providing a host cell said host cell comprising an episomal replicon, said episomal replicon comprising a donor nucleic acid sequence, said host cell further comprising a target nucleic acid, b) providing helper protein(s) capable of supporting nucleic acid recombination in said host cell c) providing helper protein(s) and/or RNAs capable of supporting nucleic acid excision in said host cell wherein said donor nucleic acid sequence comprises in order. 5'-homologous recombination sequence 1-sequence of interest-homologous recombination sequence 2-3' wherein said sequence of interest comprises a positive selectable marker d) inducing excision of said donor nucleic acid sequence e) incubating to allow recombination between the excised donor nucleic acid and said target nucleic acid f) selecting for recombinants having incorporated said donor nucleic acid into said target nucleic acid. Also described are nucleic acids and cells.

23 Claims, 42 Drawing Sheets

Specification includes a Sequence Listing.

(56) References Cited

OTHER PUBLICATIONS

Eddy and Gold, "The phage T4 nrdB intron: a deletion mutant of a version found in the wild." Genes Dev (1991); 5(6): 1032-1041.
Eraso, et al., "The highly conserved MraZ protein is a transcriptional regulator in *Escherichia coli*." J Bacteriol (2014); 196(11): 2053-2066. Epub Mar. 21, 2014.
Fraipont, et al., "The integral membrane FtsW protein and peptidoglycan synthase PBP3 form a subcomplex in *Escherichia coli*." Microbiology (Reading) (2011); 157(Pt 1):251-259. Epub Sep. 16, 2010.
Gallagher, et al., "Rapid editing and evolution of bacterial genomes using libraries of synthetic DNA." Nat Protoc (2014); 9(10): 2301-2316. Epub Sep. 4, 2014.
Geis and Plapp, "Phospho-N-acetylmuramoyl-pentapeptide-transferase of *Escherichia coli* K12. Properties of the membrane-bound and the extracted and partially purified enzyme." Biochim Biophys Acta (1978); 527(2): 414-424.
Gibson, et al., "Creation of a bacterial cell controlled by a chemically synthesized genome." Science (2010); 329(5987):52-56. Epub May 20, 2010.
Gibson, et al., "Complete chemical synthesis, assembly, and cloning of a Mycoplasma genitalium genome." Science (2008); 319(5867): 1215-1220. Epub Jan. 24, 2008.
Giegé, et al., "Universal rules and idiosyncratic features in tRNA identity." Nucleic Acids Res (1998); 26(22): 5017-5035.
Grosjean, et al., "On the physical basis for ambiguity in genetic coding interactions." Proc Natl Acad Sci U S A (1978); 75(2): 610-614.
Ha, et al., "The 1.9 A crystal structure of *Escherichia coli* MurG, a membrane-associated glycosyltransferase involved in peptidoglycan biosynthesis." Protein Sci (2000); (6):1045-1052.
Hutchison, et al., "Design and synthesis of a minimal bacterial genome." Science (2016); 351(6280): aad6253.
International Preliminary Reporton Patentability in International Patent Application No. PCT/GB2017/052188 dated Jan. 29, 2019, 11 pages.
International Search Report in International Patent Application No. PCT/GB2017/052188 dated Oct. 16, 2017, 10 pages.
Ishii, et al., "Multiple high-throughput analyses monitor the response of *E. coli* to perturbations." Science (2007); 316(5824): 593-597. Epub Mar. 22, 2007.
Itaya, et al., "Combining two genomes in one cell: stable cloning of the Synechocystis PCC6803 genome in the Bacillus subtilis 168 genome." Proc Natl Acad Sci U S A (2005); 102(44): 15971-15976. Epub Oct. 18, 2005.
Itaya, et al., "Stable positional cloning of long continuous DNA in the Bacillus subtilis genome vector." J Biochem (2003); 134(4): 513-519.
Jiang, et al., "RNA-guided editing of bacterial genomes using CRISPR-Cas systems." Nat Biotechnol (2013); 31(3): 233-239. Epub Jan. 29, 2013.
Keseler, et al., "EcoCyc: fusing model organism databases with systems biology." Nucleic Acids Res (2013); 41 (Database issue): D605-612. Epub Nov. 9, 2012.
Khadria and Senes, "The transmembrane domains of the bacterial cell division proteins FtsB and FtsL form a stable high-order oligomer." Biochemistry (2013); 52(43): 7542-50. Epub Oct. 18, 2013.
Kimchi-Sarfaty, et al., "A "silent" polymorphism in the MDR1 gene changes substrate specificity." Science (2007); 315(5811): 525-528. Epub Dec. 21, 2006.
Kleinstiver, et al., "Engineered CRISPR-Cas9 nucleases with altered PAM specificities." Nature (2015); 523(7561): 481-485.
Kouprina, et al., "Selective isolation of large chromosomal regions by transformation-associated recombination cloning for structural and functional analysis of mammalian genomes." Methods Mol Biol (2006); 349: 85-101.
Krishnakumar, et al., "Simultaneous non-contiguous deletions using large synthetic DNA and site-specific recombinases." Nucleic Acids Res (2014); 42(14): e111. Epub Jun. 9, 2014.
Kudla, et al., "Coding-sequence determinants of gene expression in *Escherichia coli*." Science (2009); 324(5924): 255-258.
Kuhlman and Cox, "A place for everything: chromosomal integration of large constructs". Bioeng Bugs (Jul.-Aug. 2010); 1(4): 296-299. Epub May 13, 2010.
Lajoie, et al., "Probing the limits of genetic recoding in essential genes." Science (2013); 342(6156): 361-363.
Lajoie, et al., "Genomically recoded organisms expand biological functions." Science (2013); 342(6156): 357-360.
Lee, et al., "The Neisseria meningitidis CRISPR-Cas9 System Enables Specific Genome Editing in Mammalian Cells." Mol Ther (2016); 24(3): 645-654. Epub Jan. 19, 2016.
Li, et al., "Quantifying absolute protein synthesis rates reveals principles underlying allocation of cellular resources." Cell (2014); 157(3): 624-635.
Li, et al., "The anti-Shine-Dalgarno sequence drives translational pausing and codon choice in bacteria." Nature (2012); 484(7395): 538-541.
Mali, et al., "RNA-guided human genome engineering via Cas9." Science (2013); 339(6121): 823-826. Epub Jan. 3, 2013.
Mandell, et al., "Biocontainment of genetically modified organisms by synthetic protein design." Nature (2015); 518(7537): 55-60. Epub Jan. 21, 2015.
Mukai, et al., "Reassignment of a rare sense codon to a non-canonical amino acid in *Escherichia coli*." Nucleic Acids Res (2015); 43(16): 8111-8122. Epub Aug. 3, 2015.
Muyrers, et al., "RecE/RecT and Redalpha/Redbeta initiate double-stranded break repair by specifically interacting with their respective partners." Genes Dev (2000); 14(15): 1971-1982.
Newton, et al., "Analysis of any point mutation in DNA. The amplification refractory mutation system (ARMS)." Nucleic Acids Res (1989); 17(7): 2503-2516.
Nguyen-Distèche, et al., "The structure and function of *Escherichia coli* penicillin-binding protein 3." Cell Mol Life Sci (1998); 54(4): 309-316.
Pla, et al., "The native form of FtsA, a septal protein of *Escherichia coli*, is located in the cytoplasmic membrane." J Bacteriol (1990); 172(9): 5097-5102.
Pósfai, et al., "Emergent properties of reduced-genome *Escherichia coli*." Science (2006); 312(5776): 1044-1046. Epub Apr. 27, 2006.
Pratviel-Sosa, et al., "Over-production, purification and properties of the uridine diphosphate N-acetylmuramoyl-L-alanine:D-glutamate ligase from *Escherichia coli*." Eur J Biochem (1991); 202(3): 1169-1176.
Quax, et al., "Codon Bias as a Means to Fine-Tune Gene Expression." Mol Cell (2015); 59(2): 149-161.
Quax, et al., "Differential translation tunes uneven production of operon-encoded proteins." Cell Rep (2013); 4(5): 938-944. Epub Sep. 5, 2013.
Ran, et al., "In vivo genome editing using Staphylococcus aureus Cas9." Nature (2015); 520(7546): 186-191. Epub Apr. 1, 2015.
Ro, et al., "Production of the antimalarial drug precursor artemisinic acid in engineered yeast." Nature (2006); 440(7086): 940-943.
Robbins, et al., "Homing endonucleaseI-TevIII: dimerization as a means to a double-strand break." Nucleic Acids Res (2007); 35(5): 1589-1600. Epub Feb. 8, 2007.
Sakuma, et al., "MMEJ-assisted gene knock-in using TALENs and CRISPR-Cas9 with the PITCh systems." Nat Protoc (2016); 11(1): 118-33. Epub Dec. 17, 2015.
Sharp and Li, "The codon Adaptation Index—measure of directional synonymous codon usage bias, and its potential applications." Nucleic Acids Res (1987); 15(3): 1281-1295.
Sørensen and Pedersen, "Absolute in vivo translation rates of individual codons in *Escherichia coli*. The two glutamic acid codons GAA and GAG are translated with a threefold difference in rate." J Mol Biol (1991); 222(2): 265-280.
Traver, et al., "Homing endonucleases catalyze double-stranded DNA breaks and somatic transgene excision in Aedes aegypti." Insect Mol Biol (2009); 18(5): 623-633.
Tuller, et al., "Translation efficiency is determined by both codon bias and folding energy." Proc Natl Acad Sci U S A (2010); 107(8): 3645-3650. Epub Feb. 2, 2010.

(56) References Cited

OTHER PUBLICATIONS

Urbanus, et al., "Sec-dependent membrane protein insertion: sequential interaction of nascent FtsQ with SecY and YidC." EMBO Rep (2001); 2(6): 524-529.
Wang, et al., "Optimized orthogonal translation of unnatural amino acids enables spontaneous protein double-labelling and FRET." Nat Chern (2014); 6(5): 393-403. Epub Apr. 20, 2014.
Wang, et al., "Programming cells by multiplex genome engineering and accelerated evolution." Nature (2009); 460(7257): 894-898. Epub Jul. 26, 2009.
Weiss, et al., "Localization of the *Escherichia coli* cell division protein FtsI (PBP3) to the division site and cell pole." Mol Microbiol (1997); 25(4): 671-681.
Zetsche, et al., "Cpf1 is a single RNA-guided endonuclease of a class 2 CRISPR-Cas system." Cell (2015); 163(3): 759-771. Epub Sep. 25, 2015.
Zhang, et al., "Transient ribosomal attenuation coordinates protein synthesis and co-translational folding." Nat Struct Mol Biol (2009); 16(3): 274-280. Epub Feb. 8, 2009.
Rutz, Berthold, Written Opinion of Int'l Search Authority (PCT/GB2017/052188 dated Oct. 16, 2017.
Kuhlman, Thomas E., "Site-specific chromosomal integration of large synthetic constructs," Nucleic Acids Research, vol. 38, No. 6, Jan. 4, 2010.
Lee, David J. et al., "Gene doctoring: a method for recombineering in laboratory and pathogenic *Escherichia coli* strains," BMC Mocrobiology, vol. 9 p. 252, Dec. 9, 2009.
Li, Mamie Z, et al., "MAGIC, an in vivo genetic method for the rapid construction of recombinant DNA molecules," Nature Genetics, vol. 37,No. 3, pp. 311-319, Jan. 20, 2005.
Yang, Junjie, et al., "Multiple-site genetic modifications in *Escherichia coli* using lambda-Red recombination and l-SceI cleavage," Biotechnol Letters, vol. 37, pp. 2011-2018, Jun. 2015.
Yang, Junjie, et al., "High-Efficiency Scarless Genetic Modification in *Escherichia coli* by Using Lambda Red Recombination an d l-SceI Cleavage," Applied and Environmental Microbiology, vol. 80, No. 13, pp. 3826-3834, Apr. 2014.
Gong, Wei, et al., "Ends-out, or replacement, gene targeting in *Drosophila*," Proceedings National Academy of Sciences, vol. 100, No. 5, pp. 2556-2561, Mar. 4, 2003.
Holkers, Maarten, et al., "Adenoviral vector DNA for accurate genome editing with engineered nucleases," Nature Methods, vol. 11, No. 10, Oct. 2014.
Pyne, Michael, et al., "Coupling the CRISPR/Cas9 System with Lambda Red Recombineering Enables Simplified Chromosomal Gene Replacement in *Escherichia coli*," Applied and Environmental Microbiology, vol. 81, No. 15, pp. 5103-5114, Aug. 2015.
Gibson, Daniel G., et al.,Complete Chemical Synthesis, Assembly, and Cloning of a Mycoplasma genitalium Genome, Science, vol. 319 pp. 1215-1220,Feb. 29, 2018.
Hutchison, Clyde A., et al., "Design and synthesis of a minimal bacterial genome," Science, vol. 351, No. 6280, Mar. 25, 2016.
Hoshijima, Kazuyuki, et al., "Precise Editing of the Zebrafish Genome Made Simple and Efficient," Development Cell, vol. 36, pp. 654-667, Mar. 21, 2016.
Lajoie, Marc j., et al., "Genomically Recoded Organisms Expand Biological Functions," Science, vol. 342, pp. 357-363, Oct. 18, 2013.
Rovner, Alexis J., et al., "Recoded organisms engineered to depend on synthetic amino acids," Nature, vol. 518, Feb. 5, 2015.
Wang, Kaihang, et al., "Defining synonymous codon compression schemes by genome recoding," Nature, vol. 539, Nov. 3, 2016.
Jinek et al., "A programmable dual-RNA-guided DNA endonuclease in adaptive bacterial immunity," Science. 337(6096):816-21 (2012) (7 pages).
Anders et al., "Structural basis of PAM-dependent target DNA recognition by the Cas9 endonuclease," Nature. 513(7519):569-73 (2014) (16 pages).
Esvelt et al., "Orthogonal Cas9 proteins for RNA-guided gene regulation and editing," Nat Methods. 10(11):1116-21 (2013) (8 pages).
Slaymaker et al., "Rationally engineered Cas9 nucleases with improved specificity," Science. 351(6268):84-8 (2016) (6 pages).
Kleinstiver et al., "High-fidelity CRISPR-Cas9 nucleases with No. detectable genome-wide off-target effects," Nature. 529(7587):490-5 (2016) (17 pages).
Shen et al., "Efficient genome modification by CRISPR-Cas9 nickase with minimal off-target effects," Nature. 11(4):399-402 (2014) (6 pages).
Tsai et al., "Dimeric CRISPR RNA-guided FokI nucleases for highly specific genome editing," Nat Biotechnol. 32(6):569-76 (2014) (9 pages).
Gao et al., "DNA-guided genome editing using the Natronobacterium gregoryi Argonaute," Nat Biotechnol. 34(7):768-73 (2016) (9 pages).
Swarts et al., "DNA-guided DNA interference by a prokaryotic Argonaute," Nature. 507(7491):258-261 (2014) (17 pages).
Swarts et al. "Argonaute of the archaeon Pyrococcus furiosus is a DNA-guided nuclease that targets cognate DNA," Nucleic Acids Res. 43(10):5120-9 (2015).

\* cited by examiner

FIGURE 1
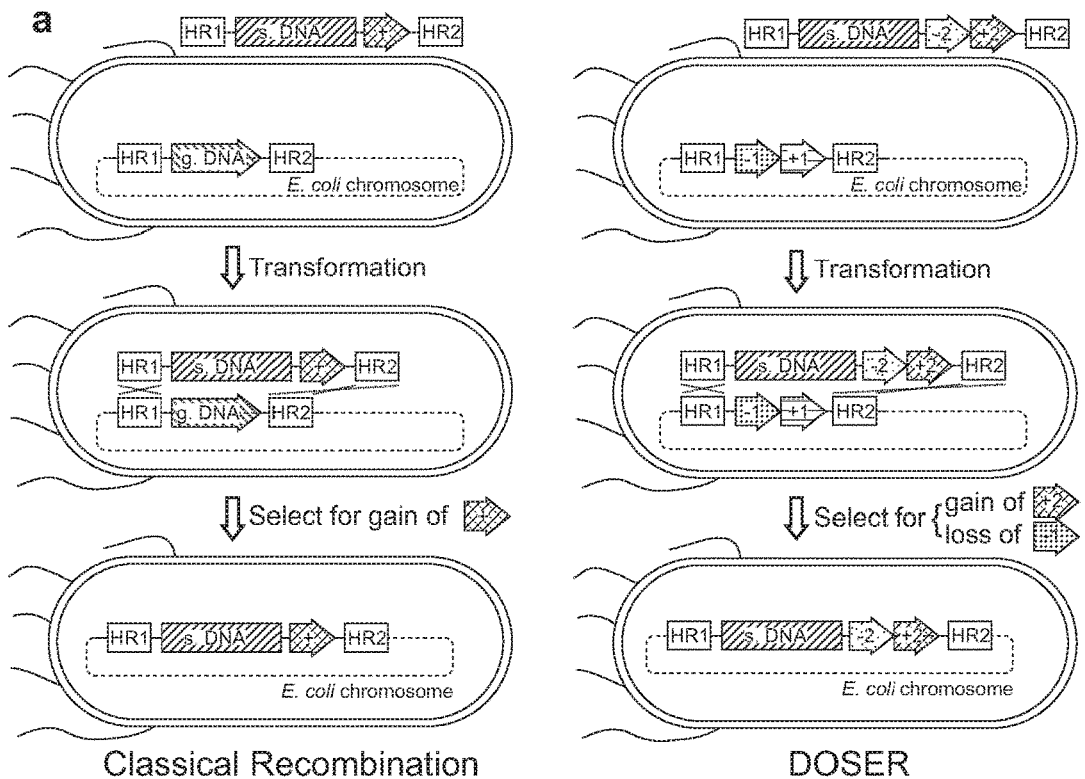
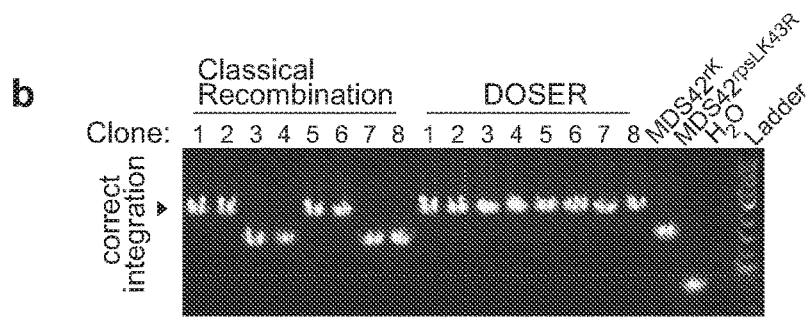
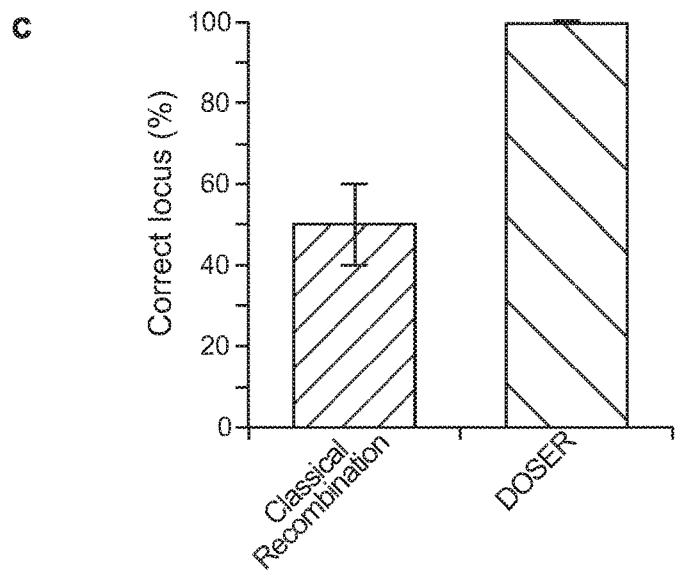

FIGURE 2
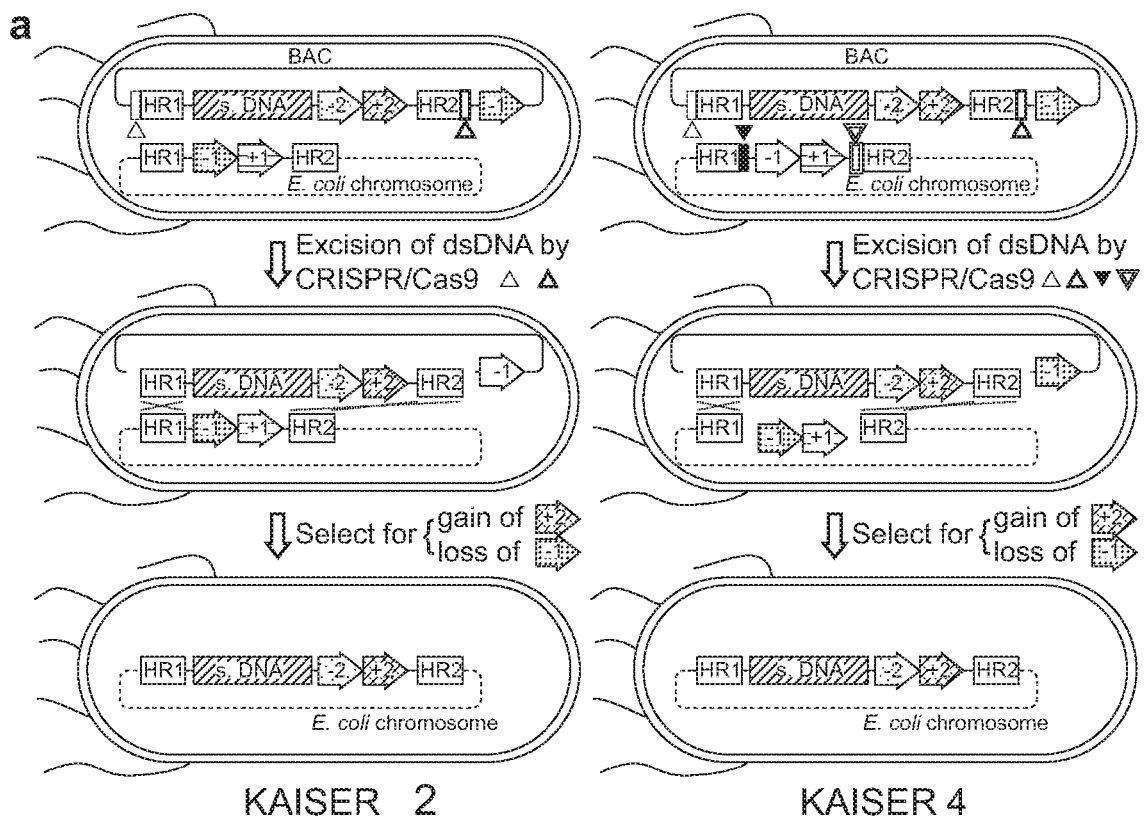
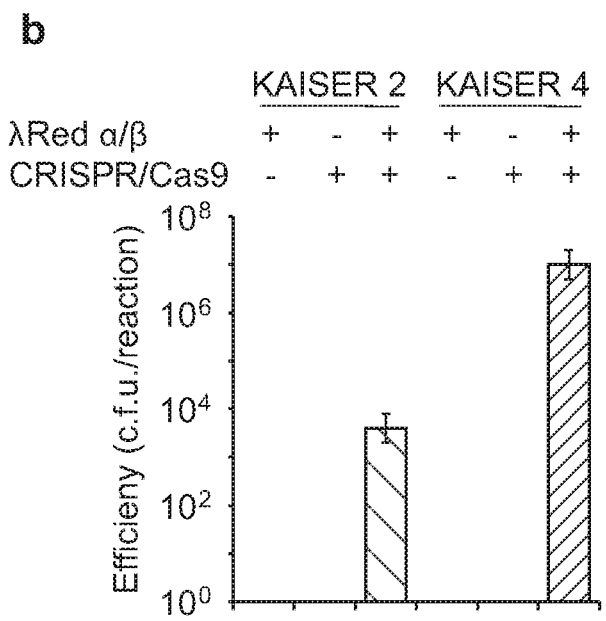
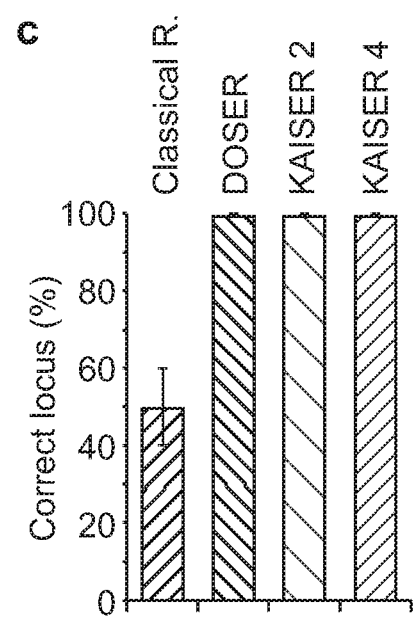

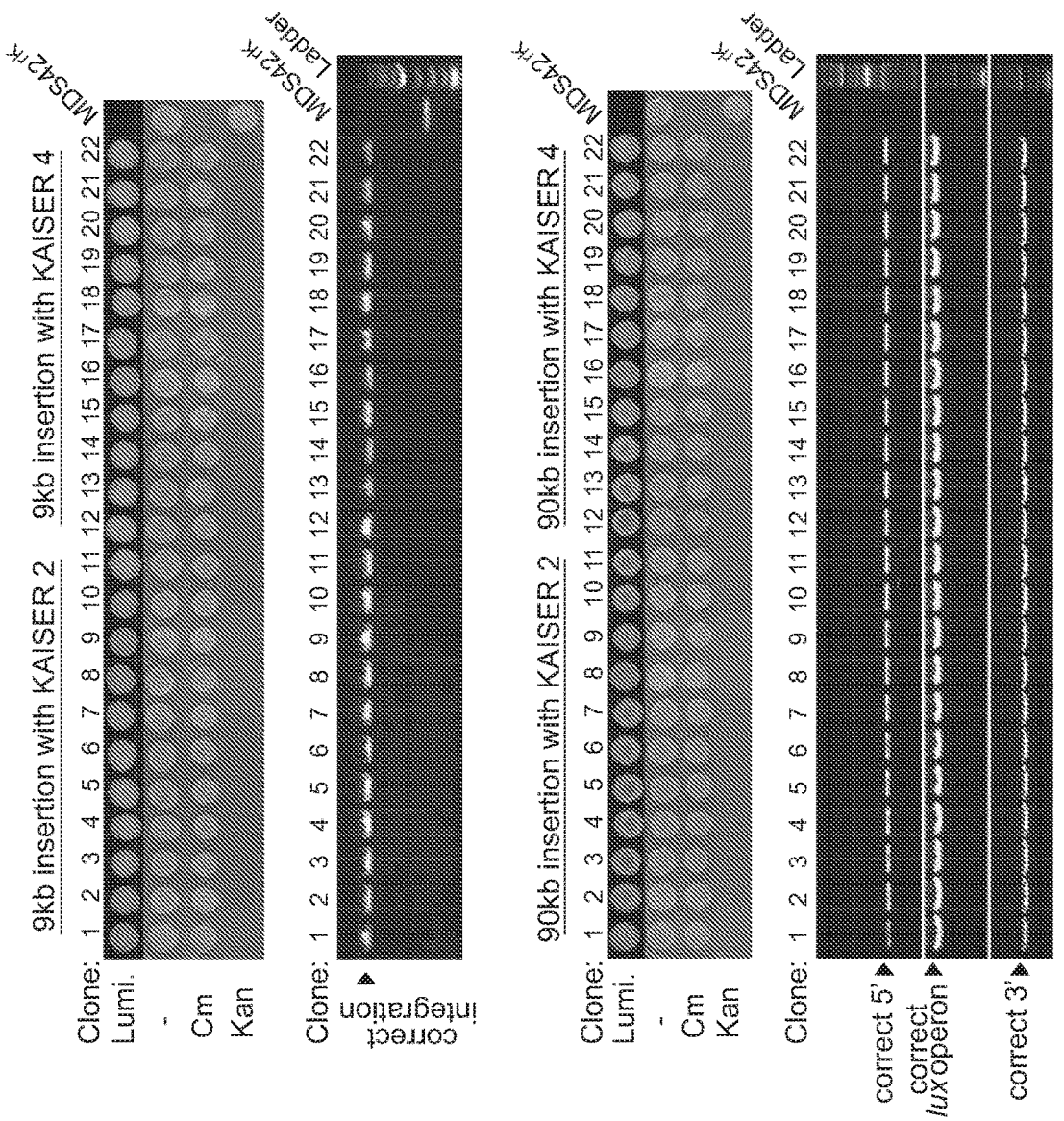
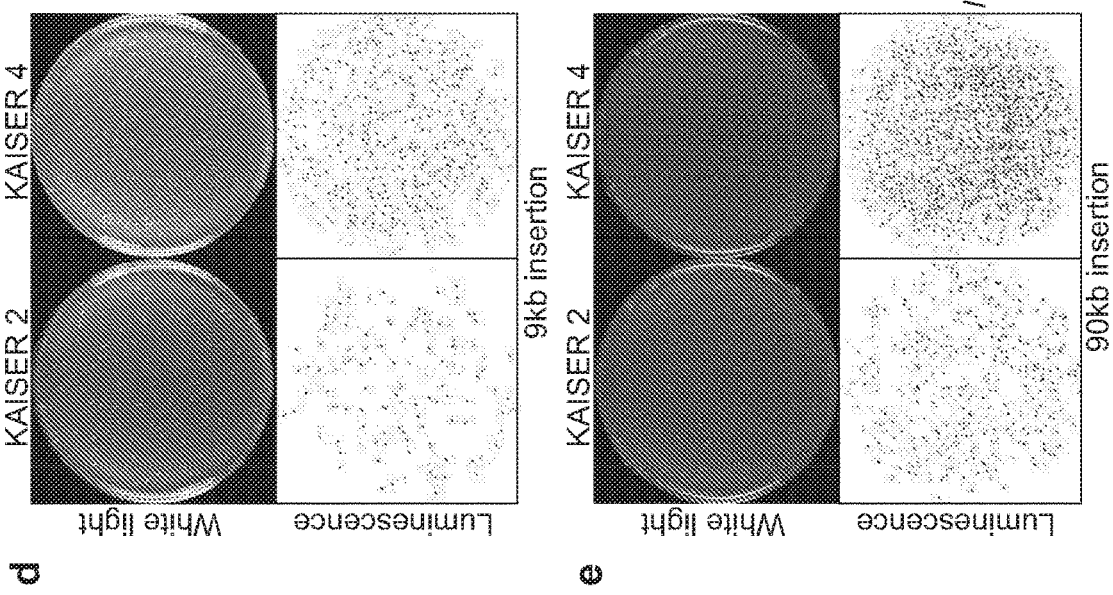
FIGURE 2 continued

FIGURE 3 continued
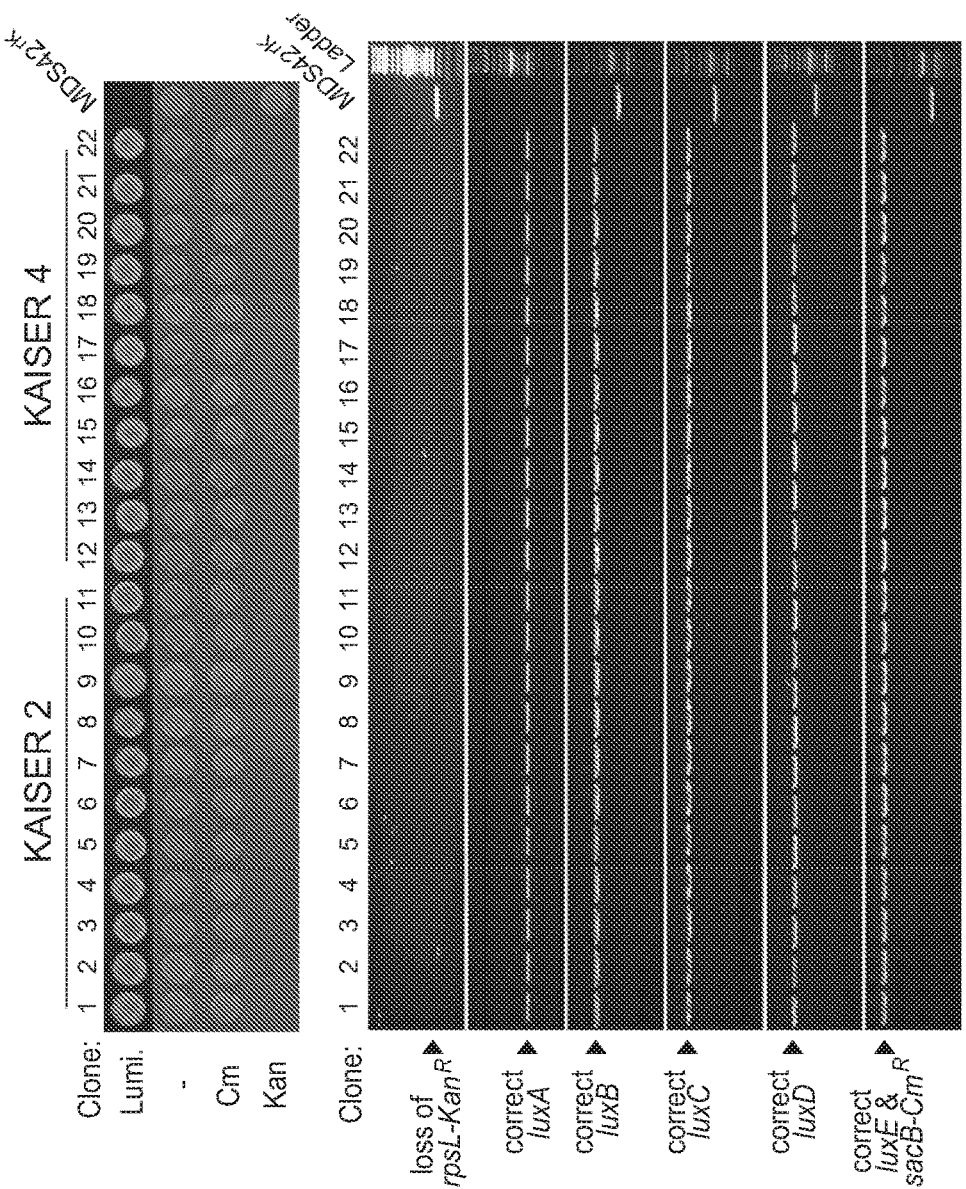
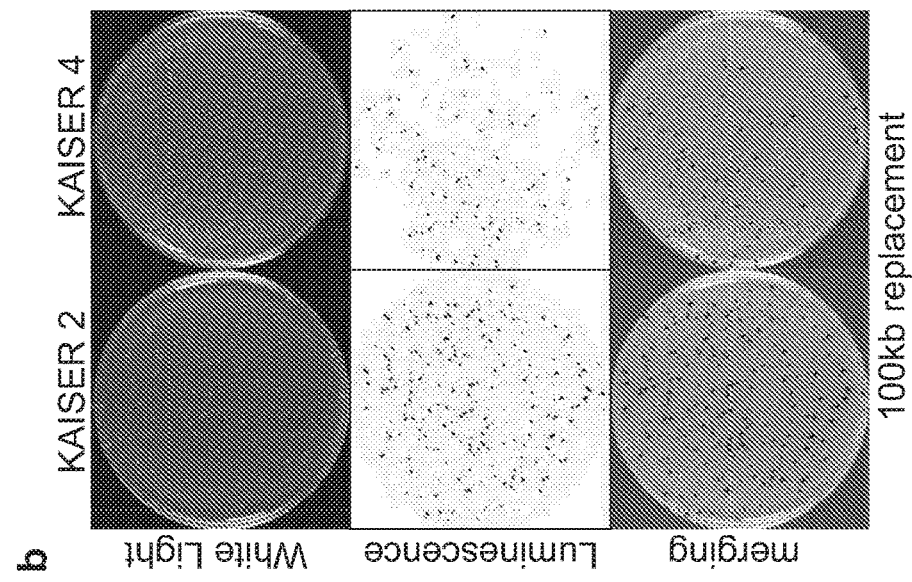

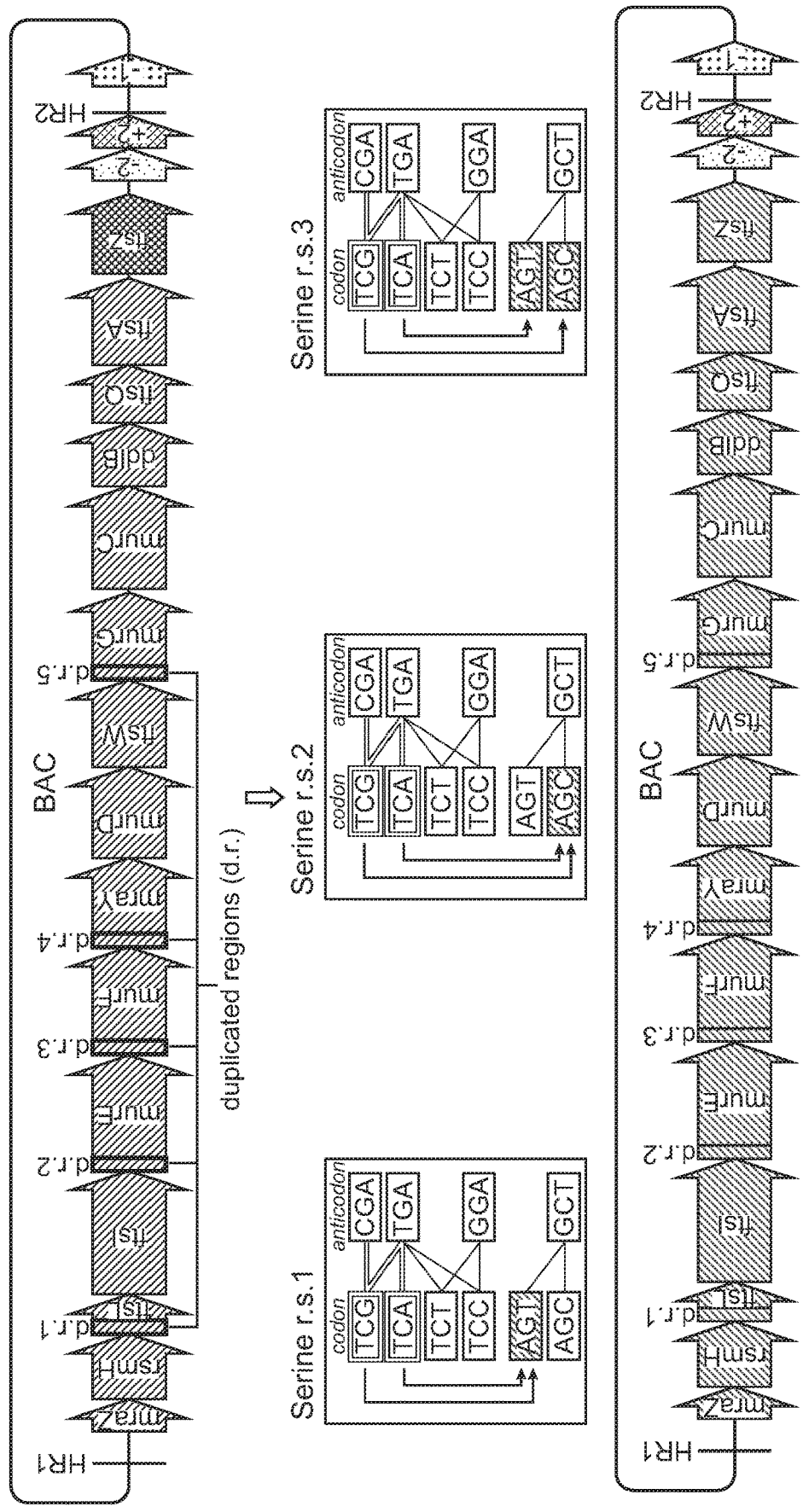

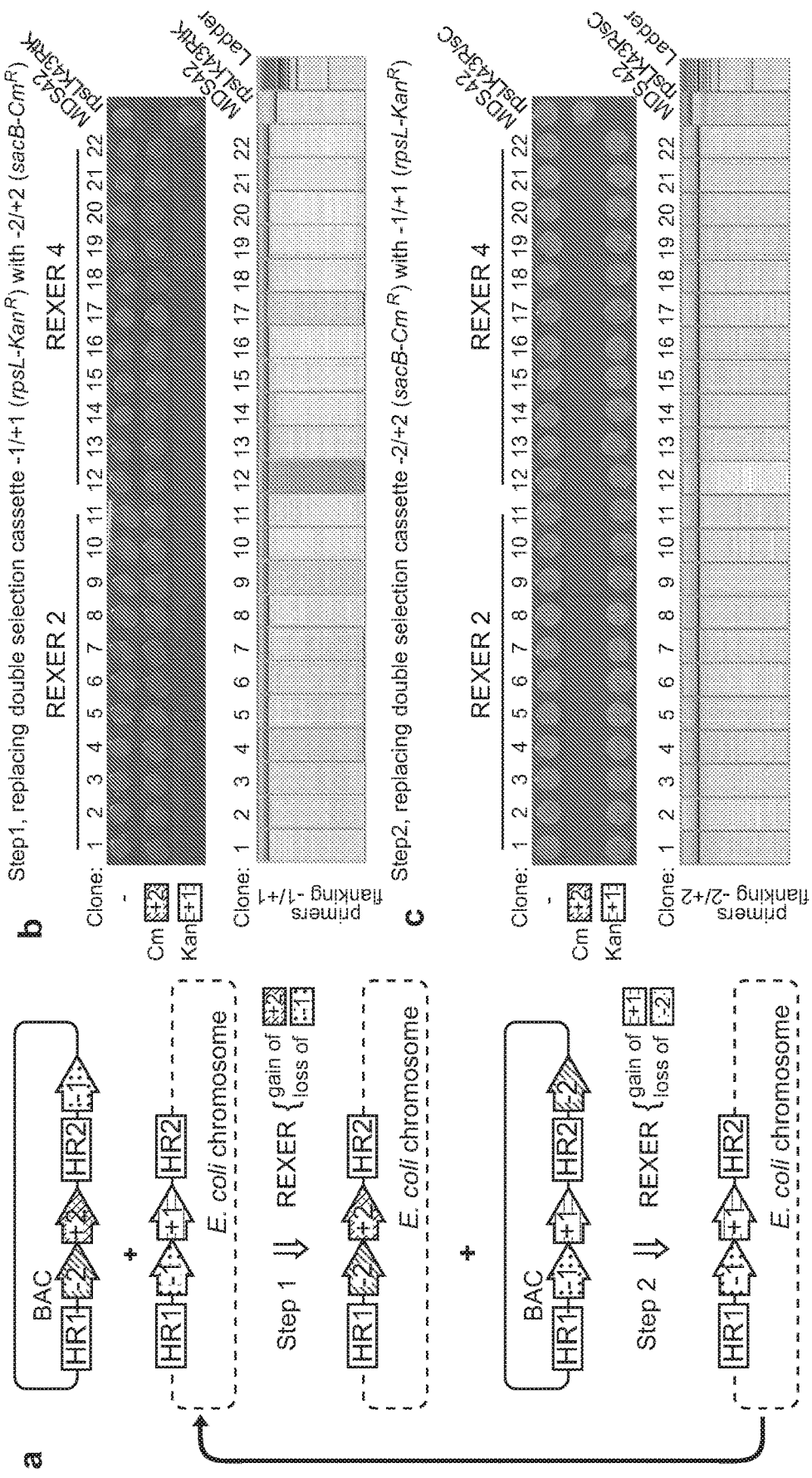
FIGURE 9 (supplementary figure 2)

FIGURE 9 (supplementary figure 2) continued
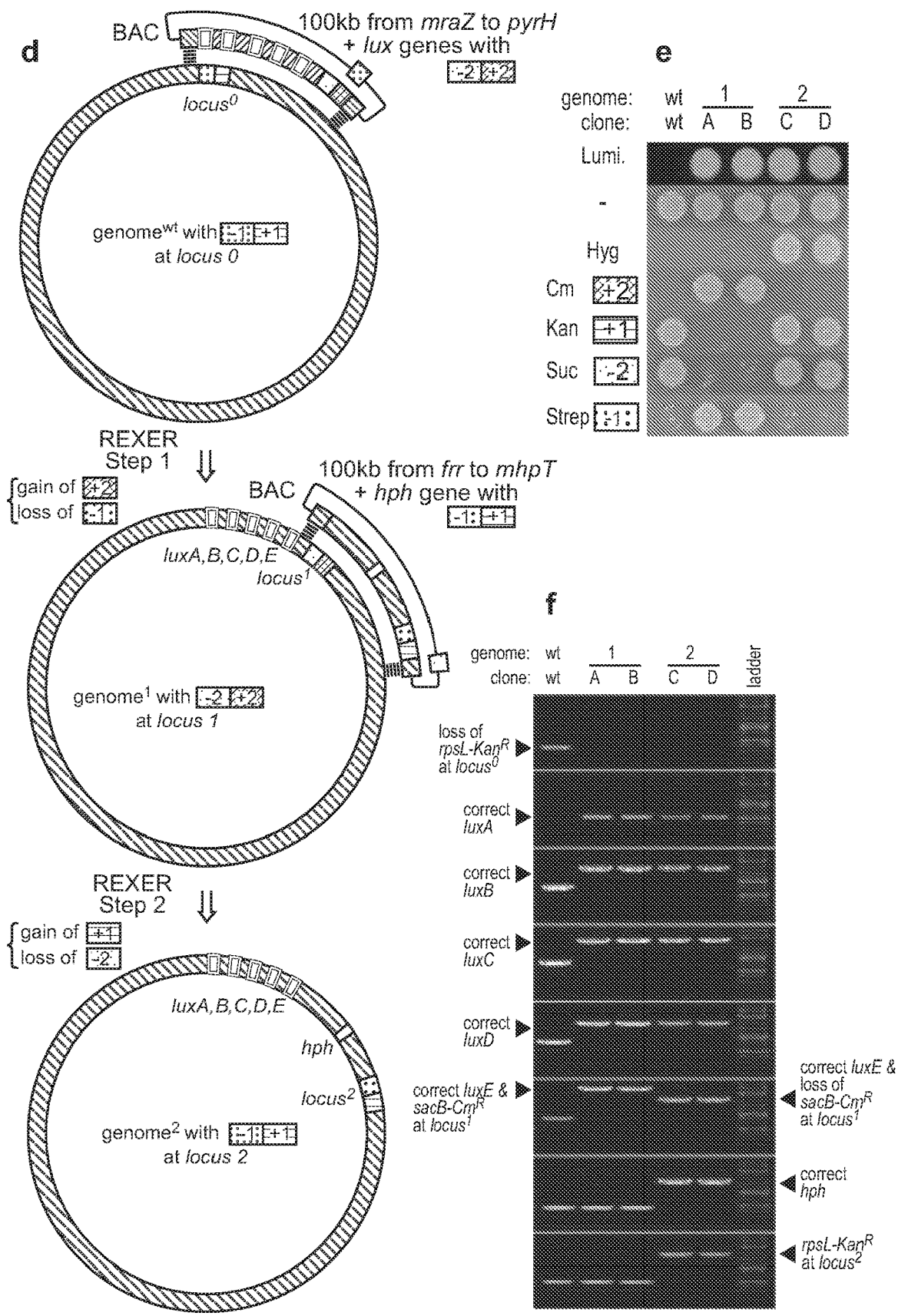

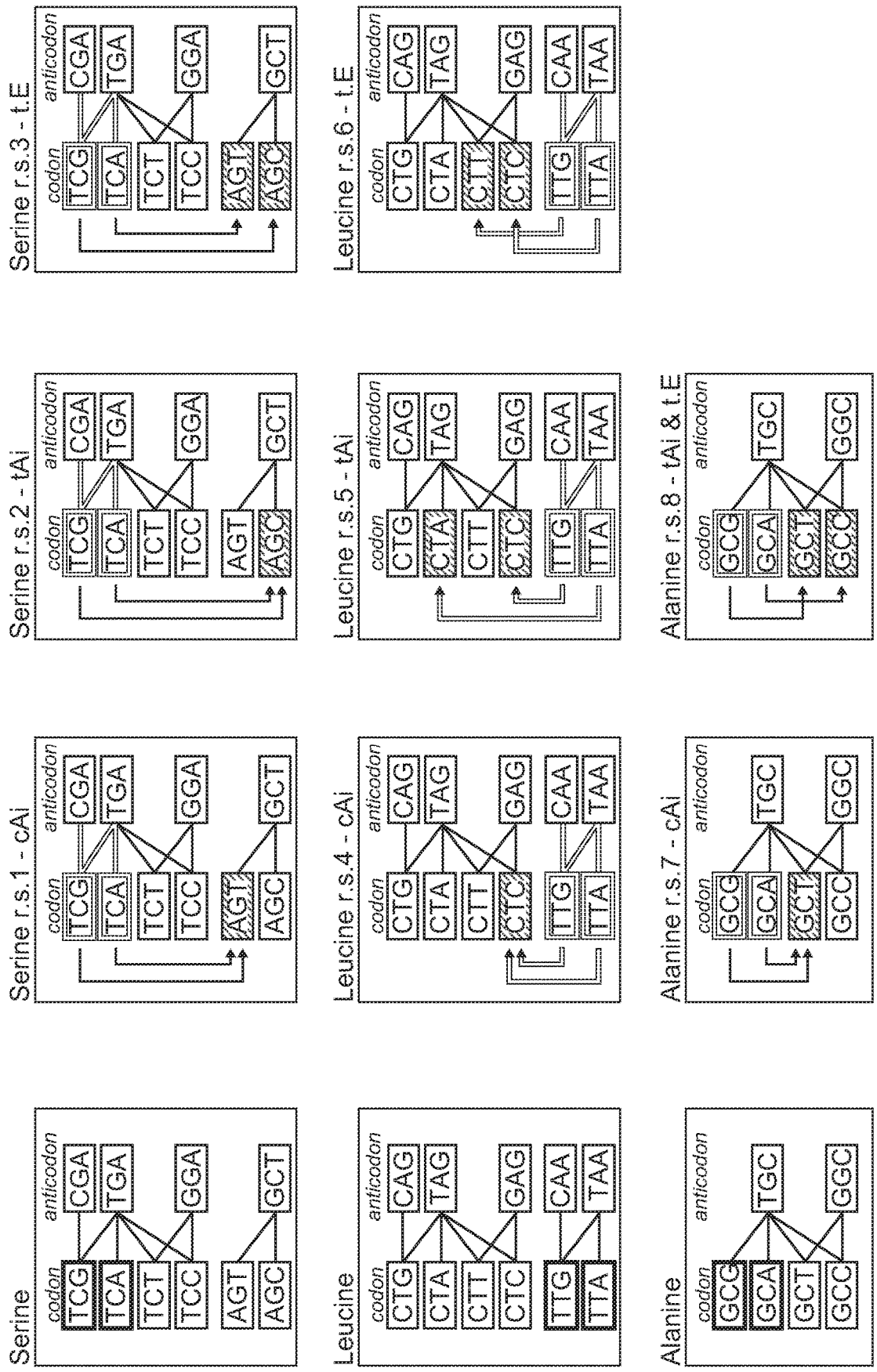
FIGURE 10 (supplementary figure 3)

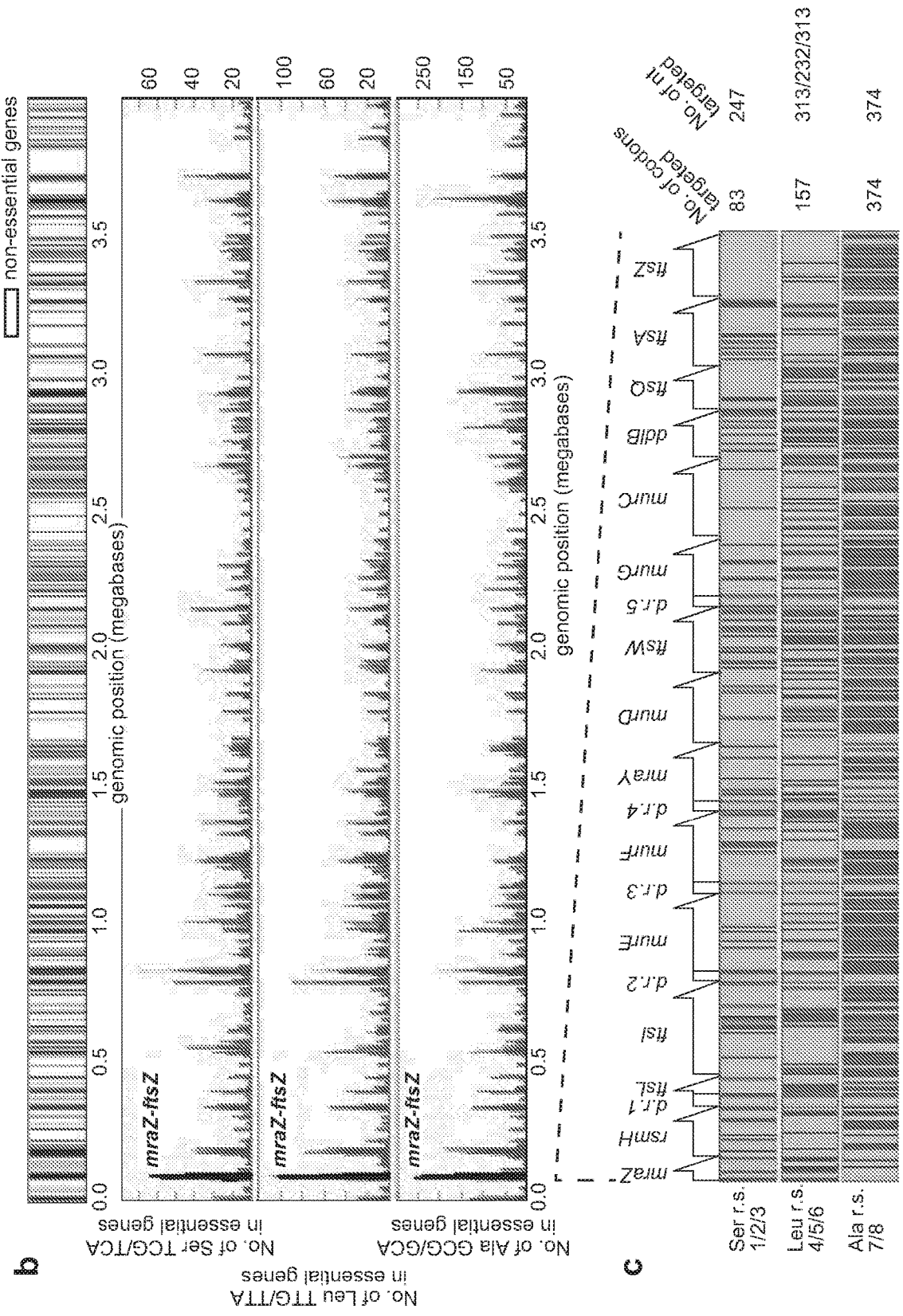
FIGURE 10 (supplementary figure 3) continued

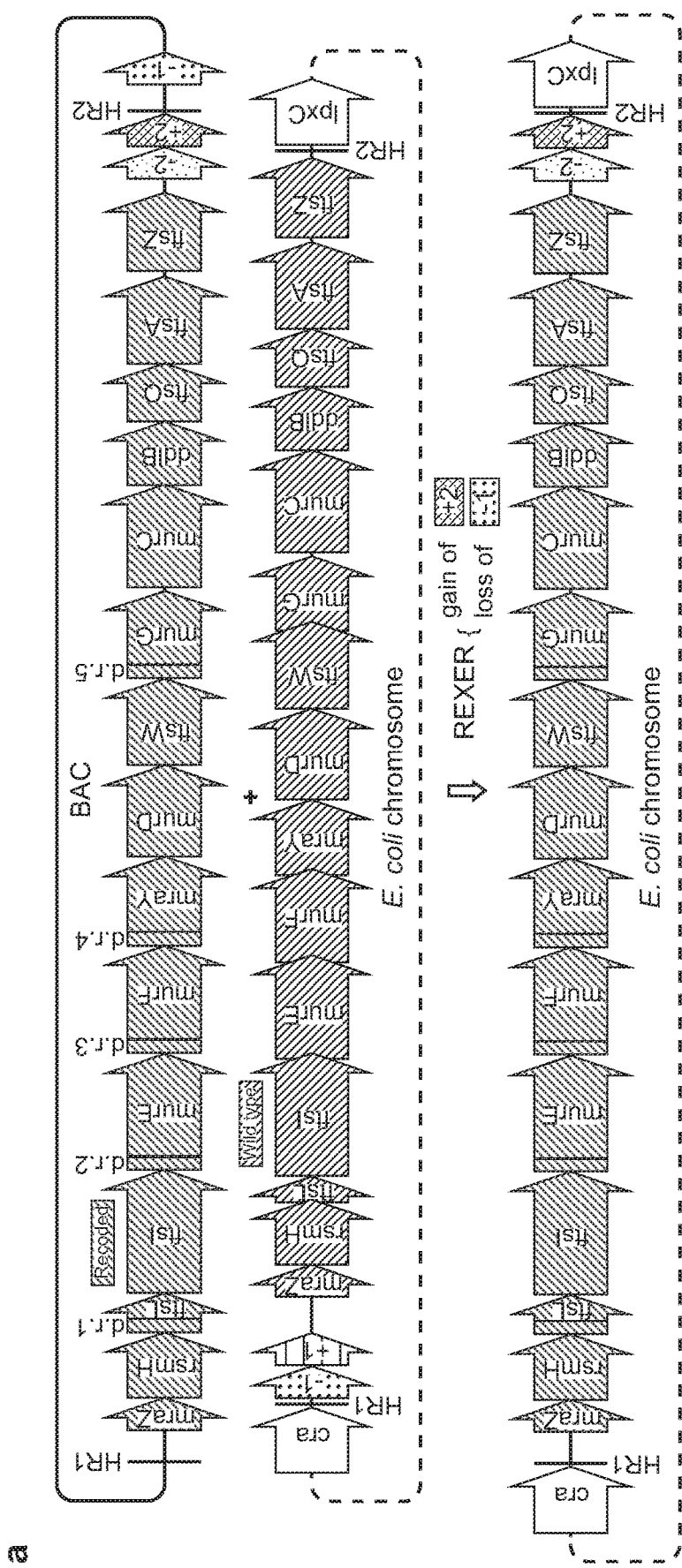
FIGURE 11 (supplementary figure 4)

FIGURE 11 (supplementary figure 4) continued
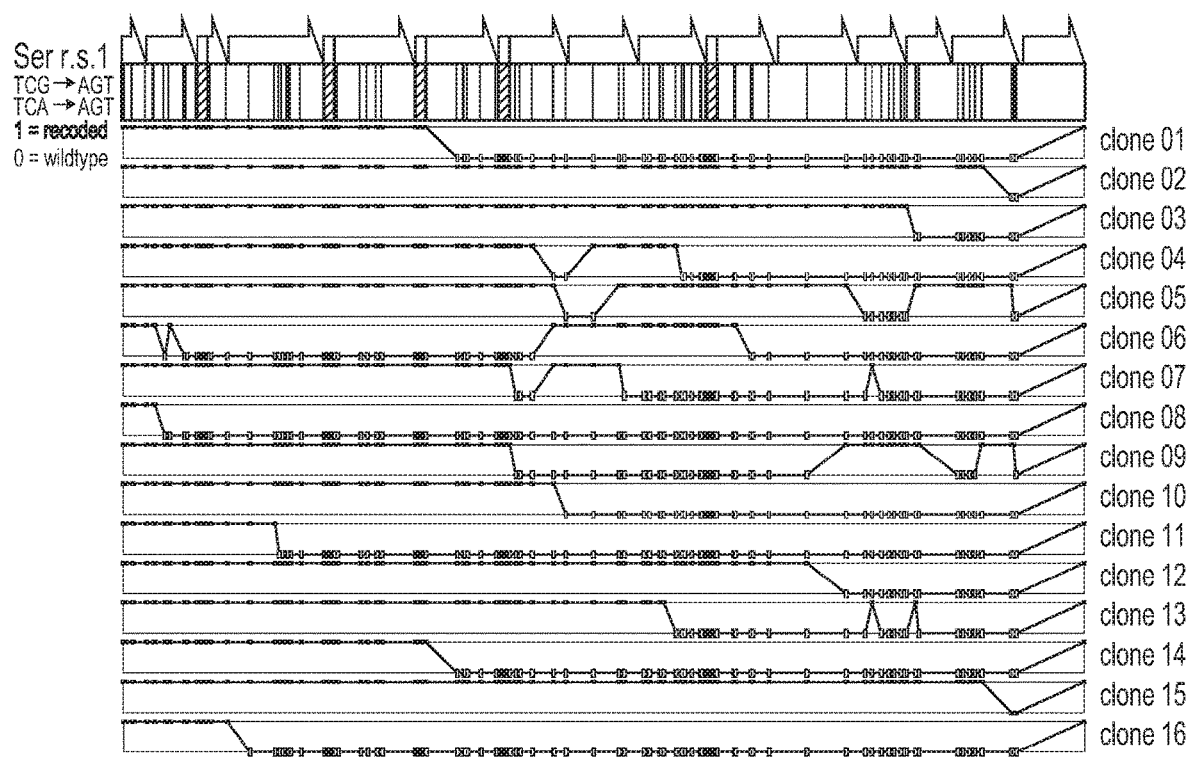
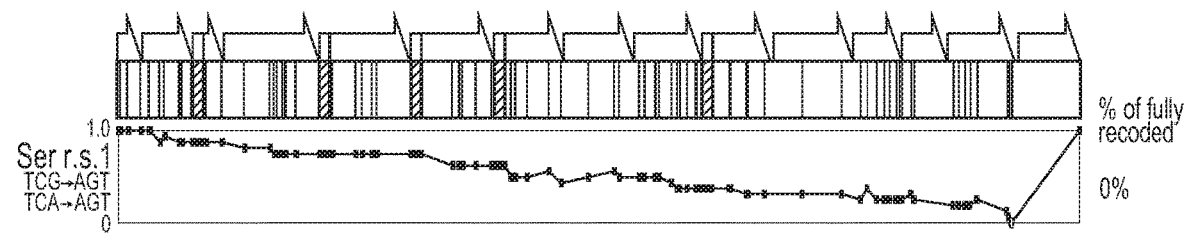

FIGURE 12 (supplementary figure 5)
a
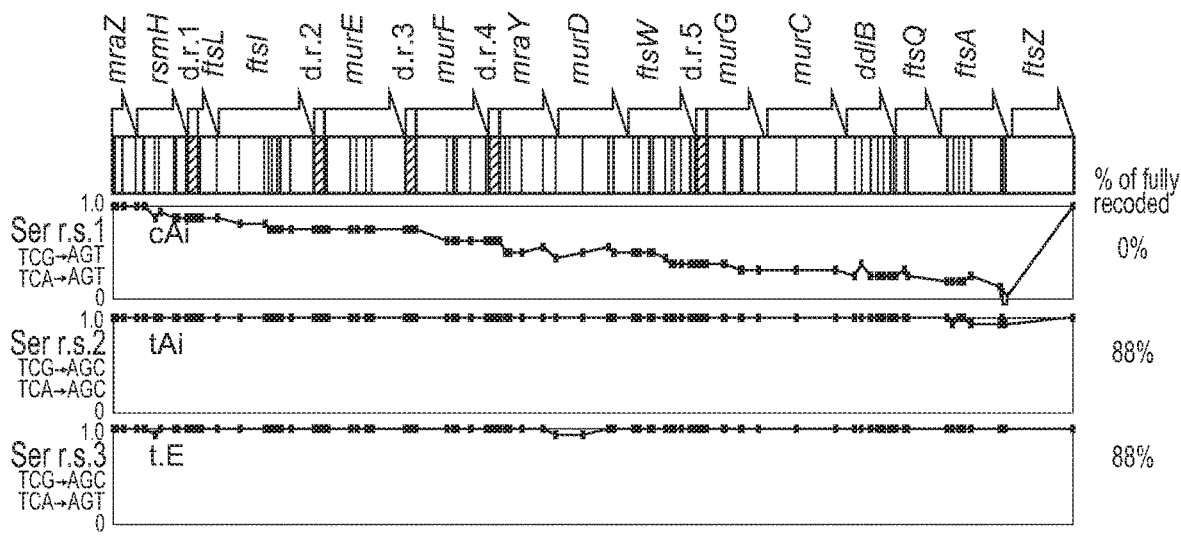
b
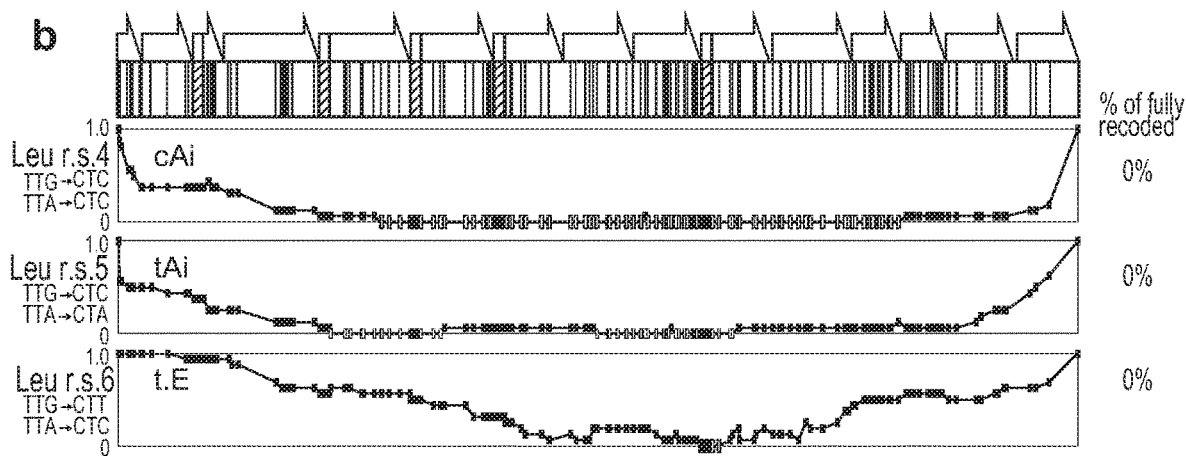
c
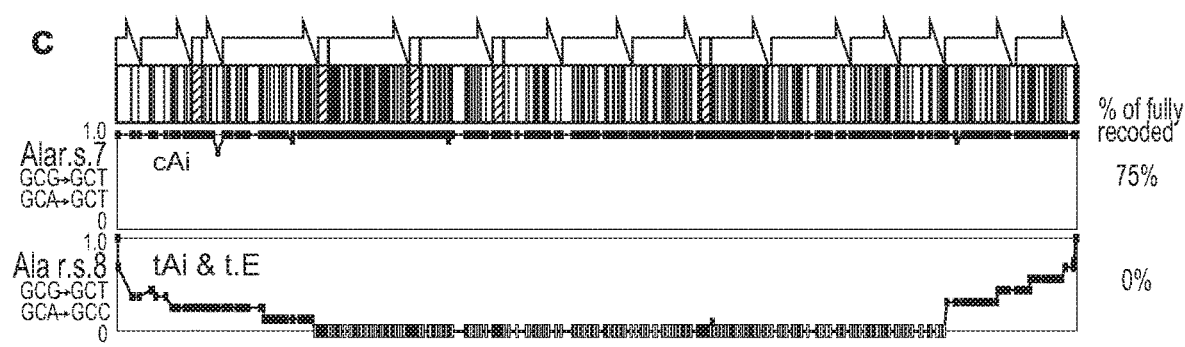

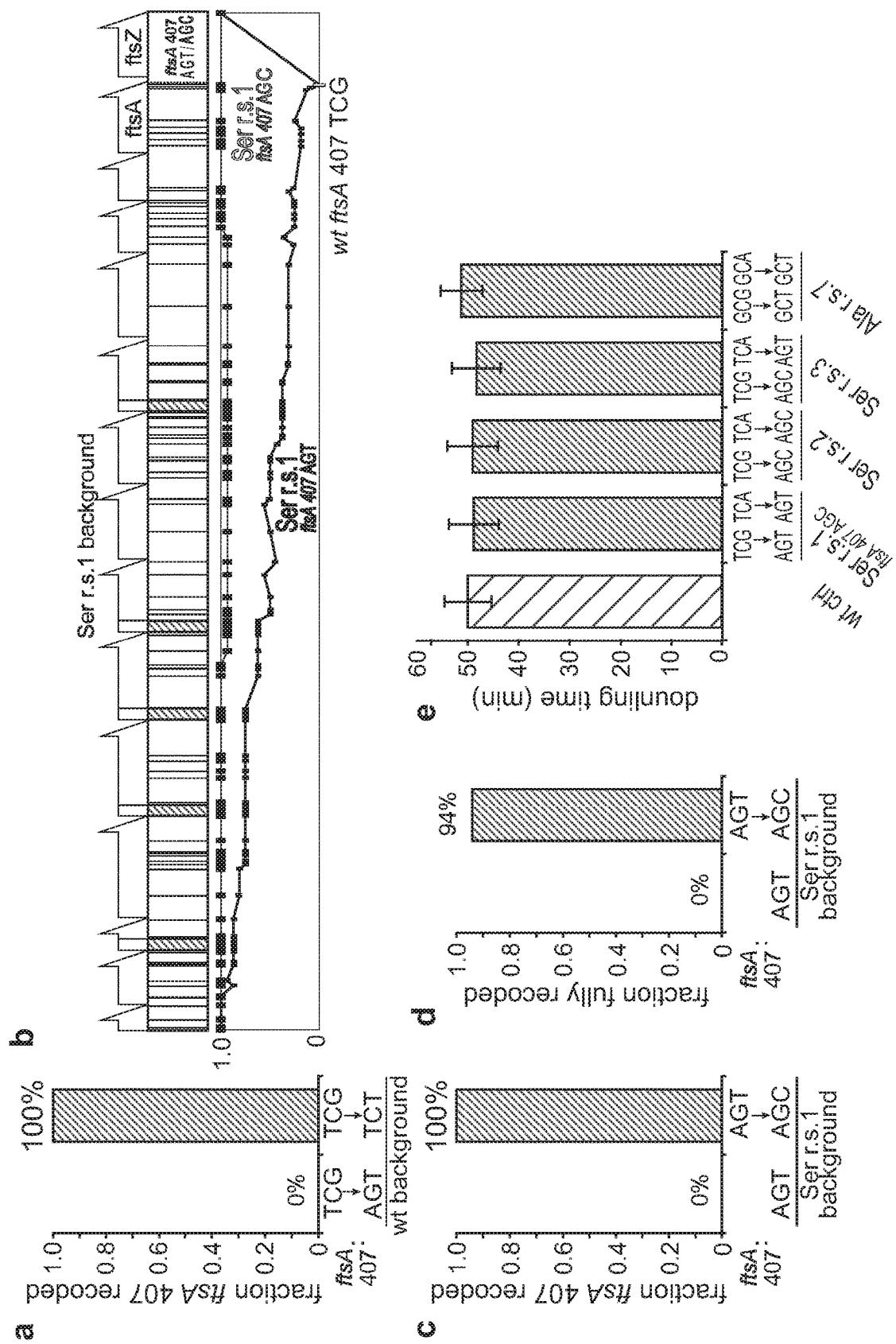
FIGURE 13 (supplementary figure 6)

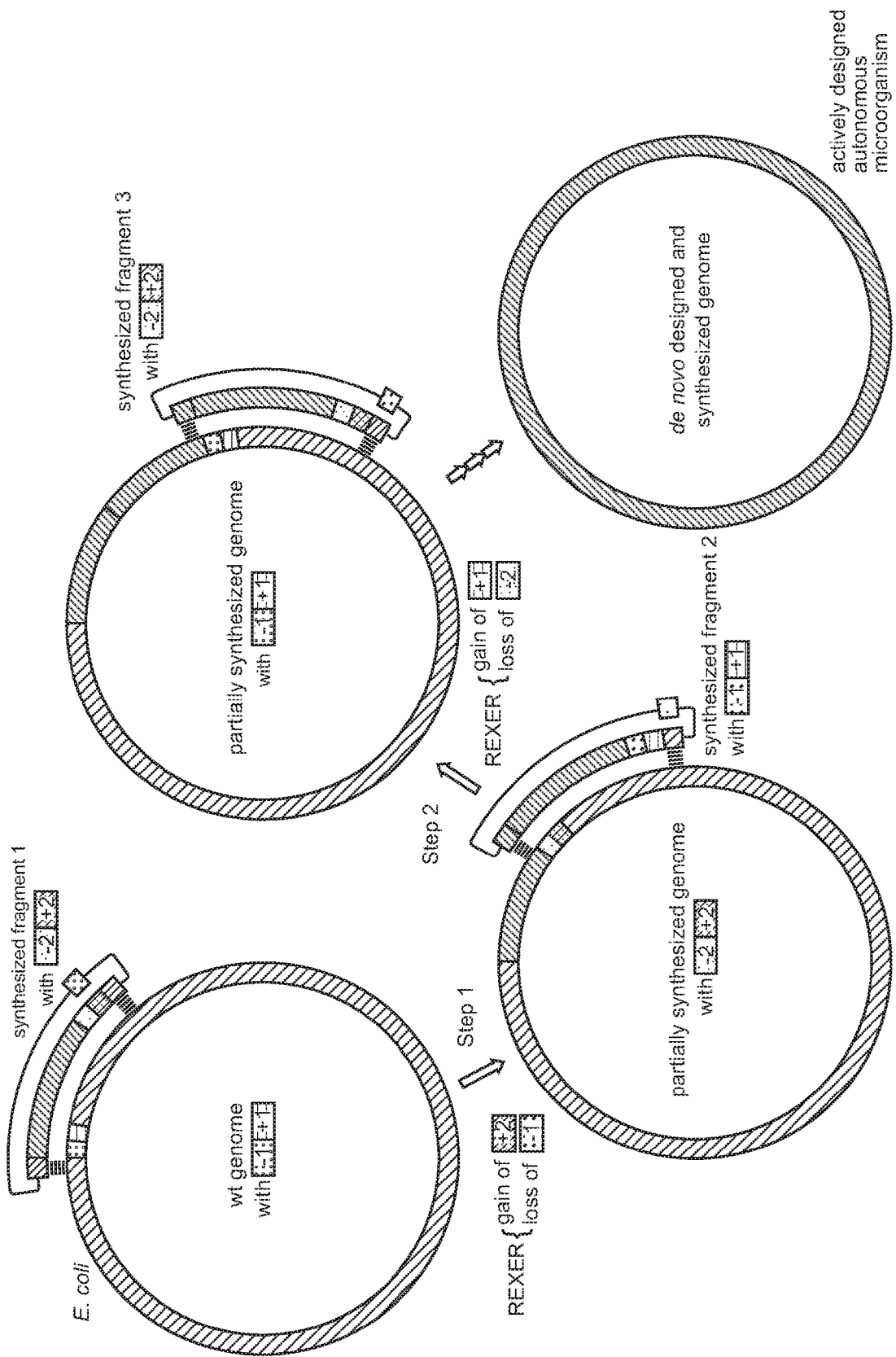
FIGURE 14 (extended data figure 6)

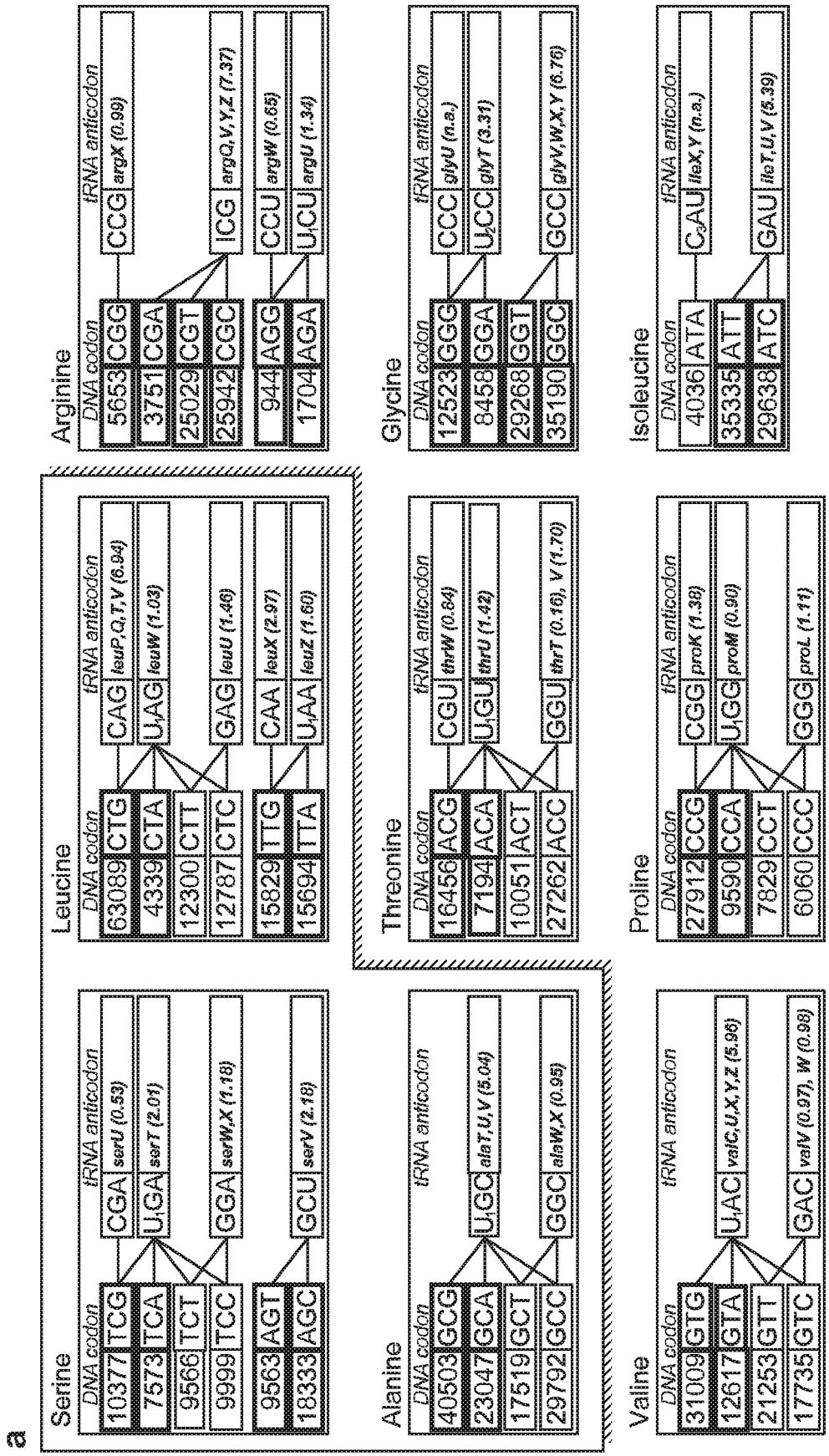
FIGURE 15 (extended data figure 7)

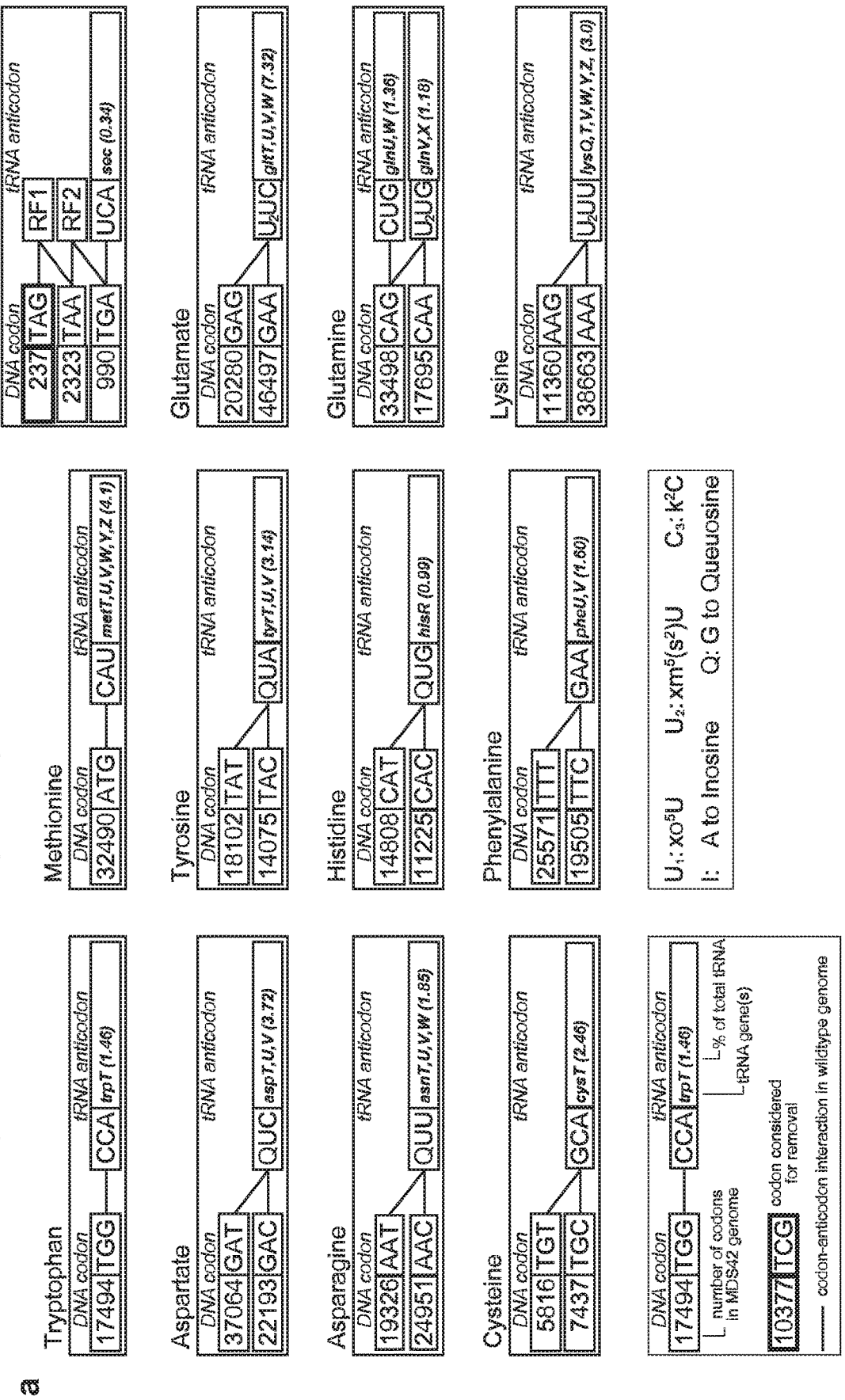
FIGURE 15 (extended data figure 7) continued

FIGURE 15 (extended data figure 7) continued
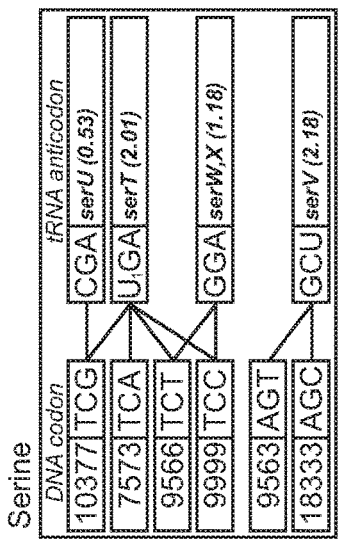
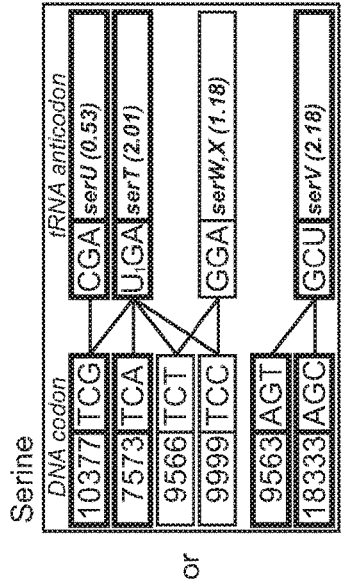
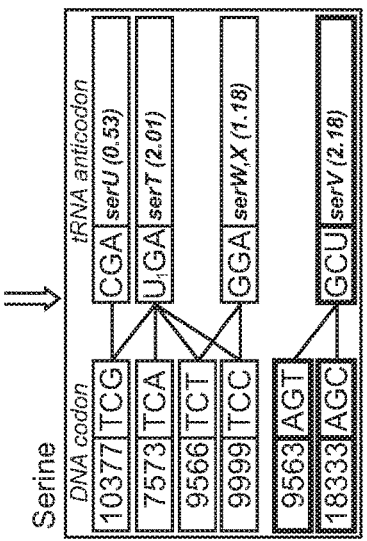
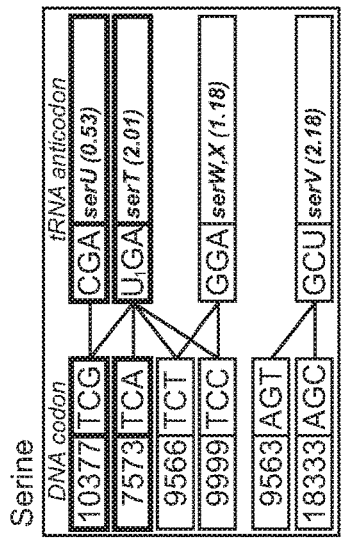
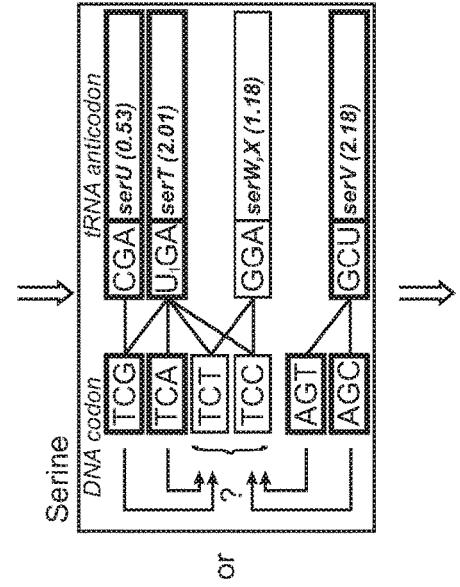
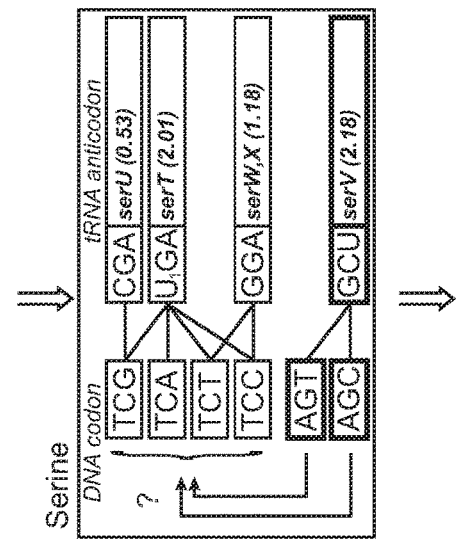
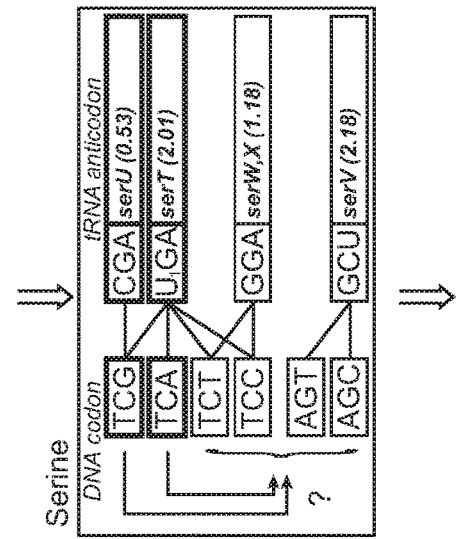

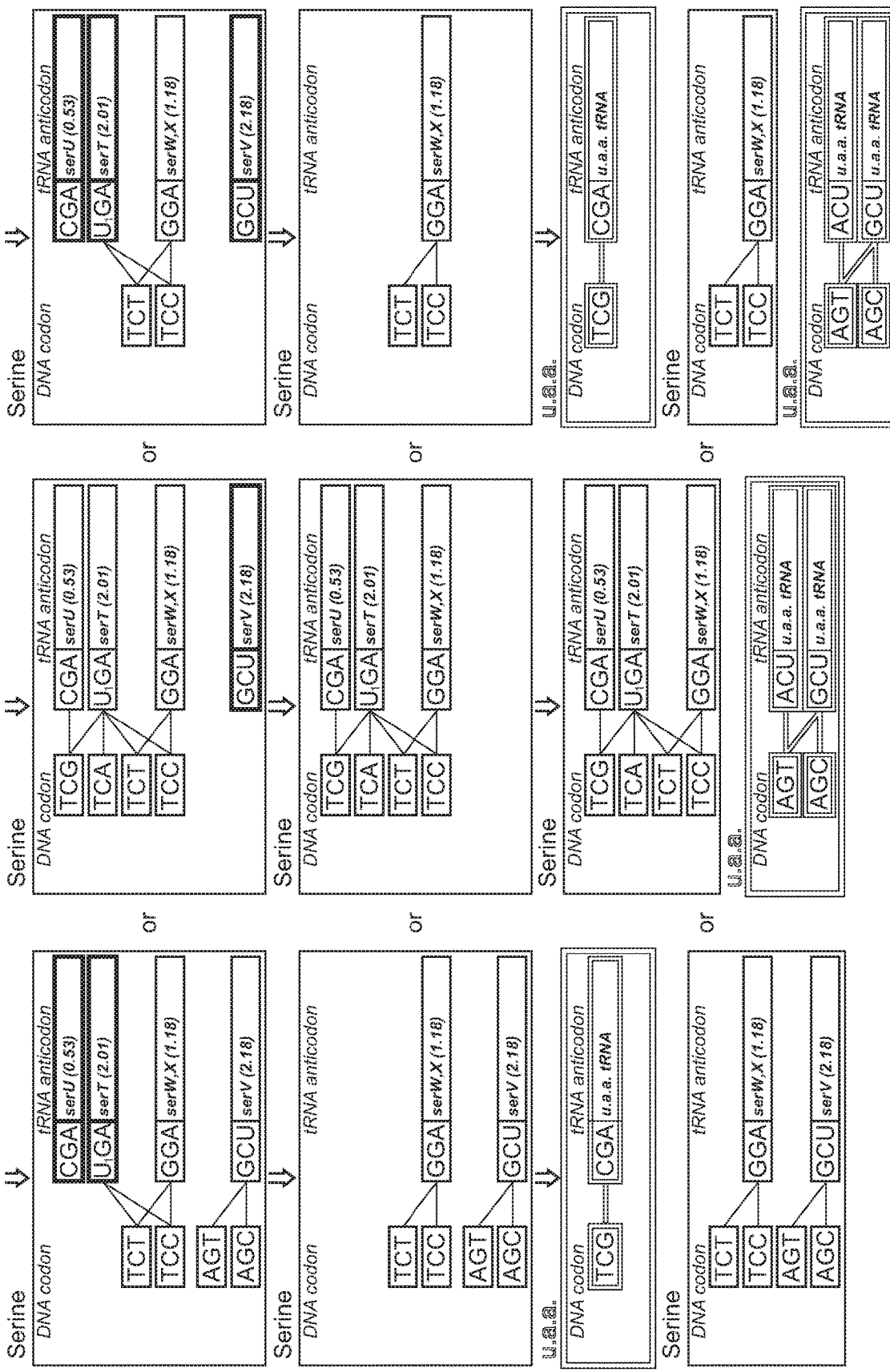
Figure 15 (extended data figure 7) continued

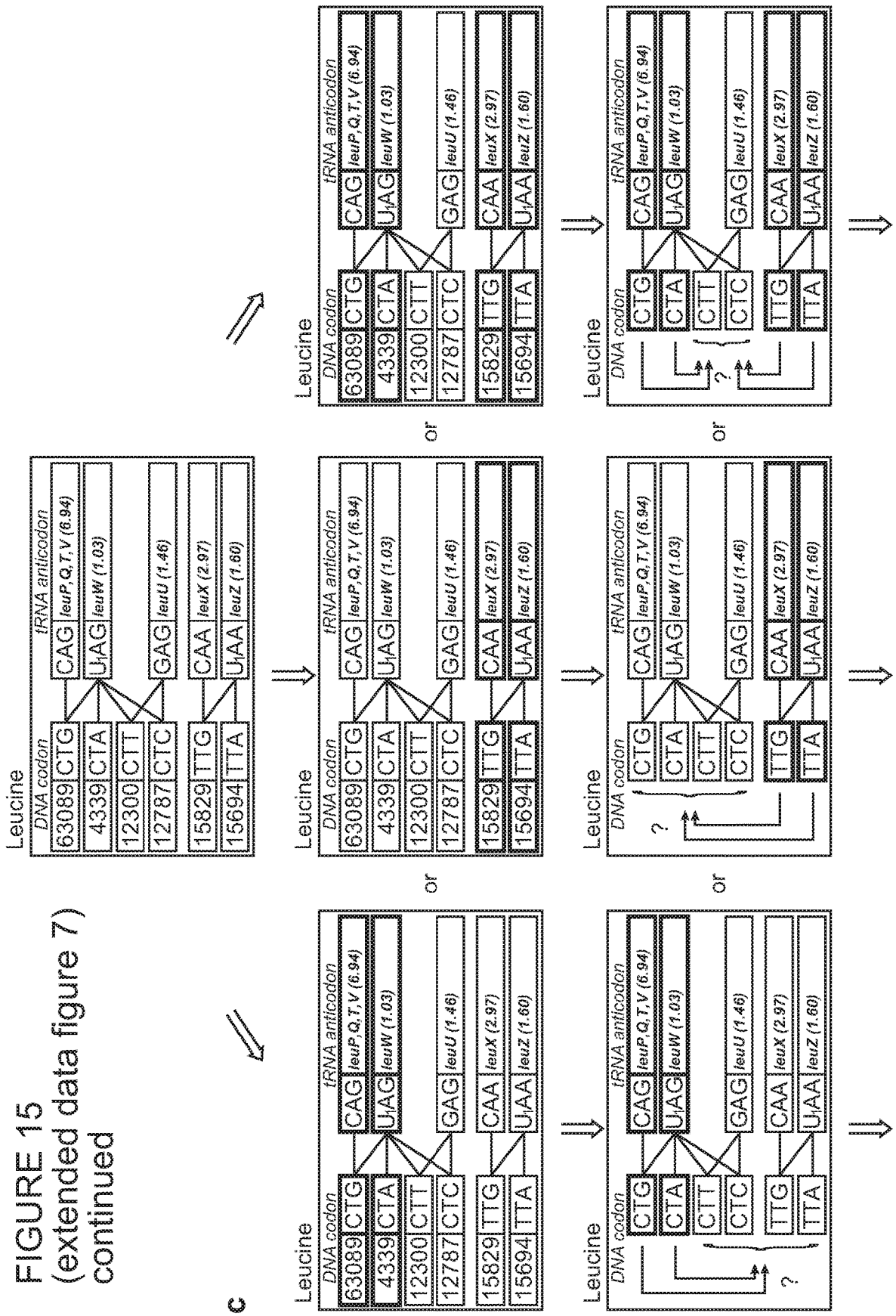
FIGURE 15 (extended data figure 7) continued

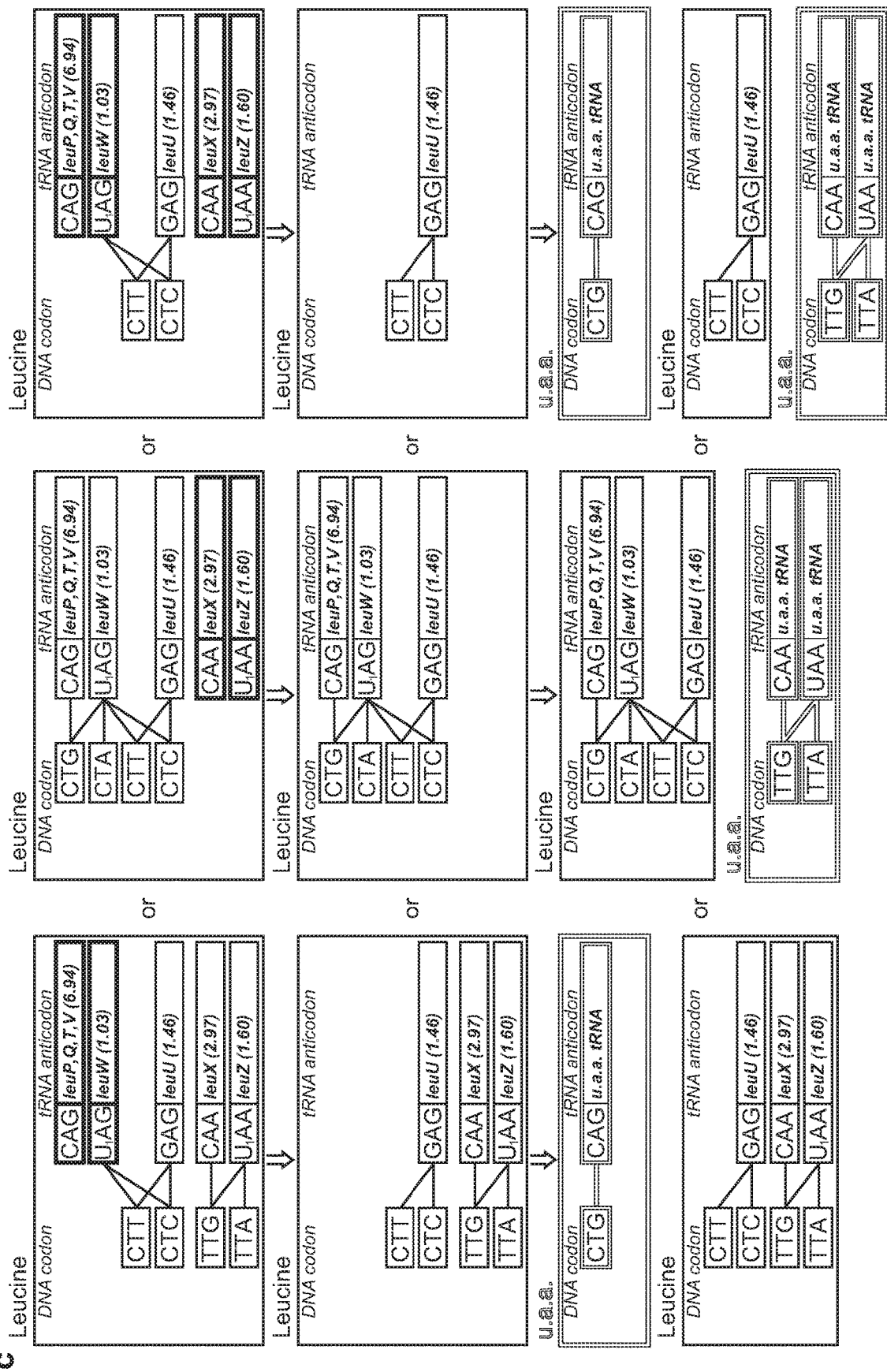
FIGURE 15 (extended data figure 7) continued

FIGURE 15 (extended data figure 7) continued
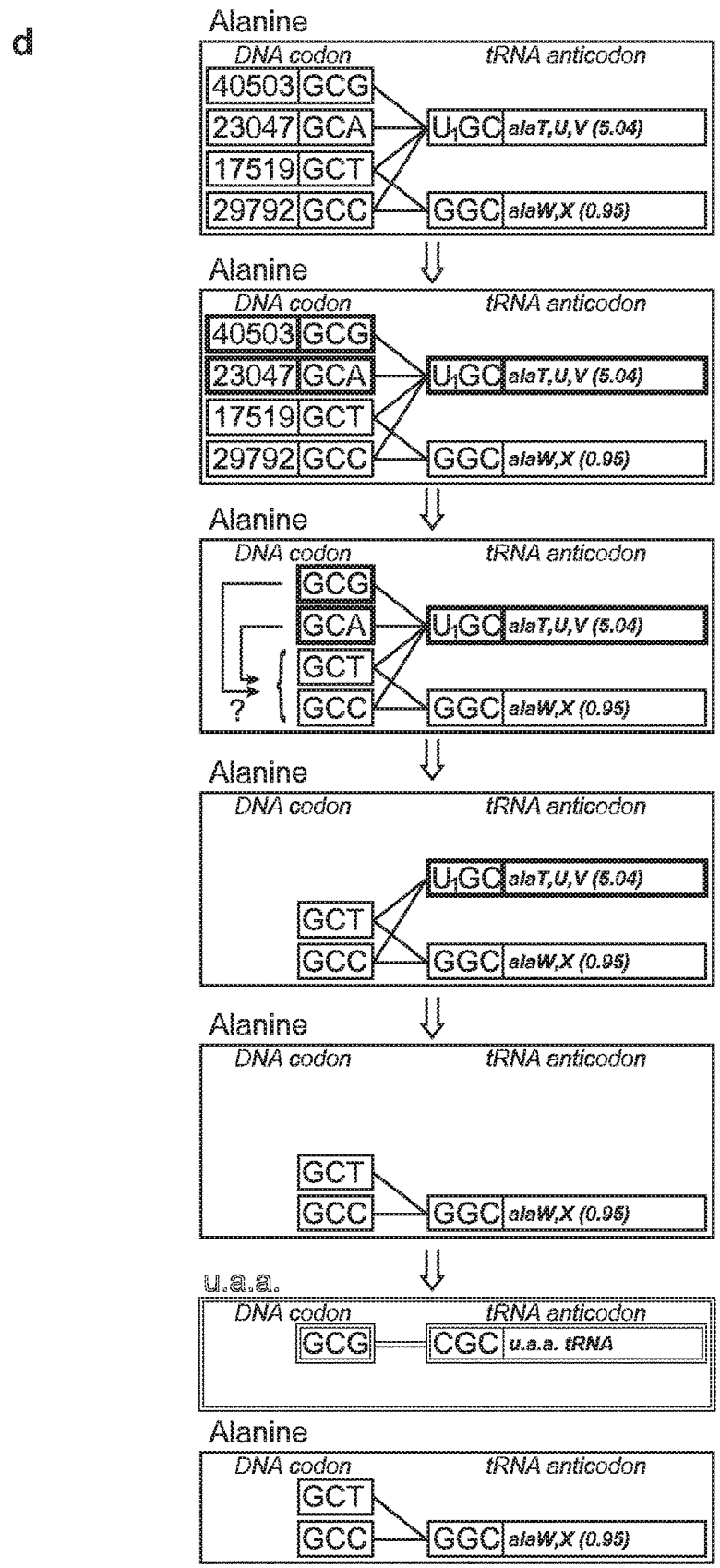

FIGURE 16 (extended data figure 8)
a
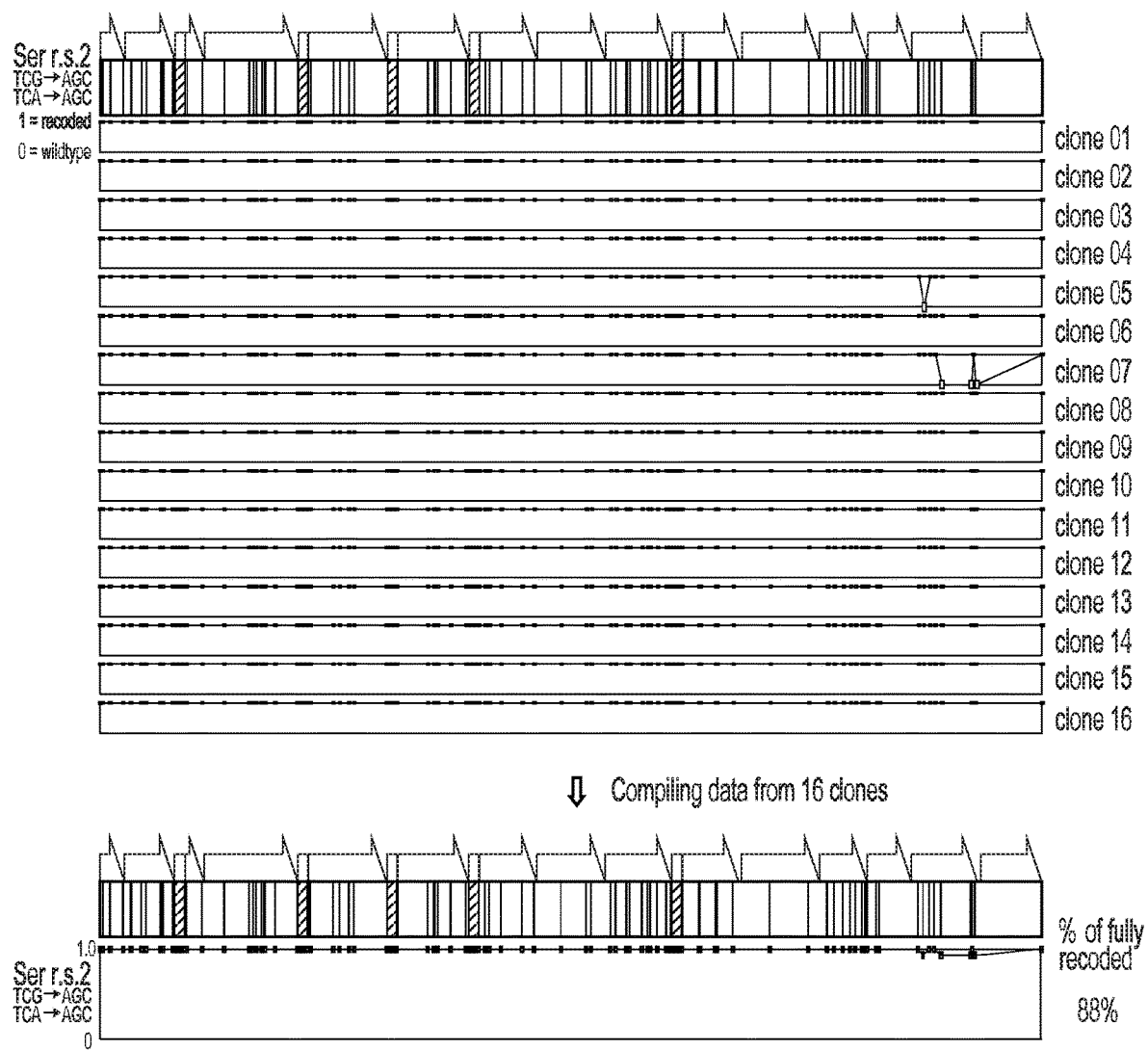

FIGURE 16 (extended data figure 8) continued
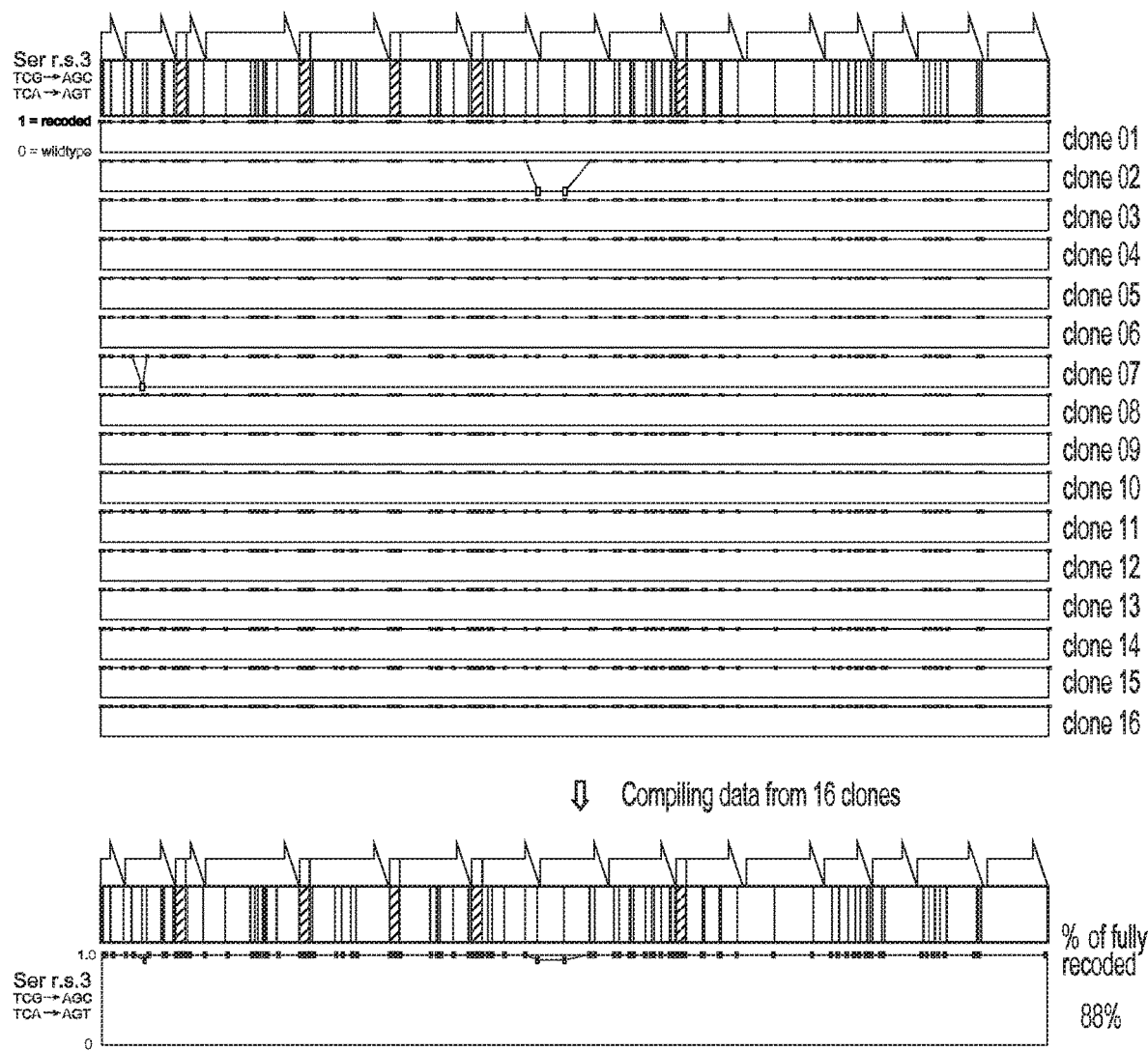

FIGURE 16 (extended data figure 8) continued
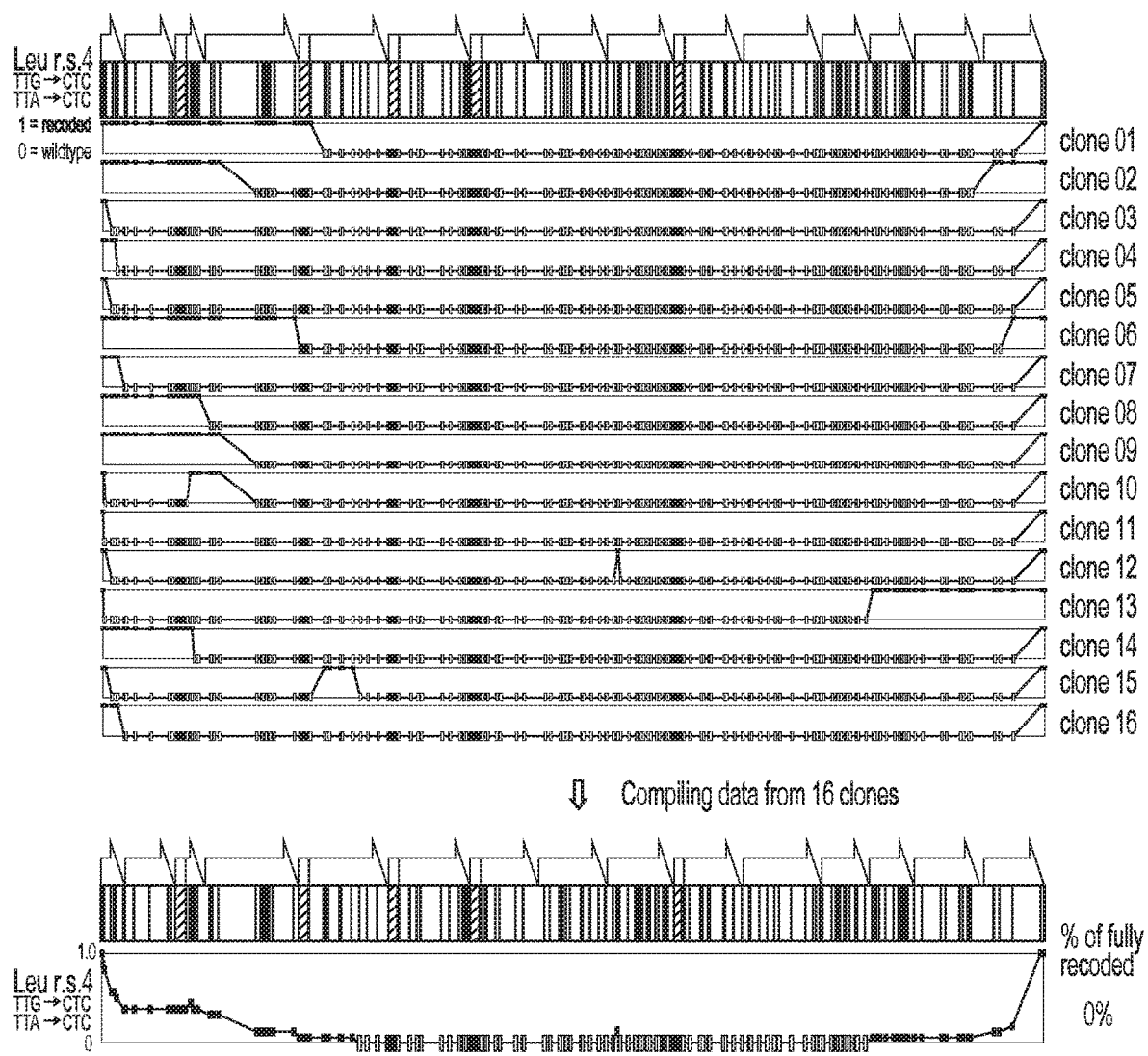

FIGURE 16 (extended data figure 8) continued
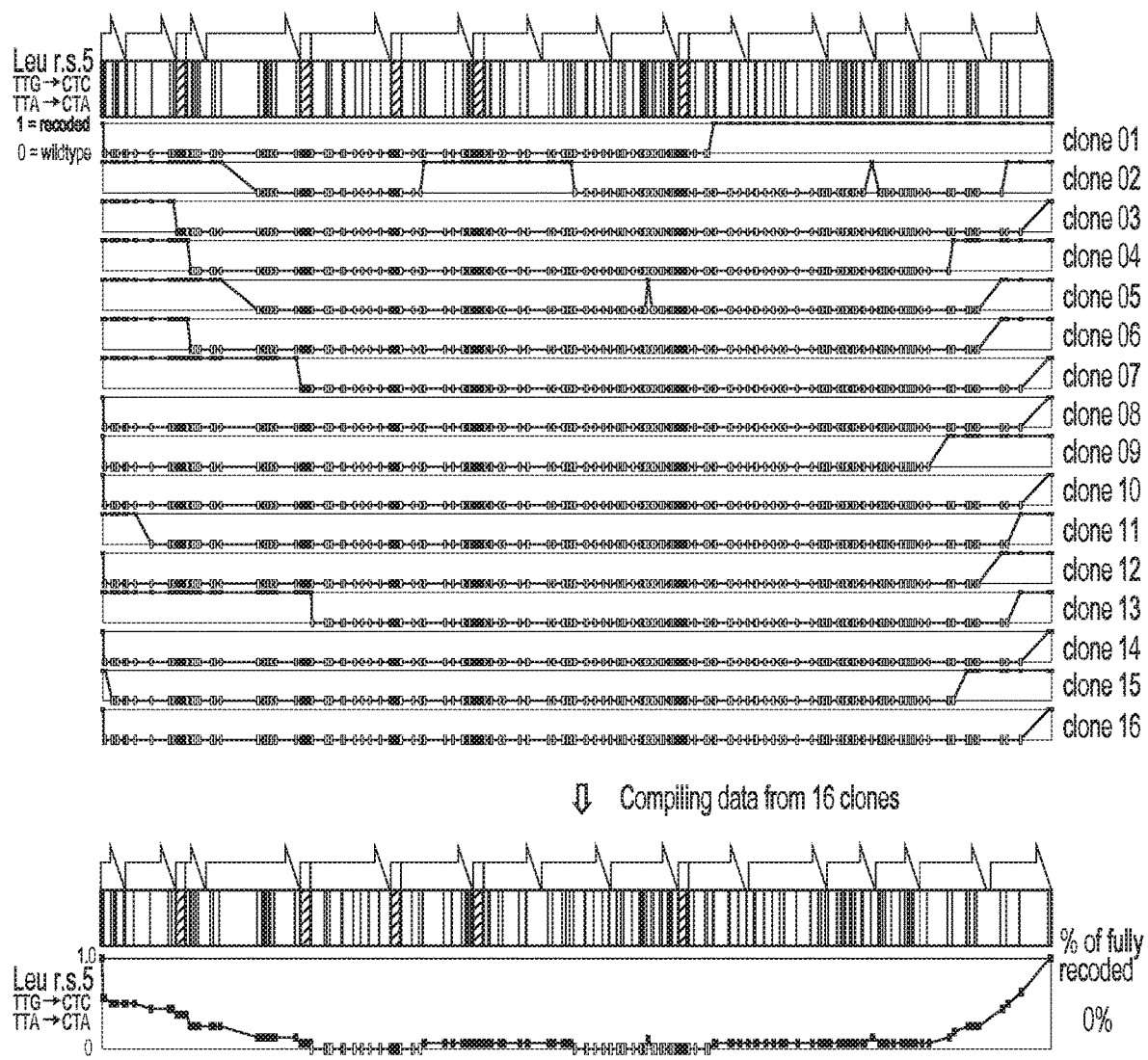

FIGURE 16 (extended data figure 8) continued
e
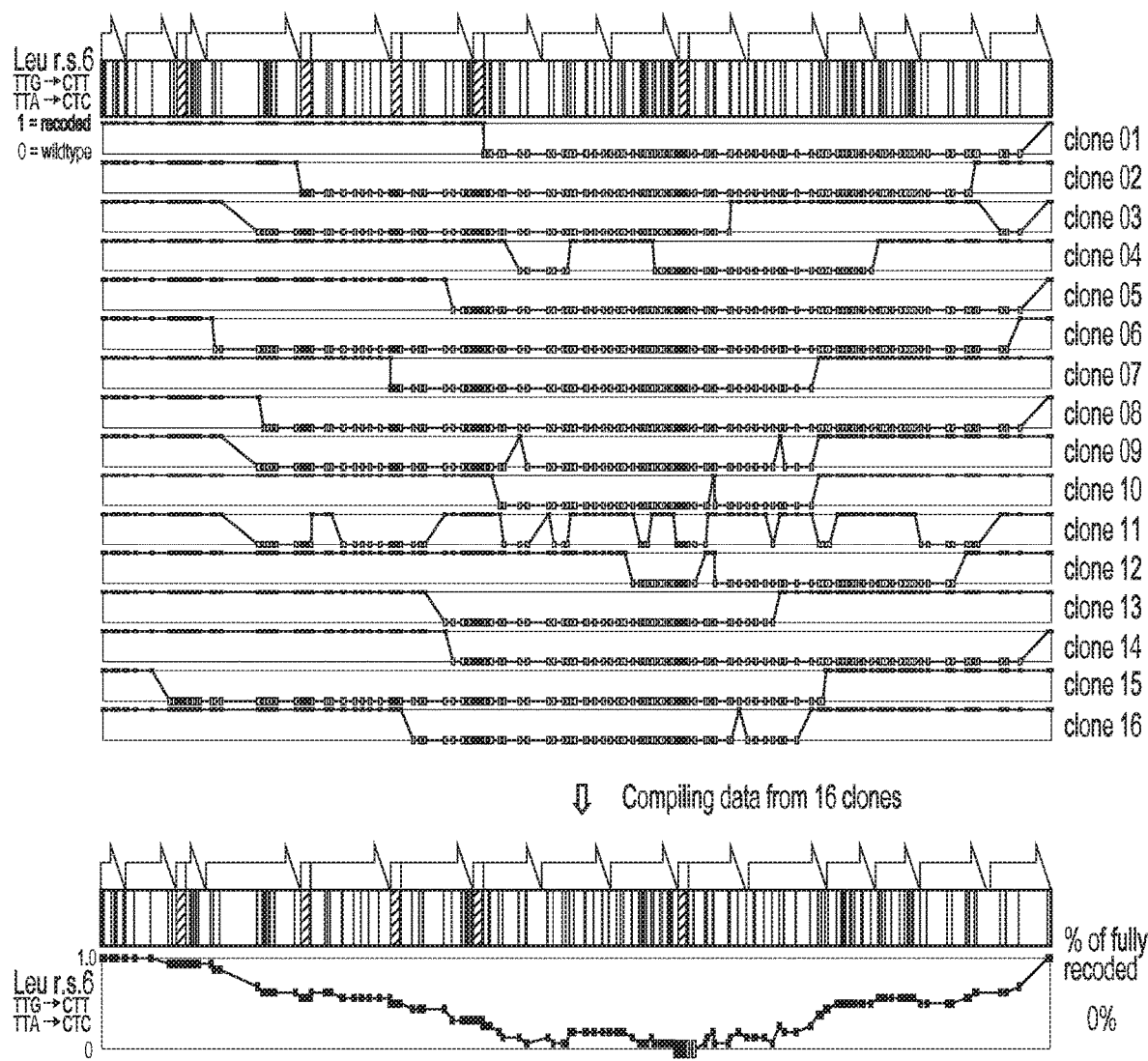

FIGURE 16 (extended data figure 8) continued
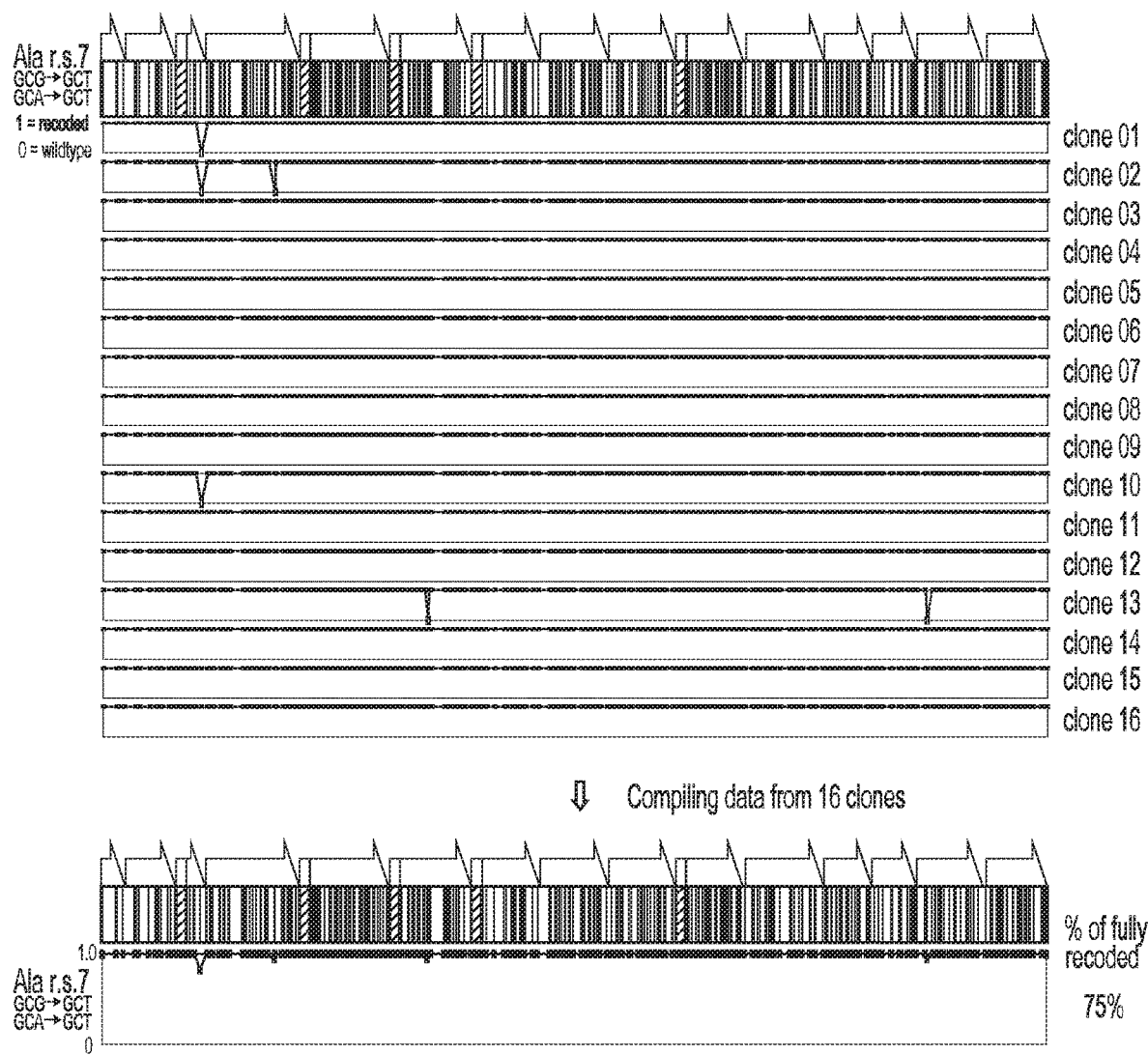

FIGURE 16 (extended data figure 8) continued
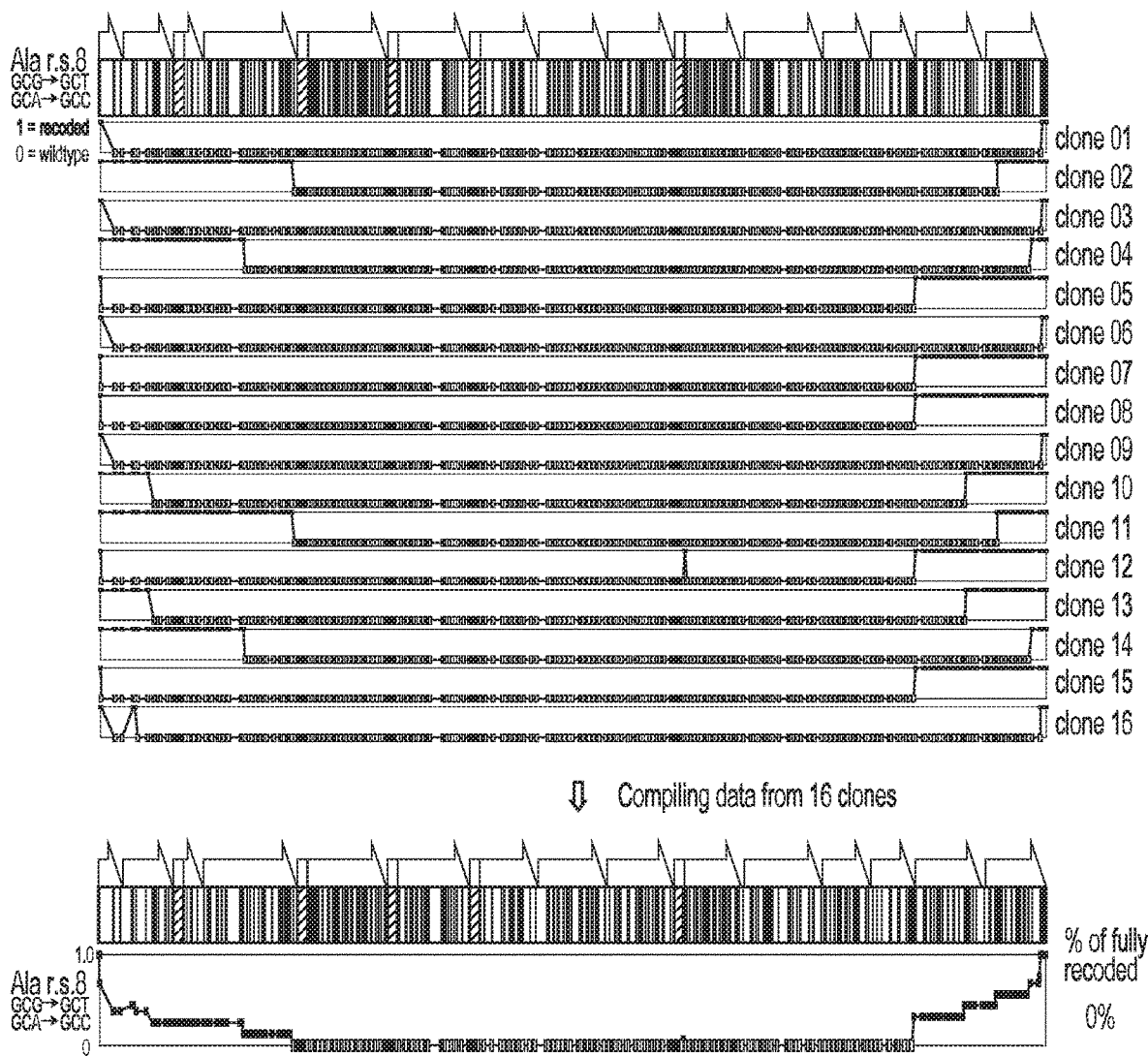

FIGURE 16 (extended data figure 8) continued
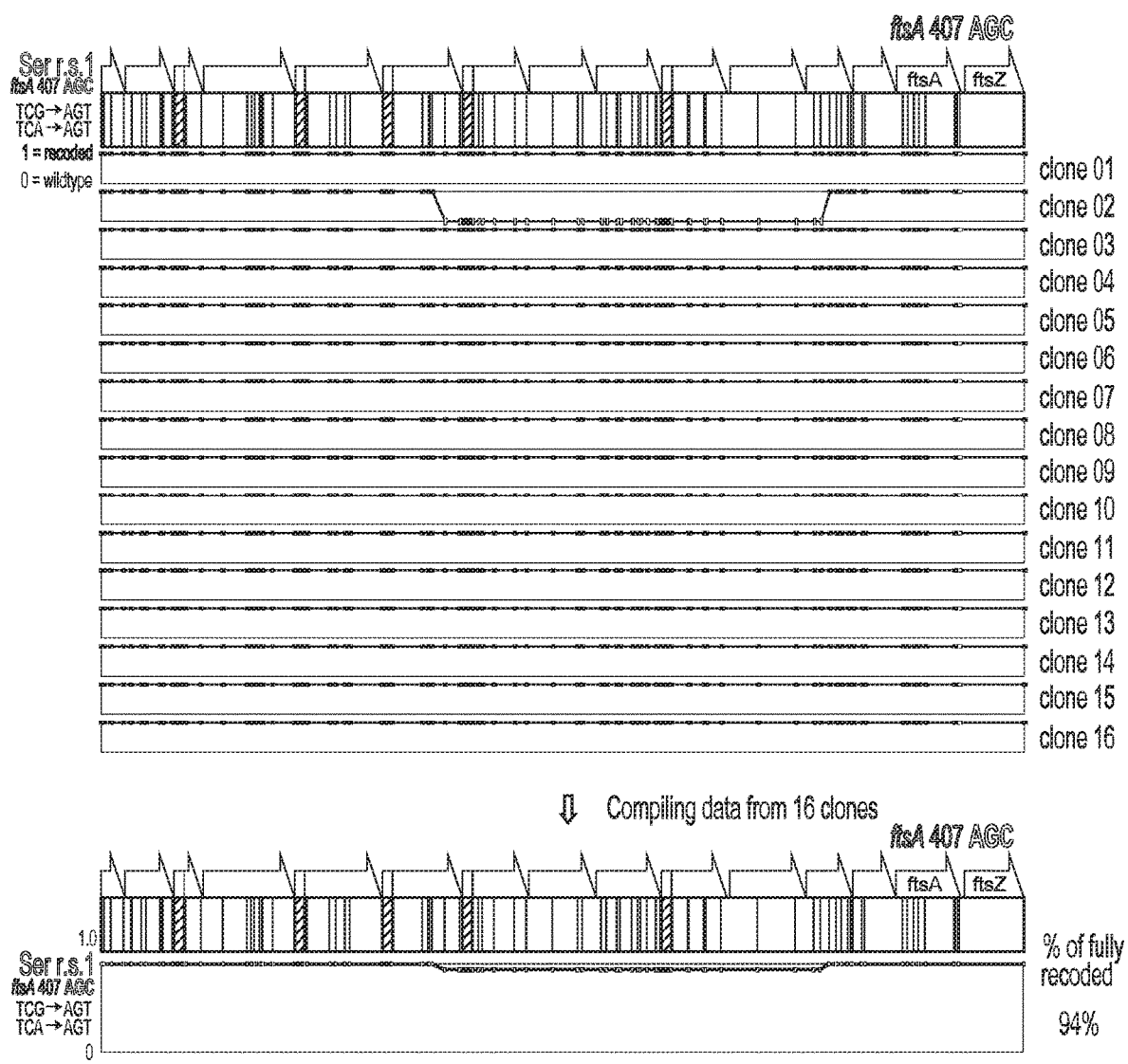

KAISER 4p

-1: *rpsL*  +1: $Kan^R$  Ori1: p15A
-2: *sacB*  +2: $Cm^R$  Ori2: pRSF
            +3: $Amp^R$ / $Tet^R$ / $Erm^R$ / $Hy^R$

GENOME EDITING

CROSS-REFERENCE TO RELATED APPLICATIONS

This application is a national stage under 35 U.S.C. 371 of International Application No. PCT/GB2017/052188, filed Jul. 27, 2017 (currently published). International Application No. PCT/GB2017/052188 cites the priority of UK Application No. 1613135.1, filed Jul. 29, 2016 (expired).

SEQUENCE LISTING

The instant application contains a Sequence Listing which has been submitted electronically in ASCII format and is hereby incorporated by reference in its entirety. Said ASCII copy, created on Jul. 29, 2016 is named P10377WO_ST25.txt and is 16.449 bytes in size.

FIELD OF THE INVENTION

The invention is in the field of genetics, in particular the efficient manipulation and creation of useful recombinant nucleic acids.

BACKGROUND TO THE INVENTION

The de novo design and synthesis of genomes provides powerful approaches for understanding and engineering biology. Genome synthesis has the potential to accelerate investigations into the role of synonymous codons, accelerate metabolic engineering by allowing the introduction of genes encoding heterologous pathways into the genome, facilitate the reassignment of sense codons to new monomers for unnatural polymer synthesis, and potentially improve the biosafety of organisms.

In vitro synthesis of a *Mycoplasma mycoides* genome and nuclear transfer into *M. capricolum* has been achieved in the prior art. In more detail, a complete synthetic genome has been produced. This introduced a synthetic genome of *Mycoplasma mycoides* into a host *Mycoplasma capricolum*. For example, this is described in Gibson et al 2010 (Science Vol. 329, Issue 5987, pp. 52-56 “Creation of a Bacterial Cell Controlled by a Chemically Synthesized Genome”). This was an extremely laborious procedure taking almost ten years to complete. This is a problem in the art.

A challenge with extending this approach for the radical redesign of genomes is that the sequence of the synthetic genome must be tolerated in its entirety, or genome replacement does not take place.

Methods that allow iterative site directed mutagenesis of the genome have been developed, and used to edit 321 TAG codons in *Escherichia coli* to TAA, but require a strain deficient in a DNA repair pathway to facilitate mutagenesis, and the targeted mutations were accompanied by a greater number (355) of off target mutations, which is clearly a problem.

Moreover, site directed mutagenesis based approaches cannot introduce large insertions, and will be increasingly cumbersome to implement as the density and/or number of alterations desired in the genome increases, which is a drawback with prior art methods.

Genome synthesis has the potential to radically alter the genome through the introduction of large insertions and deletions into the genome, and to introduce any density and/or number of mutations. However, methods that replace the genome in sections, as recently reported for *Saccharomyces cerevisiae*6, and that provide feedback on precisely where a given design fails, are required to accelerate our ability to manipulate and understand the information encoded in genomes.

It is a problem in the art that transformation efficiency can be a limiting step in nucleic manipulation. This is especially true as sizes increase from 2 kb to 9 kb and higher. Transformation efficiency of linear DNA in excess of 9 kb can pose a severe restriction on the efficiency of nucleic acid manipulations relying on such a step.

It is a problem in the art that only a few kb of nucleic acid per round can be manipulated using known techniques.

It is a problem in the art that low efficiency of recombination and/or recombination at inappropriate locations within the target nucleic acid can seriously hinder nucleic acid manipulations within the prior art.

CRISPR-Cas systems are disclosed in Jiang et al 2013 (Jiang. W., Cox, D., Zhang. F., Bikard, D. & Marraffini. L. A. RNA-guided editing of bacterial genomes using CRISPR-Cas systems. Nature Biotechnology 31, 233-239 (2013)). In this paper, the focus is on trying to edit multiple defined codons (3 bp for each codon) by using single strand DNA (ssDNA) mediated recombineering and eliminating un-edited cells by cutting with CRISPR/Cas9 at these multiple positions. The authors try to change precisely at the cutting sites on the genome. Jiang et al do not use an episomal replicon to deliver their donor nucleic acid. They use single strand DNA and introduce the change by ssDNA recombineering, which fundamentally limits the length of change to a few nucleotides, which is a problem.

Traver et al 2009 (Traver, B. E., Anderson. M. A. E. & Adelman, Z. N. Homing endonucleases catalyze double-stranded DNA breaks and somatic transgene excision in *Aedes aegypti*. *Insect Molecular Biology* 18, 623-633 (2009) disclose “double cut” of the genome by homing nuclease to delete or excise the genomic sequence between the two cut sites in mosquitos. Traver et al describe a eukaryote (mosquitos) system. Traver et al describe a deletion, but not any insertion nor any replacement. Traver et al do not provide donor DNA such as synthetic DNA. Traver et al are intrinsically limited by the position of the endonucleases to do the excision, which is also a drawback.

The creation of synthetic genomes in cells is limited by the inefficient in vivo replacement of natural genomic DNA with synthetic DNA.

In *E. coli*, short regions of synthetic DNA may be inserted into the genome or used to replace genomic DNA in a two-step process: i) transformation of cells with linear double stranded DNA (dsDNA) carrying a stretch of synthetic DNA, coupled with a positive selection marker, and flanked by a homology region (HR) to the target region of the genome on each end, and ii) recombination mediated by the homologous regions, followed by selection for genomic integration by virtue of the positive selection marker. This approach (‘classical recombination’, exemplified by lambda red mediated recombination in *E. coli*) does not always lead to integration at the target locus, due to the limited specificity conferred by HRs. Moreover, classical recombination is commonly used to insert or replace only 2-3 kb of genomic DNA, because i) it is difficult to prepare sufficient quantities of intact, un-sheared, long linear dsDNA free from errors, and ii) the efficiency of the process drops off rapidly with the length of DNA inserted. Thus, while large regions of genomes can be deleted and a minimal genome strain of *E. coli* (MDS42) has been created, no methods to introduce long synthetic DNA into the genome as insertions or replacements have been reported.

Sakura et al 2016 (Sakura, Nakade, Sakane. Suzuki amd Yamamoto Nat Protoc. 2016 January; 11(1):118-33) disclose MMEJ-assisted gene knock-in using TALENs and CRISPR-Cas9 with the PITCh systems. This document discloses a process for making 'knock-in' HEK293T cells and frog embryos. Sakura et al do not use an episomal replicon. The circular vector introduced by Sakura et al cannot replicate in the host they used and thus will be very quickly lost through cell division.

The present invention seeks to overcome problem(s) associated with the prior art.

SUMMARY OF TIE INVENTION

Here we report a method for single step insertion of 90 kb of synthetic DNA into the *E. coli* genome, and single step replacement of 100 kb of the *E. coli* genome with synthetic DNA, and demonstrate that the method may be iterated. We use our approach to synthesize a 20 kb region of the *E. coli* genome that is rich in essential genes using well-defined synonymous recoding rules. Our results reveal defined synonymous recoding rules that are tolerated simultaneously across numerous essential genes. The method is flexible and has the technical benefit that it can introduce or replace more than 100 Kb of nucleic acid in a target nucleic acid in a single round.

Thus in one aspect, the invention relates to a method comprising
a) providing a host cell
said host cell comprising an episomal replicon,
said episomal replicon comprising a donor nucleic acid sequence.
said host cell further comprising a target nucleic acid,
b) providing helper protein(s) capable of supporting nucleic acid recombination in said host cell
c) providing helper protein(s) and/or RNAs capable of supporting nucleic acid excision in said host cell
wherein said donor nucleic acid sequence comprises in order: 5'-homologous recombination sequence 1-sequence of interest-homologous recombination sequence 2-3'
wherein said sequence of interest comprises a positive selectable marker
d) inducing excision of said donor nucleic acid sequence
e) incubating to allow recombination between the excised donor nucleic acid and said target nucleic acid
f) selecting for recombinants having incorporated said donor nucleic acid into said target nucleic acid.

Suitably said target nucleic acid comprises in order: 5'-homologous recombination sequence 1-negative selectable marker-homologous recombination sequence 2-3'.

Suitably selecting for recombinants having incorporated said donor nucleic acid into said target nucleic acid comprises selection for gain of the positive selectable marker of the donor nucleic acid and loss of the negative selectable marker of the target nucleic acid.

Suitably selection for gain of the positive selectable marker of the donor nucleic acid and loss of the negative selectable marker of the target nucleic acid is carried out simultaneously.

Suitably said sequence of interest comprises both a positive selectable marker and a negative selectable marker.

Suitably said method as described above further comprises the step of
dii) inducing at least one double stranded break in the target nucleic acid sequence, wherein said double stranded break is between said homologous recombination sequence 1 and said homologous recombination sequence 2.

Suitably at least two double stranded breaks are induced in the target nucleic acid sequence, wherein each said double stranded break is between said homologous recombination sequence 1 and said homologous recombination sequence 2.

Suitably said excised donor nucleic acid begins with said homologous recombination sequence 1 and ends with said homologous recombination sequence 2.

Suitably said episomal replicon comprises a negative selectable marker independent of the donor nucleic acid sequence.

Suitably said method comprises the further step of selecting for loss of the episomal replicon by selecting for loss of said negative selectable marker independent of the donor nucleic acid sequence.

Suitably said episomal replicon comprises in order: excision cut site 1-donor nucleic acid sequence-excision cut site 2.

Suitably said target nucleic acid possesses its own origin of replication capable of functioning within said host cell.

Suitably said episomal replicon is a plasmid nucleic acid.

Suitably said target nucleic acid is a plasmid nucleic acid.

Suitably said episomal replicon is a first plasmid nucleic acid and said target nucleic acid is a second plasmid nucleic acid.

Suitably said episomal replicon is a bacterial artificial chromosome (BAC).

Suitably said target nucleic acid is a bacterial artificial chromosome (BAC).

Suitably said episomal replicon is a first bacterial artificial chromosome (BAC) and said target nucleic acid is a second bacterial artificial chromosome (BAC).

Suitably said target nucleic acid is the host cell genome.

Suitably the negative selectable marker is selected from the group consisting of sacB (sucrose sensitivity) or rpsL (S12 ribosomal protein-streptomycin sensitivity).

Suitably the positive selectable marker is selected from the group consisting of CmR (chloramphenicol resistance) or KanR (kanamycin resistance).

Suitably the step of selecting for recombinants comprises sequential selection for said positive and negative markers, or sequential selection for said negative and positive markers.

Suitably the step of selecting for recombinants comprises simultaneous selection for said positive and negative markers.

Suitably said helper protein(s) and/or RNAs capable of supporting nucleic acid excision comprise CRISPR/Cas9 proteins/RNAs.

Suitably said helper protein(s) capable of supporting nucleic acid recombination comprise lambda Red proteins.

In another aspect, the invention relates to a method of assembling a synthetic genome, the method comprising performing the steps as described above with a first donor nucleic acid sequence, choosing further donor sequence(s) contiguous with said first donor nucleic acid sequence, and repeating said steps with said further donor nucleic acid sequence(s) until the synthetic genome has been assembled.

In another aspect, the invention relates to a recombinant nucleic acid obtained according to a method as described above.

In another aspect, the invention relates to a host cell comprising recombinant nucleic acid as described above.

DOSER refers to a combinatorial selection approach involving a positive marker and loss of a negative marker. Use of this "double selection" scheme actually also helps with site specificity. For example, if a recombination event takes place at an inappropriate site, it could result in acquisition of the positive selectable marker. However, by using simultaneous selection for the positive marker and loss of the negative marker, even if the nucleic acid has been incorporated into the target nucleic acid at an inappropriate site (thereby conferring the positive marker), such molecules still would not be selected because if they have recombined into an inappropriate site they will not have simultaneously resulted in the loss of the negative marker. Therefore, as well as being a useful selection in its own right, this actually adds to the technical benefit of assisting in the site specificity by selecting not only for acquisition of the donor sequence but also simultaneous deletion of the sequence being removed/replaced.

Recombination may happen instantly or very quickly. Thus the step of incubating to allow recombination between the excised donor nucleic acid and said target nucleic acid may be short. A typical example is 5 hours incubation (e.g. for REXER/KAISER protocols), which advantageously allows dilution of the negative selection marker through protein degradation and/or cell division including the time needed for recombination.

DETAILED DESCRIPTION OF THE INVENTION

Here we report efficient length independent insertion, and replacement of *E. coli* genomic DNA with synthetic DNA, triggered by programmed in vivo excision of double stranded DNA from an episomal replicon by CRISPR/Cas9. We demonstrate the insertion of 90 kb of synthetic DNA into the genome, the replacement of 100 kb of genomic DNA with synthetic DNA, and iteration of the approach which will enable stepwise genome resynthesis. We use our approach to simultaneously recode 15 genes, including 12 essential genes, using well-defined synonymous recoding schemes that introduce 723 programmed mutations across the targeted genomic region. This approach pinpoints modes of failure for unsuccessful recoding schemes and enables the identification of successful synonymous recoding schemes in the cell. The choice of codon is important in controlling protein expression, folding, and mRNA structure. Our results show that despite the combinatorial impossibility of sampling all synonymously recoded genomes, it is possible to design synonymous recoding schemes that work at many positions in essential genes in the genome.

In brief, the KAISER 2 approach involves introduction of the episomal replicon such as a BAC, incubation to expand the population of cells carrying the episomal replicon, excision of the donor sequence in vivo, incubation to allow recombination, and the selection for the gain/loss of the appropriate selectable markers.

In brief, KAISER 4 follows the same procedure as KAISER 2 but in addition introduces cut(s) (double stranded DNA break(s)) into the target nucleic acid into which the donor nucleic acid (such as synthetic nucleic acid) is to be recombined.

It should be noted that double stranded breaks do not repair in *E. coli*. By "do not repair" it is meant that repair of double stranded breaks is an extremely rare event. This is because double stranded breaks in *E. coli* cannot be rejoined spontaneously. The only way to repair double stranded breaks in *E. coli* is by recombination.

Moreover, the host organism such as *E. coli* may be chosen, or may be manipulated, in order to inhibit naturally occurring repair mechanisms to ensure the absence of, or extremely low likelihood of, double stranded repair. For example, the RecBCD system may be mutated or inhibited provided that suitable helper protein(s) capable of supporting nucleic acid recombination in the host cell are present in place of RecBCD, e.g. the lambda Red proteins described herein or other suitable recombination support proteins. For example, in one embodiment RecBCD may be inhibited in our KAISER protocol because it can interfere with lambda red components and reduce the efficiency of recombination using double strand DNA with short homology regions (e.g. around 50 bp)(degraded by RecBCD system) carried out by lambda red components. However, if long homology regions (e.g. around 3-5 kb) are used, RecBCD can be an alternative as recombination support protein(s) to lambda red components as recombination support protein(s).

Some of these effects are illustrated for example with reference to FIG. 2f which shows a greatly enhanced efficiency using the KAISER 4 scheme compared to the KAISER 2 scheme.

Of course it would be apparent to the skilled worker that only a single event is actually required in order to obtain the altered nucleic acid being produced. However, enhanced efficiency as evidenced by FIG. 2f is extremely beneficial and also allows inferences to be made, for example if no successful altered nucleic acids are obtained it strongly infers that the synthetic sequence being introduced is deleterious or toxic to the host cell. With low efficiency systems, a failure to obtain the desired nucleic acid might merely indicate a failure in the system, whereas it is an advantage of the invention that the high efficiency obtained allows meaningful inferences to be drawn if no altered nucleic acid product is ultimately produced.

It should be noted that prior art approaches to altering nucleic acids may have involved the making of a double stranded break in the target sequence. For example, classical CRISPR/Cas9 involves introductions of a short synthetic DNA in selection against non-recombinant nucleic acids by using CRISPR/Cas9 in order to cut the target sequences which have not recombined with the synthetic sequence being introduced. However, in contrast to the present invention, prior art approaches have typically carried out the CRISPR/Cas9 cutting event after the recombination has already taken place. To the best of the inventors' knowledge there is no relevant prior disclosure of any system cutting the target sequence before the recombination event as in the present invention. Suitably the excision/cutting step(s) of the invention are carried out before the recombination step(s) during a single cycle of the method of the invention. Suitably no excision/cutting step(s) of the invention are carried out after the recombination step(s) during a single cycle of the method of the invention.

Without wishing to be bound by theory, early research in nucleic acid recombination advanced two theories—firstly that a double stranded break might increase recombination events, and secondly that a double stranded break was independent of recombination events. Current thinking in the art is that recombination is independent of double stranded breaks. The view in the art is that double stranded breaks do not necessarily lead to an increase in recombination.

It is very surprising that the methods of the invention are effective. For example, the theoretical understanding of the lambda Red recombination system is that it operates via a single stranded (ssDNA) stage. Therefore, every expectation is that this system should be limited to maximally a few kb replacement/insertion synthetic nucleotide sequence. However, very surprisingly, this limit is simply not observed in the methods of the present invention.

Definitions

A plasmid means a small circular nucleic acid (usually DNA, most usually double-stranded DNA) molecule. A plasmid within a cell is physically separated from any chromosomal nucleic acid such as DNA and can replicate independently. Considering plasmids, 'small' means they are typically no bigger than 10 kb. Suitably a plasmid useful in the invention has the following genetic elements: an origin of replication cognate for the host cell; and at least one selection marker.

A BAC means a bacterial artificial chromosome. Suitably a BAC has the following genetic elements: an origin of replication cognate for the host cell; and at least one selection marker.

A YAC means a yeast artificial chromosome. Suitably a YAC has the following genetic elements: an origin of replication cognate for the host cell; and at least one selection marker.

BACs and plasmids differ from each other by their replication origin. A BAC has a special replication origin which typically makes the BAC a single copy in each cell and helps the BAC to maintain a bigger size (up to several hundred kb). Plasmids have a plasmid replication origin which typically makes the plasmid multiple copies (ranging from a few copies to a few hundred copies per cell) in each cell and typically of a size up to around 10 kb.

The nucleic acid herein is suitably DNA.

Homologous Recombination

In theory any nucleotide sequence can be chosen as the site for homologous recombination sequences.

Suitably the nucleotide sequence for homologous recombination is unique. Suitably unique means unique within the target sequence into which the donor sequence is being recombined.

Suitably the sequence for homologous recombination is non-repetitive.

Suitably the sequence for homologous recombination is at least 30 nucleotides long. Homologous recombination sequences as short as 30 nucleotides may lead to a low efficiency; thus for high efficiency suitably the homologous recombination sequence is at least 40 nucleotides in length, suitably at least 50 nucleotides, suitably 50 to 100 nucleotides, most suitably 50 to 65 nucleotides.

The sequence for homologous recombination is selected on the target sequence and introduced into the donor sequence. Therefore the HR1 and HR2 on the donor sequence show 100% sequence identity to the HR1 and HR2 on the target sequence.

Use of lambda Red recombination permits short nucleotide sequences to be used for homologous recombination, as outlined above. Other recombination support systems may be used. For example, the RecBCD system might be used. When the RecBCD system is used, suitably the step of "providing helper protein(s) capable of supporting nucleic acid recombination in said host cell" consists of inducing or permitting expression of the RecBCD system within the host cell.

When using the RecBCD system or other recombination support systems, the skilled operator will pay attention to the requirements of those systems on the sequences selected for homologous recombination. For example, the RecBCD system may require longer homologous recombination sequences such as 3 to 10 kb in length.

In more detail, RecBCD is a natural *E. coli* recombination system consisting of three components RecB, RecC, and RecD. The three subunits make up an ATP-dependent helicase/nuclease complex that is essential for both homologous recombination during the course of transduction and conjugation as well as in repair of double-strand breaks in *E. coli*. Studies in which double strand breaks are induced in vivo in *E. coli* DNA show that double-strand break repair (DSBR) can proceed via one of two recombination pathways. Both pathways require RecBCD and RecA, but one depends on the resolvase enzyme, RuvABC, while the other does not and instead relies on RecG. The recB and recD genes form an operon while recC is situated nearby but has its own promoter. The three gene products form a heterotrimer which is also known as Exonuclease V. In case any further guidance is needed, details can be found in the publically available EcoCyc database under 'RecBCD', for example for the K12-MG-1655 strain of *E. coli* (Keseler et al. (2013), "EcoCyc: fusing model organism databases with systems biology". Nucleic Acids Research 41: D605-12).

Thus to support recombination as required by the invention, at least RecBCD should be expressed in the host cell.

It may be that RecA is also required: thus, more suitably to support recombination as required by the invention, at least RecBCD and RecA should be expressed in the host cell. Most suitably to support recombination as required by the invention, RecBCD and RecA should be expressed in the host cell.

Another alternative to the lambda red system is the RecET system. RecE and RecT are *E. coli* genes of phage origin. RecE mimics lambda red alpha, and RecT mimics lambda red beta (Muyrers, J. P., Zhang, Y., Buchholz, F. & Stewart, A. F. RecE/RecT and Redalpha/Redbeta initiate double-stranded break repair by specifically interacting with their respective partners. Genes Dev. 14, 1971-1982 (2000)). The RecET combination performs comparatively to lambda red alpha/beta combination. Lambda red alpha and beta are the actual components that carry out recombination, while lambda red gamma is an inhibitor of the RecBCD system.

Suitably recombination support is provided via the lambda red system, for example from the commercially available pRed/ET plasmid from Gene Bridges ("Quick & Easy *E. coli* Gene Deletion Kit" from Gene Bridges GmbH. Im Neucnheimer Feld 584.69120 Heidelberg, Germany.).

This system in this setup is first described in Datsenko et al 2000 (Datsenko K. A. & Wanner. B. L. One-step inactivation of chromosomal genes in *Escherichia coli* K-12 using PCR products. Proc. Natl. Acad. Sci. U.S.A. 97, 6640-6645 (2000)), which is hereby incorporated herein by reference specifically for details of the Lambda Red system.

The inventors teach that the pRed/ET plasmid is based on the pKD46 plasmid in Datsenko et al 2000 (as judged by sequence identity), and therefore the pKD46 plasmid may be used as a template to perform PCR for the construction of lambda red system.

When said helper protein(s) capable of supporting nucleic acid recombination comprise lambda Red proteins, suitably the following proteins are expressed in said host cell:

TABLE 1

| Lambda Red protein | Essential? | Function/notes | Exemplary sequence/accession number |
|---|---|---|---|
| alpha | essential | SEQ ID NO: 1 lambda red recombination | ATGACACCGGACATTATCCTGCAGCGTACCGGGATCG ATGTGAGAGCTGTCGAACAGGGGGATGATGCGTGGCA CAAATTACGGCTCGGCGTCATCACCGCTTCAGAAGTT CACAACGTGATAGCAAAACCCCGCTCCGGAAAGAAGT GGCCTGACATGAAAATGTCCTACTTTCACACCCTGCT TGCTGAGGTTTGCACCGGTGTGGCTCCGGAAGTTAAC GCTAAAGCACTGGCCTGGGGAAAACAGTACGAGAACG ACGCCAGAACCCTGTTTGAATTCACTTCCGGCGTGAA TGTTACTGAATCCCCGATCATCTATCGCGACGAAAGT ATGCGTACCGCCTGCTCTCCCGATGGTTTATGCAGTG ACGGCAACGGCCTTGAACTGAAATGCCCGTTTACCTc ccgggATTTCATGAAGTTCCGGCTCGGTGGTTTCGAG GCCATAAAGTCAGCTTACATGGCCCAGGTGCAGTACA GCATGTGGGTGACGCGAAAAAATGCCTGGTACTTTGC CAACTATGACCCGCGTATGAAGCGTGAAGGCCTGCAT TATGTCGTGATTGAGCGGGATGAAAAGTACATGGCGA GTTTTGACGAGATCGTGCCGGAGTTCATCGAAAAAAT GGACGAGGCACTGGCTGAAATTGGTTTTGTATTTGGG GAGCAATGGCGATAG |
| beta | essential | SEQ ID NO: 2 lambda red recombination | ATGAGTACTGCACTCGCAACGCTGGCTGGGAAGCTGG CTGAACGTGTCGGCATGGATTCTGTCGACCCACAGGA ACTGATCACCACTCTTCGCCAGACGGCATTTAAAGGT GATGCCAGCGATGCGCAGTTCATCGCATTACTGATCG TTGCCAACCAGTACGGCCTTAATCCGTGGACGAAAGA AATTTACGCCTTTCCTGATAAGCAGAATGGCATCGTT CCGGTGGTGGGCGTTGATGGCTGGTCCCGCATCATCA ATGAAAACCAGCAGTTTGATGGCATGGACTTTGAGCA GGACAATGAATCCtgtacaTGCCGGATTTACCGCAAG GACCGTAATCATCCGATCTGCGTTACCGAATGGATGG ATGAATGCCGCCGCGAACCATTCAAAACTCGCGAAGG CAGAGAAATCACGGGCCGTGGCAGTCGCATCCCAAA CGGATGTTACGTCATAAAGCCATGATTCAGTGTGCCC GTCTGGCCTTCGGATTTGCTGGTATCTATGACAAGGA TGAAGCCGAGCGCATTGTCGAAAATACTGCATACACT GCAGAACGTCAGCCGGAACGCGACATCACTCCGGTTA ACGATGAAACCATGCAGGAGATTAACACTCTGCTGAT CGCCCTGGATAAAACATGGGATGACGACTTATTGCCG CTCTGTTCCCAGATATTTCGCCGCGACATTCGTGCAT CGTCAGAACTGACACAGGCCGAAGCAGTAAAAGCTCT TGGATTCCTGAAACAGAAAGCCGCAGAGCAGAAGGTG GCAGCATGA |
| gamma | | SEQ ID NO: 3 inhibiting RecBCD | ATGGATATTAATACTGAAACTGAGATCAAGCAAAAGC ATTCACTAACCCCCTTTCCTGTTTTCCTAATCAGCCC GGCATTTCGCGGGCGATATTTTCACAGCTATTTCAGG AGTTCAGCCATGAACGCTTATTACATTCAGGATCGTC TTGAGGCTCAGAGCTGGGCGCGTCACTACCAGCAGCT CGCCCGTGAAGAGAAAGAGGCAGAACTGGCAGACGAC ATGGAAAAAGGCCTGCCCCAGCACCTGTTTGAATCGC TATGCATCGATCATTTGCAACGCCACGGGGCCAGCAA AAAATCCATTACCCGTGCGTTTGATGACGATGTTGAG TTTCAGGAGCGCATGGCAGAACACATCCGGTACATGG TTGAAACCATTGCTCACCACCAGGTTGATATTGATTC AGAGGTATAA |

Homologous Recombination Sequences

In order to choose a homologous recombination sequence, the following steps may be used:
Choose 50 to 100 nucleotides in the desired position in the sequence of the nucleic acid being altered (target nucleic acid) such as a bacterial genome or plasmid backbone.
Perform a BLAST search of the chosen sequence against the target nucleic acid.
Consider the E-value for the chosen sequence compared to the closest match in the BLAST search—typically an E-value compared to an undesired target site elsewhere in the target nucleic acid of greater than $10^{-20}$ would be too high; if this is discovered then suitably an alternate homologous recombination sequence is selected.

Suitably standard BLAST tool is used to calculate the E-value for HR sequences. One such online tool is BioCyc BLAST (biocyc.org). Suitably the focus is on how unique a given HR sequence is as judged by E-value. Suitably it is not necessary to consider/calculate affinity. In principle any sequence that can work with classical recombination, is going to work better with the invention e.g. KAISER.

In more detail, if HR sequences can work with classical recombination, they are going to work better in the invention. Suitably the HR sequences for the invention are selected following the exact principle and requirement as for classical recombination using lambda red system. For example, we typically design HRs 50-70 bp in length and blast against E. coli genome for an expected value lower than $10^{-20}$. (E-value, a measurement of how unique a given sequence is: the lower the E-value is, the more unique the sequence is. Any suitable tool for calculation may be used, for example standard BLAST tool to calculate the E-value for HR sequences. One such online tool is BioCyc BLAST (biocyc.org). Values lower than $10^{-20}$ E-value are not expected to be necessary, although of course sequences with lower values are still useful in the invention.

The E-value is a measurement of how unique a given sequence is. Because classical recombination solely relies on the specificity of the homology regions, it requires a relatively stringent E-value cut off such as $10^{-20}$. Because KAISER boosts locus specificity not only by the specificity of the homology regions but also by the simultaneous loss of the negative selection marker and gain of positive selection marker, KAISER can in principle tolerate less stringent E-value(s) (e.g. less stringent homology regions). However, it is practically very straightforward to generate homology regions with stringent E-value, so suitably the $10^{-20}$ E-value cut off is used.

Selectable Markers

Suitable selectable markers are shown in the table below

TABLE 2

| Marker | Selection Scheme | Accession number/nucleic acid |
|---|---|---|
| sacB | sucrose sensitivity SEQ ID NO: 4 | sacB<br>ATGAACATCAAAAAGTTTGCAAAACAAGCAACAGTATTAACCTTTACTACCGCACTGCT<br>GGCAGGAGGCGCAACTCAAGCGTTTGCGAAAGAAACGAACCAAAAGCCATATAAGGAAA<br>CATACGGCATTTCCCATATTACACGCCATGATATGCTGCAAATCCCTGAACAGCAAAAA<br>AATGAAAAATATAAAGTTCCTGAGTTCGATTCGTCCACAATTAAAAATATCTCTTCTGC<br>AAAAGGCCTGGACGTTTGGGACAGCTGGCCATTACAAAACACTGACGGCACTGTCGCAA<br>ACTATCACGGCTACCACATCGTCTTTGCATTAGCCGGAGATCCTAAAAATGCGGATGAC<br>ACATCGATTTACATGTTCTATCAAAAGTCGGCGAAACTTCTATTGACAGCTGGAAAAA<br>CGCTGGCCGCGTCTTTAAAGACAGCGACAAATTCGATGCAAATGATTCTATCCTAAAAG<br>ACCAAACACAAGAATGGTCAGGTTCAGCCACATTTACATCTGACGGAAAAATCCGTTTA<br>TTCTACACTGATTTCTCCGGTAAACATTACGGCAAACAAACACTGACAACTGCACAAGT<br>TAACGTATCAGCATCAGACAGCTCTTTGAACATCAACGGTGTAGAGGATTATAAATCAA<br>TCTTTGACGGTGACGGAAAAACGTATCAAAATGTACAGCAGTTCATCGATGAAGGCAAC<br>TACAGCTCAGGCGACAACCATACGCTGAGAGATCCTCACTACGTAGAAGATAAAGGCCA<br>CAAATACTTAGTATTTGAAGCAAACACTGGAACTGAAGATGGCTACCAAGGCGAAGAAT<br>CTTTATTTAACAAAGCATACTATGGCAAAAGCACATCATTCTTCCGTCAAGAAAGTCAA<br>AAACTTCTGCAAAGCGATAAAAAACGCACGGCTGAGTTAGCAAACGGCGCTCTCGGTAT<br>GATTGAGCTAAACGATGATTACACACTGAAAAAAGTGATGAAACCGCTGATTGCATCTA<br>ACACAGTAACAGATGAAATTGAACGCGCGAACGTCTTTAAAATGAACGGCAAATGGTAC<br>CTGTTCACTGACTCCCGCGGATCAAAAATGACGATTGACGGCATTACGTCTAACGATAT<br>TTACATGCTTGGTTATGTTTCTAATTCTTTAACTGGCCCATACAAGCCGCTGAACAAAA<br>CTGGCCTTGTGTTAAAAATGGATCTTGATCCTAACGATGTAACCTTTACTTACTCACAC<br>TTCGCTGTACCTCAAGCGAAAGGAAACAATGTCGTGATTACAAGCTATATGACAAACAG<br>AGGATTCTACGCAGACAAACAATCAACGTTTGCGCCTAGCTTCCTGCTGAACATCAAAG<br>GCAAGAAAACATCTGTTGTCAAAGACAGCATCCTTGAACAAGGACAATTAACAGTTAAC<br>AAATAA |
| rpsL (S12 ribosomal protein | streptomycin sensitivity SEQ ID NO: 5 | rpsL<br>ATGGCAACAGTTAACCAGCTGGTACGCAAACCACGTGCTCGCAAAGTTGCGAAAAGCAA<br>CGTGCCTGCGCTGGAAGCATGCCCGCAAAAACGTGGCGTATGTACTCGTGTATATACTA<br>CCACTCCTAAAAAACCGAACTCCGCGCTGCGTAAAGTATGCCGTGTTCGTCTGACTAAC<br>GGTTTCGAAGTGACTTCCTACATCGGTGGTGAAGGTCACAACCTGCAGGAGCACTCCGT<br>GATCCTGATCCGTGGCGGTCGTGTTAAAGACCTCCCGGGTGTTCGTTACCACACCGTAC<br>GTGGTGCGCTTGACTGCTCCGGCGTTAAAGACCGTAAGCAGGCTCGTTCCAAGTATGGC<br>GTGAAGCGTCCTAAGGCTTAA |
| PheS with two point mutations | p-chloro-phenylalanine SEQ ID NO: 6 | PheS_T251A_A294G<br>ATGTCACATCTCGCAGAACTGGTTGCCAGTGCGAAGGCGGCCATTAGCCAGGCGTCAGA<br>TGTTGCCGCGTTAGATAATGTGCGCGTCGAATATTTGGGTAAAAAAGGGCACTTAACCC<br>TTCAGATGACGACCCTGCGTGAGCTGCCGCCAGAAGAGCGTCCGGCAGCTGGTGCGGTT<br>ATCAACGAAGCGAAAGAGCAGGTTCAGCAGGCGCTGAATGCGCGTAAAGCGGAACTGGA<br>AAGCGCTGCACTGAATGCGCGTCTGGCGGCGGAAACGATTGATGTCTCTCTGCCAGGTC<br>GTCGCATTGAAAACGGCGGTCTGCATCCGGTTACCCGTACCATCGACCGTATCGAAAGT<br>TTCTTCGGTGAGCTTGGCTTTACCGTGGCAACCGGGCCGGAAATCGAAGACGATTATCA<br>TAACTTCGATGCTCTGAACATTCCTGGTCACCACCCGGCGCGCGCTGACCACGACACTT<br>TCTGGTTTGACACTACCCGCCTGCTGCGTACCCAGACCTCTGGCGTACAGATCCGCACC<br>ATGAAAGCCCAGCAGCCACCGATTCGTATCATCGCGCCTGGCCGTGTTTATCGTAACGA<br>CTACGACCAGACTCACACGCCGATGTTCCATCAGATGGAAGGTCTGATTGTTGATACCA<br>ACATCAGCTTTACCAACCTGAAAGGCACGCTGCACGACTTCCTGCGTAACTTCTTTGAG<br>GAAGATTTGCAGATTCGCTTCCGTCCTTCCTACTTCCCGTTTGCCGAACCTTCTGCAGA<br>AGTGGACGTCATGGGTAAAAACGGTAAATGGCTGGAAGTGCTGGGCTGCGGGATGGTGC<br>ATCCGAACGTGTTGCGTAACGTTGGCATCGACCCGGAAGTTTACTCTGGTTTCGGCTTC<br>GGGATGGGGATGGAGCGTCTGACTATGTTGCGTTACGGCGTCACCGACCTGCGTTCATT<br>CTTCGAAAACGATCTGCGTTTCCTCAAACAGTTTAAATAA |
| Cm$^R$ | chloramphenicol resistance SEQ ID NO: 7 | CmR<br>ATGGAGAAAAAAATCACTGGATATACCACCGTTGATATATCCCAATGGCATCGTAAAGA<br>ACATTTTGAGGCATTTCAGTCAGTTGCTCAATGTACCTATAACCAGACCGTTCAGCTGG<br>ATATTACGGCCTTTTTAAAGACCGTAAAGAAAAATAAGCACAAGTTTTATCCGGCCTTT<br>ATTCACATTCTTGCCCGCCTGATGAATGCTCATCCGGAATTCCGTATGGCAATGAAAGA<br>CGGTGAGCTGGTGATATGGGATAGTGTTCACCCTTGTTACACCGTTTTCCATGAGCAAA<br>CTGAAACGTTTCATCGCTCTGGAGTGAATACCACGACGATTTCCGGCAGTTTCTACAC<br>ATATATTCGCAAGATGTGGCGTGTTACGGTGAAAACCTGGCCTATTTCCCTAAAGGGTT<br>TATTGAGAATATGTTTTCGTCTCAGCCAATCCCTGGGTGAGTTTCACCAGTTTTGATT<br>TAAACGTGGCCAATATGGACAACTTCTTCGCCCCCGTTTTCACCgTGGGCAAATATTAT |

TABLE 2-continued

| Marker | Selection Scheme | Accession number/nucleic acid |
|---|---|---|
|  |  | ACGCAAGGCGACAAGGTGCTGATGCCGCTGGCGATTCAGGTTCATCATGCCGTCTGTGA<br>TGGCTTCCATGTCGGCAGAATGCTTAATGAATTACAACAGTACTGCGATGAGTGGCAGG<br>GCGGGGCGTAA |
| KanR | kanamycin resistance SEQ ID NO: 8 | KanR<br>ATGATTGAACAAGATGGATTGCACGCAGGTTCTCCGGCCGCTTGGGTGGAGAGGCTATT<br>CGGCTATGACTGGGCACAACAGACAATCGGCTGCTCTGATGCCGCCGTGTTCCGGCTGT<br>CAGCGCAGGGGCGCCCGGTTCTTTTTGTCAAGACCGACCTGTCCGGTGCCCTGAATGAA<br>CTGCAGGACGAGGCAGCGCGGCTATCGTGGCTGGCCACGACGGGCGTTCCTTGCGCAGC<br>TGTGCTCGACGTTGTCACTGAAGCGGGAAGGGACTGGCTGCTATTGGGCGAAGTGCCGG<br>GGCAGGATCTCCTGTCATCTCACCTTGCTCCTGCCGAGAAAGTATCCATCATGGCTGAT<br>GCAATGCGGCGGCTGCATACGCTTGATCCGGCTACCTGCCCATTCGACCACCAAGCGAA<br>ACATCGCATCGAGCGAGCACGTACTCGGATGGAAGCCGGTCTTGTCGATCAGGATGATC<br>TGGACGAAGAGCATCAGGGGCTCGCGCCAGCCGAACTGTTCGCCAGGCTCAAGGCGCGC<br>ATGCCCGACGGCGAGGATCTCGTCGTGACCCATGGCGATGCCTGCTTGCCGAATATCAT<br>GGTGGAAAATGGCCGCTTTTCTGGATTCATCGACTGTGGCCGGCTGGGTGTGGCGGACC<br>GCTATCAGGACATAGCGTTGGCTACCCGTGATATTGCTGAAGAGCTTGGCGGCGAATGG<br>GCTGACCGCTTCCTCGTGCTTTACCGTATCGCCGCTCCCGATTCGCAGCGCATCGCCTT<br>CTATCGCCTTCTTGACGAGTTCTTCTGA |
| virtually any antibiotic marker e.g. TetR, AmpR, HyR, ErmR | Tetracycline, ampicillin, hygromycin, erythromycin resistance |  |

Excision/Introduction of Double Stranded Breaks

It should be noted that a mechanism for excision/introduction of double stranded breaks is an important part of the invention. This system may suitably be the CRISPR/Cas9 system. However, other systems producing this function are also known, for example zinc finger based approaches, and/or TALEN based approaches, and/or other approaches.

For example, there have been three recently published papers about alternative RNA-guided endonucleases as alternates to the original *Streptococcus* pyogenes CRISPR/Cas9 (Ran. F. A. et al. In vivo genome editing using *Staphylococcus aureus* Cas9. Nature 520, 186-191(2015); Zetsche, B. et al. Cpf1 is a single RNA-guided endonuclease of a class 2 CRISPR-Cas system. Cell 163, 759-771 (2015): Lee, C. M., Cradick, T. J. & Bao, G. The *Neisseria meningitidis* CRISPR-Cas9 System Enables Specific Genome Editing in Mammalian Cells. Mol. Ther. 24, 645-654 (2016).) They can all be used to guide in vivo excision in the invention such as in both KAISER 2 and KAISER 4 schemes. These references are expressly incorporated herein by reference specifically for the teachings of alternate systems for introduction of double stranded breaks/excisions as used herein.

Another type of system which can be used to support nucleic acid excision/double stranded breaks in the host cell, which system is completely different from RNA-guided endonucleases as noted above, is homing endonuclease. One such example is 1-TevIII from *Escherichia coli* phage RB3 with 30 bp recognition sequence (TATGTATCIT-TGCGTGTACCITTAACTTC (SEQ ID NO:9)), which is absent in *E. coli* genome (Eddy, S. R. & Gold, L. The phage T4 nrdB intron: a deletion mutant of a version found in the wild. Genes Dev. 5, 1032-1041(1991); Robbins, J. B. et al. Homing endonuclease I-TevIII: dimerization as a means to a double-strand break. Nucleic Acids Research 35, 1589-1600 (2007)). The cut site of I-TevIII is very close to the 5'end of the recognition sequence, making it compatible with KAISER 2 scheme in excising the donor nucleic acid (e.g. synthetic DNA) from the episomal replicon.

CRISPR/Cas9 Sequences

The CRISPR/Cas9 system is described in Jiang et al 2013 (Jiang, W., Cox, D., Zhang, F., Bikard. D. & Marraffini, L. A. RNA-guided editing of bacterial genomes using CRISPR-Cas systems. Nature Biotechnology 31, 233-239 (2013)).

In outline, guide RNA refers to the single fusion RNA between tracrRNA and spacerRNA. Suitably a combination of the constant tracrRNA and multiple different spacerRNAs is used in the invention. These tracrRNA spacerRNA combinations can optionally be replaced with multiple different guideRNAs.

In the art, the guide RNA only refers to the fusion of tracrRNA and spacerRNA as a single RNA, and does not mean the dual-RNA complex of tracrRNA and spacerRNA.

PAM stands for protospacer adjacent motif. This is typically a 3 nucleotide motif. A typical guide RNA is 30 nucleotides in length. The guide RNA typically comprises 27 nucleotides of target sequence as well as the 3 nucleotides of PAM sequence.

Suitably the same CRISPR setup of separate tracr RNA/spacer RNA as in Jiang et al 2013 may be used in the invention.

Alternatively, a single guide RNACRISPR setup may be used, for example as known in the art (see Le Cong et al. Multiplex genome engineering using CRISPR/Cas systems. Science 339, 819-823 (2013); Mali. P. et al. RNA-guided human genome engineering via Cas9. Science 339, 823-826 (2013)).

In order for the excision to be supported when CRISPR/Cas 9 is used, suitably the helper protein(s) capable of supporting nucleic acid excision comprise a minimum of: Cas9 (e.g. see below), and RNAseIII (e.g. rnc, accession ID EG10857 from EcoCyc), together with the relevant RNAs (spacerRNA guide, tracrRNA (see below)).

Exemplary sequences are provided below:

Cas9

(SEQ ID NO: 10)
ATGGATAAGAAATACTCAATAGGCTTAGATATCGGCACAAATAGCGTCGG

ATGGGCGGTGATCACTGATGAATATAAGGTTCCGTCTAAAAAGTTCAAGG

TTCTGGGAAATACAGACCGCCACAGTATCAAAAAAAATCTTATAGGGGCT

CTTTTATTTGACAGTGGAGAGACAGCGGAAGCGACTCGTCTCAAACGGAC

AGCTCGTAGAAGGTATACACGTCGGAAGAATCGTATTTGTTATCTACAGG

AGATTTTTTCAAATGAGATGGCGAAAGTAGATGATAGTTTCTTTCATCGA

CTTGAAGAGTCTTTTTTGGTGGAAGAAGACAAGAAGCATGAACGTCATCC

TATTTTTGGAAATATAGTAGATGAAGTTGCTTATCATGAGAAATATCCAA

CTATCTATCATCTGCGAAAAAAATTGGTAGATTCTACTGATAAAGCGGAT

TTGCGCTTAATCTATTTGGCCTTAGCGCATATGATTAAGTTTCGTGGTCA

TTTTTTGATTGAGGGAGATTTAAATCCTGATAATAGTGATGTGGACAAAC

TATTTATCCAGTTGGTACAAACCTACAATCAATTATTTGAAGAAAACCCT

ATTAACGCAAGTGGAGTAGATGCTAAAGCGATTCTTTCTGCACGATTGAG

TAAATCAAGACGATTAGAAAATCTCATTGCTCAGCTCCCCGGTGAGAAGA

AAAATGGCTTATTTGGGAATCTCATTGCTTTGTCATTGGGTTTGACCCCT

AATTTTAAATCAAATTTTGATTTGGCAGAAGATGCTAAATTACAGCTTTC

AAAAGATACTTACGATGATGATTTAGATAATTTATTGGCGCAAATTGGAG

ATCAATATGCTGATTTGTTTTTGGCAGCTAAGAATTTATCAGATGCTATT

TTACTTTCAGATATCCTAAGAGTAAATACTGAAATAACTAAGGCTCCCCT

ATCAGCTTCAATGATTAAACGCTACGATGAACATCATCAAGACTTGACTC

TTTTAAAAGCTTTAGTTCGACAACAACTTCCAGAAAAGTATAAAGAAATC

TTTTTTGATCAATCAAAAAACGGATATGCAGGTTATATTGATGGGGGAGC

TAGCCAAGAAGAATTTTATAAATTTATCAAACCAATTTTAGAAAAAATGG

ATGGTACTGAGGAATTATTGGTGAAACTAAATCGTGAAGATTTGCTGCGC

AAGCAACGGACCTTTGACAACGGCTCTATTCCCCATCAAATTCACTTGGG

TGAGCTGCATGCTATTTTGAGAAGACAAGAAGACTTTTATCCATTTTTAA

AAGACAATCGTGAGAAGATTGAAAAAATCTTGACTTTTCGAATTCCTTAT

TATGTTGGTCCATTGGCGCGTGGCAATAGTCGTTTTGCATGGATGACTCG

GAAGTCTGAAGAAACAATTACCCCATGGAATTTTGAAGAAGTTGTCGATA

AAGGTGCTTCAGCTCAATCATTTATTGAACGCATGACAAACTTTGATAAA

AATCTTCCAAATGAAAAGTACTACCAAACATAGTTTGCTTTATGAGTA

TTTTACGGTTTATAACGAATTGACAAAGGTCAAATATGTTACTGAAGGAA

TGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGA

TTATTTCAAAAAAATAGAATGTTTTGATAGTGTTGAAATTTCAGGAGTTG

AAGATAGATTTAATGCTTCATTAGGTACCTACCATGATTTGCTAAAAATT

ATTAAAGATAAAGATTTTTTGGATAATGAAGAAAATGAAGATATCTTAGA

GGATATTGTTTTAACATTGACCTTATTTGAAGATAGGGAGATGATTGAGG

AAAGACTTAAAACATATGCTCACCTCTTTGATGATAAGGTGATGAAACAG

CTTAAACGTCGCCGTTATACTGGTTGGGGACGTTTGTCTCGAAAATTGAT

TAATGGTATTAGGGATAAGCAATCTGGCAAAACAATATTAGATTTTTTGA

AATCAGATGGTTTTGCCAATCGCAATTTTATGCAGCTGATCCATGATGAT

AGTTTGACATTTAAAGAAGACATTCAAAAAGCACAAGTGTCTGGACAAGG

CGATAGTTTACATGAACATATTGCAAATTTAGCTGGTAGCCCTGCTATTA

AAAAAGGTATTTTACAGACTGTAAAAGTTGTTGATGAATTGGTCAAAGTA

ATGGGGCGGCATAAGCCAGAAAATATCGTTATTGAAATGGCACGTGAAAA

TCAGACAACTCAAAAGGGCCAGAAAAATTCGCGAGAGCGTATGAAACGAA

TCGAAGAAGGTATCAAAGAATTAGGAAGTCAGATTCTTAAAGAGCATCCT

GTTGAAAATACTCAATTGCAAATGAAAAGCTCTATCTCTATTATCTCCA

AAATGGAAGAGACATGTATGTGGACCAAGAATTAGATATTAATCGTTTAA

GTGATTATGATGTCGATCACATTGTTCCACAAAGTTTCCTTAAAGACGAT

TCAATAGACAATAAGGTCTTAACGCGTTCTGATAAAAATCGTGGTAAATC

GGATAACGTTCCAAGTGAAGAAGTAGTCAAAAAGATGAAAAACTATTGGA

GACAACTTCTAAACGCCAAGTTAATCACTCAACGTAAGTTTGATAATTTA

ACGAAAGCTGAACGTGGAGGTTTGAGTGAACTTGATAAAGCTGGTTTTAT

CAAACGCCAATTGGTTGAAACTCGCCAAATCACTAAGCATGTGGCACAAA

TTTTGGATAGTCGCATGAATACTAAATACGATGAAAATGATAAACTTATT

CGAGAGGTTAAAGTGATTACCTTAAAATCTAAATTAGTTTCTGACTTCCG

AAAAGATTTCCAATTCTATAAAGTACGTGAGATTAACAATTACCATCATG

CCCATGATGCGTATCTAAATGCCGTCGTTGGAACTGCTTTGATTAAGAAA

TATCCAAAACTTGAATCGGAGTTTGTCTATGGTGATTATAAAGTTTATGA

TGTTCGTAAAATGATTGCTAAGTCTGAGCAAGAAATAGGCAAAGCAACCG

CAAAATATTTCTTTTACTCTAATATCATGAACTTCTTCAAAACAGAAATT

ACACTTGCAAATGGAGAGATTCGCAAACGCCCTCTAATCGAAACTAATGG

GGAAACTGGAGAAATTGTCTGGGATAAAGGGCGAGATTTTGCCACAGTGC

GCAAAGTATTGTCCATGCCCCAAGTCAATATTGTCAAGAAAACAGAAGTA

CAGACAGGCGGATTCTCCAAGGAGTCAATTTTACCAAAAAGAAATTCGGA

CAAGCTTATTGCTCGTAAAAAAGACTGGGATCCAAAAAAATATGGTGGTT

TTGATAGTCCAACGGTAGCTTATTCAGTCCTAGTGGTTGCTAAGGTGGAA

AAAGGGAAATCGAAGAAGTTAAAATCCGTTAAAGAGTTACTAGGGATCAC

AATTATGGAAAGAAGTTCCTTTGAAAAAAATCCGATTGACTTTTTAGAAG

CTAAAGGATATAAGGAAGTTAAAAAAGACTTAATCATTAAACTACCTAAA

TATAGTCTTTTTGAGTTAGAAAACGGTCGTAAACGGATGCTGGCTAGTGC

CGGAGAATTACAAAAGGGAAATGAGCTGGCTCTGCCAAGCAAATATGTGA

ATTTTTTATATTTAGCTAGTCATTATGAAAAGTTGAAGGGTAGTCCAGAA

GATAACGAACAAAAACAATTGTTTGTGGAGCAGCATAAGCATTATTTAGA

TGAGATTATTGAGCAAATCAGTGAATTTTCTAAGCGTGTTATTTTAGCAG

ATGCCAATTTAGATAAAGTTCTTAGTGCATATAACAAACATAGAGACAAA

CCAATACGTGAACAAGCAGAAAATATTATTCATTTATTTACGTTGACGAA

-continued

TCTTGGAGCTCCCGCTGCTTTTAAATATTTTGATACAACAATTGATCGTA

AACGATATACGTCTACAAAAGAAGTTTTAGATGCCACTCTTATCCATCAA

TCCATCACTGGTCTTTATGAAACACGCATTGATTTGAGTCAGCTAGGAGG

TGACTGA tracrRNA
(SEQ ID NO: 11)
AAAAAGTTTAAATTAAATCCATAATGATTTGATGATTTCAATAATAGTTT

TAATGACCTCCGAAATTAGTTTAATATGCTTTAATTTTTCTTTTTCAAAA

TATCTCTTCAAAAAATATTACCCAATACTTAATAATAAATAGATTATAAC

ACAAAATTCTTTTAAAAAGTAGTTTATTTTGTTATCATTCTATAGTATTA

AGTATTGTTTTATGGCTGATAAATTTCTTTGAATTTCTCCTTGATTATTT

GTTATAAAAGTTATAAAATAATCTTGTTGGAACCATTCAAAACAGCATAG

CAAGTTAAAATAAGGCTAGTCCGTTATCAACTTGAAAAAGTGGCACCGAG

TCGGTGCTTTTTTTGATACTTCTATTCTACTCTGACTGCAAACCAAAAAA

ACAAGCGCTTTCAAAACGCTTGTTTTATCATTTTTAGGGAAATTAATCTC

TTAATCCTTTT

The actual sequences of Cas9 and tracrRNA typically remain constant through all experiments.

The spacerRNA sequence changes as a function of the exact CRISPR/Cas9 cutting sites.

Suitably Cas9, tracrRNA and spacerRNA are provided together to the cell in which the excision takes place (i.e. the host cell). Suitably all three of these elements are essential for efficient excision.

In one embodiment the tracrRNA is constitutively expressed in the host cell. The Cas9 is induced together with the helper protein(s) capable of supporting nucleic acid recombination (such as lambda red alpha/beta/gamma). The spacerRNA is provided last to the host cell by transforming the cell with a small plasmid expressing spacerRNA(s). At this stage, when all the three components are in the cell, the excision happens.

In another embodiment, the nucleic acid (such as DNA) sequence to express the Cas9, the tracrRNA, and the spacerRNA can be provided together to the cell, while the actual expression of (some of) the three components may be suppressed (uninduced/silent). At the appropriate time, the expression may induced, and thus inducing the excision.

In a preferred embodiment, the tracrRNA is constantly (constitutively) expressed, the expression of Cas9 is induced, and the spacerRNA is provided last to trigger excision, induction of expression is well within the abilities of a skilled worker in the art. For example, the sequence of interest (such as Cas9) is placed under the control of an inducible promoter. That promoter activity is induced when desired. For example the well-known arabinose (pAra) promoter may be used, which is induced in the presence of arabinose. Similarly, the skilled worker may choose constitutive promoters from a vast array of well-known promoters suitable for constitutive expression as desired. For further guidance, we refer to the examples section below.

As is well known in relation to operating the CRISPR system, the sequences of spacerRNAs are different for different target sites. Choosing appropriate spacerRNAs is well within the ambit of the skilled person.

In case further guidance is required, below is an example of spacerRNA sequences:

>Spacers1_2_3_4
(SEQ ID NO: 12)
tatttcttaataactaaaaatatggtataatactcttaataaatgcagta atacaggggcttttcaagactgaagtctagctgagacaaatagtgcgatt acgaaattttttagacaaaaatagtctacgaggttttagagctatgctgt tttgaatggtcccaaaacCGCGGCTTAGCTACGGCTGAGCACGCCCCTgt tttagagctatgctgttttgaatggtcccaaaacGTGGGAATAAGGGGTG AGGCTGGCATGCCTgttttagagctatgctgttttgaatggtcccaaaac CGCGAACAAAAATACGCGCCAGGTGAAAATgttttagagctatgctgttt tgaatggtcccaaaacCCACTTTGCCCCACAATTTCCCACTGACCGgttt tagagctatgctgattgaatggtcccaaaacttcagcacactgagacttg ttgagtt The sequence in lower case constitutes the flanking sequences, the promoter, and the Direct Repeats region of the actual spacerRNA locus, which stay constant throughout all the examples presented herein. The sequences in UPPER CASE are four different spacerRNA sequences (Spacer 1, 2, 3, and 4) used in one specific manipulation. The skilled person simply varies the UPPER CASE spacerRNA sequences according to their particular target nucleic acid sequence.

The tracrRNA & spacerRNA combination can be provided separately, or can be provided as a single guide RNA, which is a fusion of the tracrRNA & spacerRNA.

It should be noted that different motifs are required for different elements of the CRISPR system. For Cas9, the PAM is NGG.

In more detail, alternate implementations of the CRISPR system may be used depending on operator choice, for example implementations which lead to alternate PAM's being used. In more detail, it has been demonstrated that the *Streptococcus pyogenes* CRISPR/Cas9 system, which naturally recognizes NGG as PAM, can be engineered to recognize altered PAM (Kleinstiver. B. P. et al. Engineered CRISPR-Cas9 nucleases with altered PAM specificities. Nature (2015). doi:10.1038/nature14592). The three alternative RNA-guided endonuclease systems as mentioned in Ran 2015, Zetsche 2015 and Lee 2016 (see above) naturally have different PAMs. Homing endonuclease 1-TevIII only has a specific recognition sequence and no PAM.

The skilled operator will realise that if alternative components of the CRISPR system are employed in the invention then the corresponding alternate cognate PAM sequence should be used. This is well within the ambit of the skilled worker. In case any further guidance is needed, the following table shows alternate elements of the CRISPR system together with their PAM sequences.

TABLE 3

| Name | Species | PAM/Motif | Reference | PMID |
|------|---------|-----------|-----------|------|
| Cas9 | *Streptococcus pyogenes* | NGG | 11.1126/science.1225829 | 22745249 |

TABLE 3-continued

| Name | Species | PAM/Motif | Reference | PMID |
|---|---|---|---|---|
| Cas9 variant | Streptococcus thermophilus A | NGGNG | 10.1038/nature13579 | 25079318 |
| Cas9 variant | Streptococcus thermophilus B | NNAGAAW | 10.1038/nature14592 | 26098369 |
| Cas9 variant | Staphylococcus aureus | NGRRT or NGRRN | 10.1038/nature14592 | 26098369 |
| Cas9 variant | Neisseria meningitidis | NNNNGATT | 10.1038/nmeth.2681 | 24076762 |
| Cas9 variant | Treponema denticola | NAAAAC | 10.1038/nmeth.2681 | 24076762 |
| Cas9 variant | Listeria innocua | NGG | 10.1038/nature13579 | 25079318 |
| Cas9 variant | Francisella novicida | NG | 10.1038/nature13579 | 25079318 |
| Cas9 variant | Lactobacillus buchneri | NAAAAN | 10.1038/nature13579 | 25079318 |
| Cas9 variant | Campylobacter jejuni | NNNNACA | 10.1038/nature13579 | 25079318 |
| Cas9 variant | Pasteurella multocida | GNNNCNNA | 10.1038/nature13579 | 25079318 |
| eSpCas9 | Streptococcus pyogenes | NGG | 10.1126/science.aad5227 | 26628643 |
| SpCas9-HF1 | Streptococcus pyogenes | NGG | 10.1038/nature16526 | 26735016 |
| Cas9-nickase | D10A & H840A of S. pyogenes | NGG | 10.1038/nature.2857 | 24584192 |
| dCas9-FokI | Streptococcus pyogenes | NGG | 10.1038/nbt.2908 | 24770325 |
| Cpf1 | Francisella novicida | TTN | 10.10.16/j.cell.2015.09.038 | 26422227 |
| NgAgo | Natronobacterium gregoryi | programmable | 10.1038/nbt.3547 | 27136078 |
| TtAgo | Thermus thermophilus | programmable | 10.1038/nature12971 | 24531762 |
| PfAgo | Pyrococcus furiosus | programmable | 10.1093/nar/gkv415 | 25925567 |
| I-SceI SEQ ID NO: 13 | Restriction Enzyme | TAGGGATAACAG GGTAAT | NEB | n/a |

Manipulation of Pam Sites for Controlled Excision

When operating the invention, the PAM's on the target sequence should be compared to the PAM's on the donor nucleic acid (e.g. sDNA) going INTO the target and if necessary mutated so as to avoid a double excision problem (e.g. excision accidentally including the homologous recombination sequences) if the PAM sequences match on the donor nucleic acid (e.g. sDNA) and target nucleic acid (e.g. genome DNA). This is easily done by the skilled worker in arranging the elements in the order as taught herein.

KAISER 2 and Similar

In more detail, when operating the KAISER 2 or similar embodiments, the homologous regions flanking the donor nucleic acid (e.g. synthetic DNA) on the episomal replicon are optionally further flanked by AvrII sites (CCTAGG). The TGG or CCA corresponds to the NGG PAM sequence (depending on the orientation) required by the CRISPR/Cas9 system from Streptococcus pyogenes, while the complementing CCA or TGG constitutes the last three nucleotides of the protospacer. Any substitution in the last three nucleotides of the protospacer and/or any of the G in the NGG PAM will disable CRISPR/Cas9 recognition and/or cut. The two AvrII sites in KAISER 2 scheme constitute part of the episomal replicon backbone and can be easily avoided to be right next to the corresponding end of the homologous regions on the target nucleic acid (e.g. the host genome) (1 AvrII site in 4 kb on average). In this way, the two cut sites (excision sites) on the episomal replicon can be easily differentiated from the corresponding end of the homologous regions on the target nucleic acid (e.g. genome) in KAISER 2 scheme for both insertion and replacement.

KAISER 4 and Similar

When the invention is operated through the KAISER 4 embodiment, care is needed in choosing the PAM employed on the sequence resident in the nucleic acid being altered (target nucleic acid). The reason is that the sequence on the donor nucleic acid (such as DNA being introduced into the target nucleic acid) should not match the PAM on the target nucleic acid. If those do match, then the excision step of the method of the invention risks also introducing double stranded breaks in the target nucleic acid at an inappropriate location. Therefore, suitably the PAM on the target nucleic acid (such as the genome or the plasmid or the BAC into which the donor DNA is being added/inserted) should be compared to the PAM on the episomal replicon bearing the donor nucleic acid; if the PAM sequences are found to match then they should be mutated on the target nucleic acid being altered so as to avoid this possible problem. This is well within the ambit of the skilled reader. In more detail, in KAISER 4 or similar embodiments, the two cut sites on the episomal replicon is differentiated from the corresponding end of the homologous regions on the target nucleic acid in the same way as in KAISER 2 scheme. The two additional cut sites on the inner side of the homologous regions on the target nucleic acid need to be identified by looking for NGG motifs, which define the boundary of the homologous regions on the target nucleic acid. The NGG PAMs of the two additional cut sites on the inner side of the homologous regions on the target nucleic acid also need to be absent on the corresponding end of the homologous regions on the episomal replicon bearing the donor nucleic acid to avoid the "double excision". This can be very easily achieved when applying KAISER 4 scheme for insertion of donor nucleic acid (such as synthetic DNA) as the sequence for insertion is naturally different from the cut sites on the target nucleic acid (such as the genome). This should be carefully arranged when applying KAISER 4 scheme for replacement when the donor nucleic acid (e.g. synthetic DNA) has similar sequence to the target nucleic acid (such as wildtype genomic DNA). This is achieved in replacement by changing the corresponding NGG in the donor nucleic acid (e.g. synthetic DNA) and/or the last three nucleotide in the otherwise protospacer right next to the NGG. In this way, we mark the cut sites only to the target nucleic acid (e.g. genome) positions.

Thus suitably the donor nucleic acid sequence comprises in order: 5'-excision cut site-homologous recombination sequence 1-sequence of interest-homologous recombination sequence 2-excision cut site-3'

In one embodiment it may be desirable to induce a cut on the target nucleic acid in order to assist in selection for recombinants; this is sometimes referred to as 'KAISER 3' because in this embodiment suitably there are 3 cuts-two on the episomal replicon to excise the donor nucleic acid and one on the target nucleic acid to assist in selection. Thus suitably said target nucleic acid comprises in order: 5'-homologous recombination sequence 1-cut site-homologous recombination sequence 2-3'

Suitably said target nucleic acid comprises in order:

a) 5'-homologous recombination sequence 1-cut site-homologous recombination sequence 2-3' b) 5'-homologous recombination sequence 1-positive selectable marker-homologous recombination sequence 2-3', further comprising a cut site between said homologous recombination sequence 1 and homologous recombination sequence 2 c) 5'-homologous recombination sequence 1-negative selectable marker-homologous recombination sequence 2-3', further comprising a cut site between said homologous recombination sequence 1 and homologous recombination sequence 2 d) 5'-homologous recombination sequence 1-positive selectable marker-negative selectable marker-homologous recombination sequence 2-3', further comprising a cut site between said homologous recombination sequence 1 and homologous recombination sequence 2 e) 5'-homologous recombination sequence 1-negative selectable marker-positive selectable marker-homologous recombination sequence 2-3', further comprising a cut site between said homologous recombination sequence 1 and homologous recombination sequence 2

When applying the invention in multiple rounds, the donor nucleic acid of a first round contributes/becomes part of the target nucleic acid in next round. Thus suitably the sequence of interest may comprise in order:

a) 5'-homologous recombination sequence 1-cut site-homologous recombination sequence 2-3' b) 5'-homologous recombination sequence 1-positive selectable marker-homologous recombination sequence 2-3', further comprising a cut site between said homologous recombination sequence 1 and homologous recombination sequence 2 c) 5'-homologous recombination sequence 1-negative selectable marker-homologous recombination sequence 2-3', further comprising a cut site between said homologous recombination sequence 1 and homologous recombination sequence 2 d) 5'-homologous recombination sequence 1-positive selectable marker-negative selectable marker-homologous recombination sequence 2-3', further comprising a cut site between said homologous recombination sequence 1 and homologous recombination sequence 2 e) 5'-homologous recombination sequence 1-negative selectable marker-positive selectable marker-homologous recombination sequence 2-3', further comprising a cut site between said homologous recombination sequence 1 and homologous recombination sequence 2 Suitably the cut site on the target nucleic acid or sequence of interest is different from the excision site on the episomal replicon/donor nucleic acid.

Said cut site may be between said positive/negative selectable markers, or may be within said positive/negative selectable markers.

Suitably said target nucleic acid comprises two such cut sites.

Suitably said cut site is adjacent to one of said homologous recombination sequences.

Suitably said two cut sites comprise a first cut site adjacent to said homologous recombination sequence 1, and a second cut site adjacent to said homologous recombination sequence 2.

Suitably the excision site is a sequence recognised by the helper protein(s) and/or RNAs capable of supporting nucleic acid excision of step (c).

Suitably the episomal replicon/donor sequence comprises two said excision sites; suitably said helper protein(s) and/or RNAs of step (c) are cognate for said excision sites.

Suitably said excision site or cut site comprises a protospacer and a PAM cognate for CRISPR/Cas9; suitably said helper protein(s) and/or RNAs capable of supporting nucleic acid excision comprise CRISPR/Cas9 and the cognate RNAs.

Size Limits

Data presented in this application show that efficiency is independent of the lengths of the synthetic nucleic acid such as DNA being introduced. Thus, without wishing to be bound by theory, it appears that this new invention has the advantage that there is no size limit.

In practice, the size limit is imposed only by the size of synthetic nucleic acid which can be manipulated. For example, the current view in the art is that bacterial artificial chromosomes (BACs) are effective for 200 to 300 kb of nucleic acid sequence. A BAC replicon is typically approximately 10 kb. Therefore, for a total maximum BAC size of approximately 310 kb, allowing 10 kb for the replicon, approximately 300 kb of synthetic nucleic acid such as DNA can be incorporated per round according to the invention.

Yeast artificial chromosomes (YACs) can be larger. A typical size limit for a YAC is 2 to 3 Mb (megabases).

Applications

The invention is useful in the construction of plasmids.

The invention is useful in manipulation of host genomes.

The invention is useful in the construction of artificial chromosomes such as BACs.

It is an advantage of the invention that transformation is uncoupled from recombination.

It is an advantage of the invention that in vitro manipulations can be avoided. It is an advantage of the invention that nucleic acid manipulations are carried out in vivo.

When the invention is applied to a genome, suitably the genome is a non-human genome, suitably a non-mammalian genome. Suitably the genome is a prokaryotic genome, suitable a bacterial genome.

The invention finds particular application in the making of large sized nucleic acid constructs.

The invention finds particular application in the creation of high diversity libraries. In this regard, a transformation efficiency of approximately $10^8$ is achievable using current transformation techniques. However, a transformation efficiency of $10^{10}$ or beyond is extremely challenging and/or problematic. According to the present invention, a first half-library may be created and transformed into a first host cell (population of host cells). This first half-library is then transformed with nucleic acid encoding the second half-library. By using recombination according to the present invention, those two half-libraries are then combined in vivo resulting in a library having diversity of $10^{10}$, which has advantageously been obtained having only ever needing to use a transformation efficiency of $10^5$.

According to the present invention, there is provided a combination method comprising an episomal replicon, in vivo excision and recombination. Suitably, said combination method further comprises double selection.

The term 'episome' has its ordinary meaning in the art, for example any accessory extrachromosomal replicating genetic element that can exist either autonomously or can become integrated with the chromosome.

Suitably excision is performed to generate a linear donor nucleic acid.

Multiple origins of replication active in the same cell on the same single nucleic acid are not usually desirable. This is especially true for example when a multicopy episomal nucleic acid such as a plasmid is carrying the donor nucleic acid-in this scenario it is clearly not desirable to incorporate the plasmid origin of replication into (for example) a BAC or into the host genome. Thus, suitably said excised linear donor nucleic acid does not comprise an origin of replication. Suitably the target nucleic acid sequence comprises an origin of replication.

Suitably the origin of replication on the episomal replicon comprising the donor sequence must match with host. e.g. all prokaryotic. Suitably the origins of replication on the episomal replicon comprising the target and on the episomal replicon comprising donor sequence must match with host. e.g. all prokaryotic.

Suitably the episomal replicon comprising the donor sequence comprises a prokaryotic origin of replication.

Suitably the replicon comprising the target sequence comprises a prokaryotic origin of replication. Suitably the replicon comprising the target sequence is an episomal replicon and comprises a prokaryotic origin of replication.

Suitably the host cell is prokaryotic.

Suitably the synthetic genome is a synthetic prokaryotic genome.

Further Description of the Invention

CRISPR/Cas9 provides an in vivo cutting of nucleic acid. In the prior art, this system has been used to introduce single cuts into target nucleic acids.

In the prior art, restriction enzyme systems have been used to introduce single cuts into a target nucleic acid. For example, restriction enzymes have been used to make a single cut into an introduced plasmid, thereby rendering it linear in vivo. This has typically been done in the study of recombination, when linear nucleic acid is required. This has also been done in the prior art in order to remove unwanted plasmids by cutting them—linear nucleic acids typically do not persist in the host cell and are lost.

We teach for the first time coupling of recombination to cutting of the target nucleic acid, for example as accomplished in KAISER 4.

In one embodiment, the invention may involve a first recombination step carried out by conventional techniques. This has the advantage of allowing introduction into the target site of the contra-selectable markers.

Optionally the invention comprises a final step of a final recombination which may be accomplished either by the KAISER technique or by conventional recombination. For example, this may be advantageous in removing selectable markers which have served their purpose and are no longer required for further rounds of KAISER recombination.

In one embodiment it may be possible to begin and continue the KAISER nucleic acid editing process without a first conventional homologous recombination event—for example, it may be possible to employ the excision machinery such as CRISPR/Cas9 to cut at a site intended to be replaced by recombination event, thereby creating selective pressure against the cut (and not recombined) target nucleic acid i.e. negative selection by double stranded break. In another embodiment it may be possible to use this negative selection by double stranded break in the target sequence to improve selection with a 3-DS break embodiment (2 DS breaks for excision of the donor nucleic acid and one DS break between the HR1 and HR2 sequences on the target nucleic acid making 3 DS breaks/cuts in total—this is sometimes referred to as 'KAISER 3').

The inventors assert that in the prior art conventional recombination has never involved a double selection as taught by the present invention. The inventors assert that conventional recombination has only ever used positive selection in the prior art.

In the prior art it has occasionally been taught to use one positive selection and one negative selection. Prior art methods of this nature select gain of the positive marker. They then recombine. After recombination, the selection is carried out for loss of the negative marker. By contrast, the present invention teaches positive and negative selection for a single recombination event.

An episomal replicon is an episomal nucleic acid which possesses its own origin of replication capable of functioning within said host cell. Nucleic acid segments such as DNA segments transfected into cells for recombination purposes in the prior art are not replicons because they do not possess an origin of replication for said host cell. For example, in some prior art settings a bacterial plasmid might be transfected into a mammalian cell. That plasmid is not a replicon in that host cell because it does not possess an origin of replication capable of functioning within said host cell. The only origin of replication which that prior art plasmid may possess is active in bacterial cell(s), not the host cell into which it has been transfected for further procedures.

Recombination Support It is an advantage of the invention that no host functions are relied upon.

Suitably the recombination function is provided exogenously, for example on the replicon carrying the donor nucleic acid (such as synthetic nucleic acid) to be introduced into the target nucleic acid.

Suitably the recombination support is provided by the lambda Red system.

Suitably nucleic acid repair systems such as RecBCD are inactivated. Suitably the lambda Red inhibitor of RecBCD is supplied.

Suitably the excision function is provided by CRISPR/Cas9.

Host Cell

Suitably the host cell is a prokaryotic cell.

Suitably the host cell is a bacterial cell.

In one embodiment suitably the host cell is in vitro i.e. in the laboratory. In one embodiment suitably the methods of the invention are in vitro methods. Suitably the methods are not practised in vivo. Suitably the host cell is not part of a live human or animal body.

Suitably the host cell is selected from one of the host cells used in the examples below.

Suitably the host cell may be any gram-negative bacterium. Suitably the host cell may be any *E. coli* strain (such as MG1655 or BL21), or cells derived therefrom. MG1655 is considered as the wild type strain of *E. coli*. The GenBank ID of genomic sequence of this strain is U00096 (U00096.3 as of the date of filing).

BL21 is widely available commercially. For example, it can be purchased from New England BioLabs (240 County Road, Ipswich, Mass. 01938-2723, USA) with catalog number C2530H.

Most suitably the host cell is MDS42 with Product No. E-0742 from ScarabGenomics.

Advantages

It is an advantage of the invention that the size of nucleotide sequences which can be manipulated enable an entire synthetic genome to be created. This is sometimes referred to as "GENESIS".

In contrast to Jiang et al 2013, where the authors try to change precisely at the cutting sites on the genome, the present invention is directed at changing nucleic acids between the sites. For example, we teach to replace the entire fragment between the two cutting sites which we generate on the genome in the KAISER 4 scheme. In the KAISER 2 scheme, we do not need to cut the genome.

The invention is useful to insert very long donor nucleic acids such as synthetic DNA (sDNA) at a defined genomic locus and to replace a very long stretch of target nucleic acid such as genomic DNA (gDNA) with sDNA with 100% locus specificity and reliable high efficiency independent of sDNA length. The invention such as REXER/KAISER fundamentally outperforms the alternative technology classical homologous recombination. Classical recombination can only insert/replace a few kb sDNA at a time with limited efficiency and locus specificity, while we have demonstrated that The invention such as REXER/KAISER can robustly insert/replace 100 kb or more sDNA into the genome with very high efficiency and 100% locus specificity in a length independent manner.

The invention fundamentally changes ways how we can modulate an organism's genome, which opens up new possibilities in metabolic engineering and de novo genome synthesis. Previously, long stretches of sDNA in the range of several 100 kb for the purpose of metabolic engineering or genome synthesis can only theoretically be introduced by potentially hundreds steps of classical recombination, which is not practically possible and thus has never been done commercially. The invention enables such task to be routinely and robustly performed with great simplicity, specificity, and efficiency.

The invention provides length independent DNA insertion and replacement, and enables large scale synonymous genome recoding.

It is an advantage that the invention may be applied in prokaryotes such as *E. coli* which divide very fast (e.g. 20 min each division). Known manipulations in eukaryotic host cells (e.g. Sakura et al 2016) use host cells which divide very slowly (days to weeks to divide), using vector which cannot replicate in the host cell, which makes their technology difficult or impossible to transfer to prokaryotic cells.

Moreover, Sakura et al 2016 use the endogenous recombination machinery of their eukaryote host cells to facilitate recombination, which is not directly transferable to prokaryotes. In the invention, helper proteins capable of supporting nucleic acid recombination are provided, such as lambda red components of viral origin provided in prokaryote host, which lacks the corresponding endogenous recombination machinery. In Sakura et al, all components are transiently introduced into the host while the invention provides that the components can be stably transformed and maintained in the host.

Sakura et al do not describe any mode comparable to KAISER 2; in KAISER 2 only the episomal replicon comprising a donor nucleic acid sequence (e.g. circular vector comprising donor sequence) is cut. Thus in some embodiments suitably only the episomal replicon comprising a donor nucleic acid sequence is cut. Thus in some embodiments suitably the target sequence is not cut.

Moreover, both the foreign circular DNA and the eukaryotic genome are cut in FIG. 2c and FIG. 3 of Sakura et al. 2016. A fundamental difference between Sakura's teaching and the present invention is that the foreign DNA in Sakura is not an episomal replicon in their system. Additionally, Sakura et al do not use simultaneous double selection to select for the simultaneous gain of synthetic DNA and loss of the original genomic sequence. Suitably the invention comprises the step of simultaneously selecting for the positive selectable marker carried on the sequence of interest of the donor nucleic acid, and for the loss of a selectable marker, suitably a negative selectable marker, on the target nucleic acid.

In contrast to Traver et al 2009, which is intrinsically limited by the position of the endonucleases to do the excision, advantageously the invention is very flexible regarding excision positions on either the donor (e.g. BAC) or target (e.g. genome) by utilizing helper proteins and/or RNAs (e.g. CRISPR/Cas9 system) capable of supporting excision at a range of sites.

Further Applications and Embodiments

In one aspect, the invention relates to a method for introducing a donor nucleic acid into a target nucleic acid, said method comprising providing a host cell said host cell comprising an episomal nucleic acid, said episomal nucleic acid comprising a donor nucleic acid sequence, said host cell further comprising a target nucleic acid, providing helper protein(s) capable of supporting nucleic acid recombination in said host cell providing helper protein(s) capable of supporting nucleic acid excision in said host cell wherein said donor nucleic acid sequence comprises in order: 5'-homologous recombination sequence 1-sequence of interest-homologous recombination sequence 2-3' wherein said sequence of interest comprises a positive selectable marker inducing excision of said donor nucleic acid sequence incubating to allow recombination between the excised donor nucleic acid and said target nucleic acid selecting for recombinants having incorporated said donor nucleic acid into said target nucleic acid.

In a broad aspect, the invention relates to a method comprising providing a host cell, said host cell comprising an episomal nucleic acid, said episomal nucleic acid comprising a donor nucleic acid sequence, said host cell further comprising a target nucleic acid, providing helper protein(s) capable of supporting nucleic acid recombination in said host cell, providing helper protein(s) capable of supporting nucleic acid cleavage in said host cell, wherein said donor nucleic acid sequence comprises in order: 5'-homologous recombination sequence 1-sequence of interest-homologous recombination sequence 2-3', wherein said sequence of interest comprises a positive selectable marker, inducing cleavage of said donor nucleic acid sequence to produce a linear donor nucleic acid, incubating to allow recombination between the linear donor nucleic acid and said target nucleic acid, and selecting for recombinants having incorporated said donor nucleic acid into said target nucleic acid.

In one aspect, the invention relates to a method that can also indicate problematic regions on the synthetic DNA that are deleterious down to a single nucleotide resolution. Also described is a method that can easily fix these identified problematic regions.

Thus the invention enables to identify and fix otherwise deleterious sequence within synthetic DNA. The inventors believe that KAISER/REXER is the only method with this property. This has utility in debugging synthetic DNA sequences which workers are trying to integrate into the genome.

In this regard, FIGS. 10, 11 and 12 demonstrate using KAISER/REXER to recode 20 kb of genome, identifying allowed and disallowed recoding schemes. FIG. 13 (also FIG. 17 (Extended Data FIG. 9)) demonstrates the ability to identify and fix such deleterious sequence (referred to as idiosyncratic positions/sequences in the examples below) as mentioned above.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which:

FIG. 1 shows Double Selection Recombination (DOSER) enhances recombination at a target locus. a. Classical recombination and DOSER. Classical recombination: linear double stranded DNA with a synthetic DNA (s. DNA) sequence and a positive selection marker (+, $Cm^R$ encoding the chloramphenicol resistance gene chloramphenicol acetyl transferase) flanked by homologous region 1 (HR1) and homologous region 2 (HR2) is transformed into the cell. Recombinants are selected by expression of the positive selection marker. DOSER: s. DNA is coupled with a negative selection marker, −2 (sacB, conferring sensitivity to sucrose), and positive selection marker, +2 ($Cm^R$), and integrated in place of distinct negative, −1 (rpsL, encoding the essential ribosomal protein S12 and conferring sensitivity to streptomycin), and positive, +1 ($Kan^R$, encoding the kanamycin resistance gene neomycin phosphotransferase II), selection markers that were previously introduced into the genome. Double selection for the gain of +2 and loss of −1 guarantees recombination at the target genomic locus. b. Classical recombination is performed by selecting the gain of $Cm^R$ only, while DOSER is performed by selecting the simultaneous gain of $Cm^R$ and loss of rpsL. Multiple colonies from classical recombination and DOSER were picked and analysed by colony PCR. c. All of the clones isolated by DOSER have integrated at the target locus. The data show the mean of three independent experiments, the error bars represent the standard deviation. N.B. FIG. 1a shows prior art approach 'classical recombination' and is not part of the invention.

FIG. 9 (Supplementary FIG. 2) shows by iterating REXER. 220 kb of the genome is replaced with 230 kb of synthetic DNA. a. Iterative genomic changes by REXER. The alternating use of two distinct double selection cassettes −1/+1 (rpsL-$Kan^R$) and −2/+2 (sacB-$Cm^R$) with one cassette marked at a defined locus on the genome and the other cassette on the BAC coupled with synthetic DNA, allows the product of one round of REXER to act as a template for the next round of REXER. b. Efficient replacement of genomic rpsL-$Kan^R$ with BAC bound sacB-$Cm^R$ using REXER 2 and REXER 4. The sacB-$Cm^R$ is integrated into the genomic locus (between 89,061 and 89,587) marked with rpsL-$Kan^R$ using REXER 2 and REXER 4. 11 colonies from REXER 2 and 11 colonies from REXER 4 were correct by phenotype, colony PCR, and DNA sequencing. c. Efficient iterative replacement of genomic sacB-$Cm^R$ with BAC bound rpsL-$Kan^R$ using REXER 2 and REXER 4. The rpsL-$Kan^R$ is integrated into the same genomic locus (between 89.061 and 89,587) as clones from (b) using REXER 2 and REXER 4. 11 colonies each from REXER 2 and REXER 4 were correct by phenotype, colony PCR, and DNA sequencing. d. Iteration of REXER to replace 220 kb of the genome with 230 kb of synthetic DNA. LuxA, B, C. D, E are the five genes for the lux operon (FIG. 1), hph is the hygromycin B phosphotransferase gene which confers resistance to hygromycin B. e. Following the phenotype of cells through rounds of REXER. The parental cell line (genome$^{wt}$), two independent clones from the $1^{st}$ round of REXER (clone A and B), and two independent clones from the $2^{nd}$ round of REXER (clone C and D) were plated on LB agar supplemented with indicated antibiotics or sucrose to check the phenotype of different marker combinations. Clones from the $2^{nd}$ round of REXER (clone C and D) retained the luminescent phenotype from the $1^{st}$ round of REXER (clone A and B) and gained the new phenotype of hygromycin B resistance conferred by hph gene f. Following the genotype of cells through rounds of REXER. Colony PCRs were performed for all five clones from (e) using primers specific for or flanking each of the introduced genomic components in the $1^{st}$ and $2^{nd}$ rounds of REXER.

FIG. 10 (Supplementary FIG. 3) shows Design for systematic and defined synonymous codon reassignment in an operon of the E. coli genome rich in essential genes that express interacting proteins. a. The codon-anticodon interactions for E. coli serine, leucine, and alanine decoding boxes, and recoding schemes (r.s) for synonymous codon reassignment. Lines indicate codon-anticodon interactions. Grey lines indicate decoding events removed in the target region by synonymous recoding. Codons targeted for removal are shown in grey (dark grey pre-removal and light grey post-removal), and their replacements are shown in pink. Arrows link the codons targeted for removal with their best matching replacements as determined by cAi, tAi, or t.E. Application of one of these recoding schemes genome-wide would allow the targeted codons to be completely removed from E. coli genome, which will make tRNAs with corresponding anticodons redundant. Deletion of these redundant tRNAs in the recoded genome will eliminate natural decoding of the targeted codons, which can then be redefined to cleanly encode unnatural amino acids. b. Identifying a target operon rich in target codons and essential genes. To identify the best candidate region to test our synonymous recoding schemes, we focused on regions that contain a large number of essential genes as well as large numbers of the codons targeted for recoding. Essential and non-essential genes were identified based on their corresponding absence and presence in the KEIO knockout collection. The positions of all genes were mapped on to the MDS42 genome, with essential genes coloured in black and non-essential genes in white. The number of targeted serine, leucine, or alanine codons in all essential genes within a 10 kb sliding window of the MDS42 genome were counted by iteratively shifting the window by 100 nt and performing the codon count from the first 10 kb of the MDS42 genome sequence until the end. The mraZ to ftsZ region (coloured in red), which corresponds to the cell division operon, was identified as the highest scoring 20 kb region across MDS42 genome for all targeted codons (serine codons TCG and TCA, leucine codons TTG and TTA, or alanine codons GCG and GCA). c. Position and density of targeted codons in the chosen mraZ to ftsZ region. The mraZ to ftsZ region (from 89,062 to 106,507) was refactored[2] by duplicating the five overlapping open reading frame sequences, creating duplicated region (d.r.) 1 to 5, to prevent the recoding of the upstream overlapping open reading frame from affecting the recoding of downstream open reading frame. The refactored region was then synthesized de novo with the systematic recoding defined by each recoding scheme. The position of all the targeted sense codons (coloured in red. 82 serine TCC and TCA codons. 156 leucine TTG and TTA codons, and 373 alanine GCG and GCA codons), the only TAG amber stop codon in the region (stop codon of murF, targeted for reassignment to TAA and coloured in red), and d.r.1 to 5 (coloured in pink with red outline) are mapped on to the mraZ to ftsZ region (background colour grey).

FIG. 11 (Supplementary FIG. 4) shows REXER enables the testing of systematic and defined synonymous codon reassignment in an operon of the E. coli genome rich in essential genes that express interacting proteins. a. Using REXER to replace the essential mraZ to ftsZ region with de novo designed and synthesized sequence. The sequences for the systematically recoded mraZ to ftsZ region were de novo designed and synthesized and carried on BACs with the second double selection cassette (−2 is sacB, and +2 is $Cm^R$) according to the REXER design. The first double selection cassette (−1 is rpsL, and +1 is $Kan^R$) was inserted between the E. coli chromosomal copy of mraZ and the upstream cra. REXER was performed and clones selected for the simultaneous gain of the synthetic sequence and loss of original genomic sequence between HR1 and HR2 by simultaneous selection for the gain of +2 (gain of resistance to chloramphenicol) and loss of −1 (loss of sensitivity to streptomycin). b. Individual recoding landscapes of the 16 post-REXER clones from serine r.s.1. The genomic regions between HR1 and HR2 of 16 post-REXER clones from serine r.s.1 (TCG and TCA to AGT) were fully sequenced. All 16 clones had lost the first double selection cassette between HR1 and mraZ and gained the second double selection cassette between ftsZ and HR2, indicating 100% replacements on both the 5' and 3' ends. All clones were chimera between wildtype sequence and recoded sequence. For each clone, the identity of codon at each of the 83 attempted recoding position and the d.r.1 to 5 was identified either as recoded with a binary value of 1 and coloured in red, or wildtype with a value of 0 and coloured in black. The distribution of targeted positions that are recoded and that remain wildtype across the refactored mraZ to ftsZ region give a "recoding landscape" for individual clones. c. Compiled recoding landscape of serine r.s.1. The individual recoding landscape of the post-REXER clones of serine r.s.1 were combined to generate the compiled recoding landscape of serine r.s.1 by counting the fraction of clones being recoded at each targeted position across the whole region. When the recoding fraction at a given position is greater than 0 (coloured in red), it indicates that there is at least one sequenced clone being recoded at this position. When the recoding fraction is zero (coloured in black), it indicates that the wildtype codon always remains and that the recoded codon may not be tolerated at these positions. No single clone was fully recoded across all the targeted codon positions using serine r.s.1. The compiled recoding landscape reveals a single position at which the wild type sequence is always maintained, codon 407 in ftsA.

FIG. 12 (Supplementary FIG. 5) shows Compiled recoding landscapes of targeted serine, leucine, and alanine codons reveal dramatic differences in the viability of defined and systematic synonymous recoding schemes. a. Recoding landscapes of targeted serine codons. The recoding landscapes of targeted serine codons reassigned by r.s.1 to 3 are calculated based on complete sequencing of the nraZ to ftsZ region from 16 individual clones. Serine r.s.1 (based on cAi) yielded no fully recoded clones and revealed a single position at which the wild type sequence is maintained, codon 407 in ftsA. Serine r.s.2 (based on tAi) and r.s.3 (based on t.E) both yielded 14 out of 16 clones (88%) as fully recoded. b. Recoding landscapes of targeted leucine codons. Leucine r.s.4 (based on cAi), r.s.5 (based on tAi), and r.s.6 (based on t.E) all failed to yield any fully recoded clones. While leucine r.s.4 and r.s.5 both have long stretch in which the wildtype sequence is maintained, r.s.6 has a comparatively much shorter fail-to-recode stretch spanning the d.r.5 plus two targeted codon positions downstream. c. Recoding landscapes of targeted alanine codons. 12 out of 16 clones (75%) from alanine r.s.7 (based on cAi) were fully recoded at all the 374 positions across the 20 kb region. However, alanine r.s.8 (consistent with both tAi and t.E) failed catastrophically with no single clone fully recoded and the longest fail-to-recode stretch.

FIG. 13 (Supplementary FIG. 6) shows Identifying and fixing a deleterious sequence in defined and systematic synonymous recoding. a. Recoding codon 407 in ftsA in the wildtype genomic background. The wildtype codon at ftsA codon position 407 is the serine codon TCG, which remained unchanged in all 16 post-REXER clones from serine r.s.1 (TCG and TCA to AGT). Attempts to change ftsA 407 from TCG to AGT also failed in the wildtype background, while recoding from TCG to TCT worked on all 20 characterized post-REXER clones (100%). b. Fixing the deleterious ftsA 407 AGT to AGC revived serine r.s.1. The compiled recoding landscape of serine r.s.1 with ftsA 407 as AGT is plotted in red, revealing the single position at which the wild type sequence is maintained, codon 407 in ftsA. The compiled recoding landscape of serine r.s.1 with ftsA 407 AGT changed to AGC (as in serine r.s.2 and r.s.3) is plotted in orange, overcoming the deleterious effect of ftsA 407 AGT. c. Changing ftsA 407 AGT to AGC in the serine r.s.1 background dramatically improved the recoding at this particular position from 0% to 100% d. Changing ftsA 407 AGT to AGC in the serine r.s.1 background dramatically improved the fraction of fully recoded clones across the entire 20 kb region from 0% to 94% (15 out of 16 clones). e. The fixed serine r.s.1 with ftsA 407 AGC yielded clones with no measurable growth defect. The doubling times of fully recoded clones from serine r.s.1 with ftsA 407 AGC, from serine r.s.2, serine r.s.3, and alanine r.s.7 are measured, and show no measurable growth defects when compared to the wildtype MDS42 E. coli control with the second double selection cassette integrated at the same genomic locus.

FIG. 14 (Extended Data FIG. 6) shows Genome Stepwise interchange Synthesis (GENESIS). The ability to replace 100 kb of the genome with synthetic DNA in a single round of REXER and the ability to iterate REXER. by using the product of one step as the direct template for the next step, will enable Genome Stepwise Interchange Synthesis (GENESIS) and replacement of the entire E. coli genome with synthetic DNA in around 40 steps.

FIG. 15 (Extended Data FIG. 7) shows The codons targeted in this work for removal and systematic replacement with defined synonymous codons over 20 kb of interacting and essential genes. a. Codon and anticodon interactions in the E. coli genome. 28 sense codons are highlighted in grey, along with the amber stop codon. The genome wide removal of these sense codons, but not other sense codons, would enable all their cognate tRNA to be deleted without removing the ability to decode one or more sense codons remaining in the genome. This is necessary but not sufficient for the reassignment of sense codons to unnatural monomers. Serine, leucine and alanine codon boxes are highlighted because the endogenous aminoacyl-tRNA synthetases for these amino acids do not recognize the anticodons of their cognate tRNAs. This may facilitate the assignment of codons within these boxes to new amino acids through the introduction of tRNAs bearing cognate anticodons that do not direct misaminocylation by endogenous synthetases. These considerations led us to focus on serine, leucine and alanine codons for reassignment. The number of total codon counts for all 64 triplet codons in the MDS42 genome (GenBank accession no. AP012306), all known codon-anticodon interactions through both Watson-Crick base-paring and wobbling, base modification on tRNA anticodons, tRNA genes, and measured in vivo tRNA relative abundance are reported. This analysis identifies 10 codons from the serine, leucine, and alanine groups (serine codon TCG, TCA, AGT, AGC; leucine codon CTG, CTA, TTG, TTA; and alanine codon GCG, GCA) satisfy both the codon-anticodon interaction and aminoacyl-tRNA synthetases recognition criteria for codon reassignment. b. Four serine codons (TCG, TCA, AGT, AGC) are chosen in three different combinations for genome wide removal by recoding them to alternative serine synonymous codons following defined recoding schemes. After their genome wide removal, all their matching tRNAs (also highlighted in grey) would be rendered redundant in the newly de novo designed and synthesized E. coli with the recoded genome, and thus can be deleted. After the deletion of the matching tRNAs, there would be no endogenous components to recognize and encode these targeted codons any more, and these targeted codons can then be re-introduced and reassigned to cleanly encode for u.a.a. c. Four leucine codons (CTG. CTA, TTG. TTA) are chosen in three different combinations for genome wide removal by recoding them to alternative leucine synonymous codons using defined recoding schemes following the same logic as discussed for the four serine targeted codons in (b). d. Two alanine codons (GCG. GCA) are chosen in for genome wide removal by recoding them to alternative alanine synonymous codons using defined recoding schemes following the same logic as discussed for the four serine targeted codons in (b) and the four leucine targeted codons in (c).

FIG. 16 (Extended Data FIG. 8) shows Generating compiled recoding landscapes from multiple individual recoding landscapes of the 20 kb generated by REXER with each systematically applied well-defined recoding scheme. The individual recoding landscapes of the 16 fully sequenced clones from different recoding schemes were derived as described in FIG. 3b and compiled into compiled recoding schemes as described in FIG. 3c. Panel (a) reflects data from r.s.2, (b) from r.s.3, (c) from r.s.4, (d) from r.s.5, (e) from r.s.6, (f) from r.s.7, (g) from r.s.8, and (h) from r.s.1 with ftsA codon 407 changed from AGT to AGC (highlighted in orange).

Figure 2:
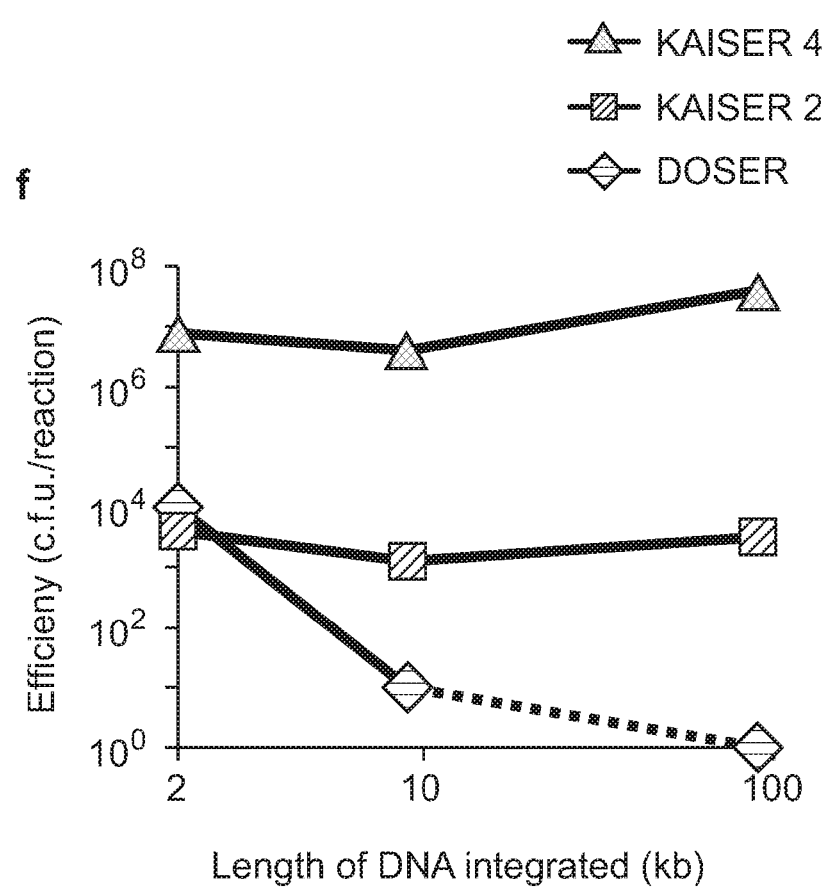
FIG. 2 shows Kai's Enhanced Recombination (KAISER) (sometimes referred to as 'REXER' (replicon excision enhanced recombination)); efficient, length independent, locus specific insertion of synthetic DNA into the E. coli genome. a. KAISER 2 and KAISER 4, two versions of KAISER that integrate DOSER with in vivo excision of synthetic dsDNA from an episomally maintained bacterial artificial chromosome (BAC). In KAISER 2, HR1/HR2 in the BAC are flanked by two CRISPR protospacer sequences, highlighted in blue and orange respectively. CRISPR/Cas9 cleavage at the positions specified by the protospacers, leads to excision of dsDNA from the BAC between HR1 and HR2, this dsDNA undergoes lambda red mediated recombination, leading to insertion between HR1 and HR2 in the genome. The BAC holds an extra copy of −1 in its backbone, and the selection for the loss of −1 ensures no surviving cells will carry the BAC. KAISER 4 augments KAISER 2 by adding two extra protospacers flanking the genomic hound −1/+1 cassette. All four protospacers (in the BAC and the genome) are then targeted for CRISPR/Cas9 mediated cleavage and lambda red mediated recombination. b. KAISER 2 and KAISER 4 are dependent on the CRISPR/Cas9 system and recombination. Integration of sacB-$Cm^R$ by KAISER 2, and KAISER 4 at the specific genomic locus marked by the rpsL-$Kan^R$ cassette was demonstrated by the loss of kanamycin resistance and gain of chloramphenicol resistance, and was confirmed by colony PCR. Control experiments omit either spacer RNA or lamda red beta. The data show the mean of three independent experiments, and the error bars represent the standard deviation. c. KAISER 2, and KAISER 4 give 100% integration at the target locus. The data show the mean of three independent experiments, and the error bars represent the standard deviation. Experiment performed as described in (b). d. Efficient integration of 9 kb synthetic DNA into the target locus of the *E. coli* genome using KAISER 2 and KAISER 4. A synthetic lux operon, with the coupled sacB-$Cm^R$ is integrated into the genomic locus (between 89,061 and 89.587) marked with rpsL-$Kan^R$ using KAISER 2 and KAISER 4. The 10-fold dilution double selection plates for KAISER 2 and the $10^4$-fold plates for KAISER 4 were imaged with white light to show surviving colonies. Every surviving colony shows bioluminescence. 11 colonies each from KAISER 2 and KAISER 4 were shown to be correct by phenotype, colony PCR and DNA sequencing. e. Efficient integration of 90 kb synthetic DNA into *E. coli* genome at a target locus using KAISER 2 and KAISER 4. 90 kb of synthetic DNA was constructed using 80 kb of *E. coli* MG1655 DNA, which is deleted from the MDS42 genome. The lux operon was integrated in the middle of this 80 kb region, and a sarB-$Cm^k$ cassette appended to one end. The 90 kb construct is carried on a BAC and integrated into the same genomic locus as in (d); characterization as in (d). f. Efficient length-independent integration with KAISER 2 and KAISER 4. Number of colony forming units (c.f.u.) per reaction is plotted against the length of integrated synthetic DNA for DOSER, KAISER 2, and KAISER 4. All experiments are performed using the same double selection plates under the same conditions. The 90 kb point for DOSER reflects the fact that it was not possible to obtain a 90 kb linear dsDNA product in vitro, rather than the efficiency or recombination per se. It is well established that classical recombination efficiency falls off rapidly with DNA length.

Extended Data Table 4 shows Defining recoding rules by codon adaptation index (cAi), tRNA adaptation index (tAi), and translation efficiency (t.E). We defined the best synonymous replacements for the target serine codons by identifying the closest match for the target codons, as judged by either codon adaptation index (cAi), tRNA adaptation index (tAi), or a third metric that combines codon abundance and measured tRNA concentrations to estimate translation efficiency (t.E) (see Methods). The table assigns the closest substitutions (in pink) for synonymous recoding of TCA$^{Ser}$ and TCG$^{Ser}$ (in grey) using the three coding metrics. The number in bold is the value of the best matching substitution in a given coding metric.

EXAMPLES

Methods

Reference is made to general molecular biological techniques such as those taught in Ausubel et al (Short Protocols in Molecular Biology: A Compendium of Methods from Current Protocols in Molecular Biology by Frederick M. Ausubel (Editor). Roger Brent (Editor), Robert E. Kingston. David D. Moore (Editor) Published by John Wiley & Sons ISBN: 047132938X) and/or Green and Sambrook (2012 Molecular Cloning—A Laboratory Manual by Michael R Green and Joseph Sambrook Published by Cold Spring Harbour Laboratory Press ISBN: 978-1-1936113-42-2).

Construction of Selection Cassettes, Cell Strains, and Plasm Ids

Two double selection cassettes were constructed. The −1/+1 is a fusion between the negative selection marker rpsL as −1 encoding the essential ribosomal protein S12 and conferring sensitivity to streptomycin in rpsLK43R genomic background, and the positive selection marker Kan$^R$ as +1 encoding the kanamycin resistance gene neomycin phosphotransferase II. The rpsL-Kan$^R$ cassette was expressed as two separate proteins from a single mRNA driven by constitutive transcription from wildtype rpsL promoter. The −2/+2 is a fusion between the negative selection marker sacB as −2 conferring sensitivity to sucrose, and the positive selection marker Cm$^R$ as +2 encoding the chloramphenicol resistance gene chloramphenicol acetyl transferase. The sacB-Cm$^R$ cassette is expressed as two separate proteins from a single mRNA driven by constitutive transcription from EM7 promoter. Both selection cassettes are synthesized de novo.

The minimum genome E. coli strain MDS42 was used as the starting strain[15]. A K43R mutation was introduced into the rpsL gene of MDS42 to create MDS42$^{rpsLK43R}$ by classical recombination and selection for streptomycin resistance. The resulting MDS42$^{rpsLK43R}$ is resistant to streptomycin in the absence of additional wildtype copy of rpsL, and sensitive to streptomycin in the presence of any additional copy of wildtype rpsL. Then the −1/+1 cassette rpsL-Kan$^R$ is inserted between 89.061 and 89,587 in MDS42$^{rpsLK43R}$ genome to create MDS42$^{rK}$ by classical recombination and confirmed by colony PCR using primers flanking genomic position 89,061 and 89.587.

pCDFtet_pAraRedCas9_tracrRNA was constructed by assembling multiple PCR fragments using Gibson Assembly. The plasmid backbone and replication origin is from pCDFDuet-1 plasmid (from Addgene), in which the spectinomycin resistance marker is replaced with tetracycline resistance marker from pBR322 plasmid (from New England BioLab). The araC gene, the arabinose promoter (pAra), and the lambda red (alpha/beta/gamma) genes are PCR amplified from pRed/ET plasmid (from GeneBridges) The open reading frame of Cas9 is PCR amplified from pCas9 plasmid[16] and placed downstream of the lambda red alpha such that lambda red gamma, lambda red beta, lambda red alpha, and the Cas9 are expressed as four individual proteins from a single mRNA driven by pAra in the presence of arabinose. The tracrRNA with its endogenous promoter was PCR amplified from pCas9 plasmid[16], and placed in the same orientation downstream of the araC gene. The finished pCDFtet_pAraRedCas9_tracrRNA plasmid was verified by sequencing. The pCDFtet_pAraRed(Δβ)Cas9_tracrRNA was derived from pCDFtet_pAraRedCas9_tracrRNA by inserting GTAC between the 314$^{th}$ and 315$^{th}$ nucleotide of lambda red beta open reading frame, which leads to frame shifting in the translation and thus inactivation of lambda red beta.

pMBlamp_Spacer0 was constructed by assembling two PCR fragments using Gibson Assembly Master Mix (from New England BioLab). The pMB1 replication origin and ampicillin resistance marker were PCR amplified from pBR322 plasmid (from New England BioLab). The CRISPR array with no functional spacer RNA (hence the nomenclature 0) between BamHI and EcoRI was PCR amplified from pCRISPR[16]. The finished pMBlamp_Spacer0 was verified by sequencing. CRISPR arrays with two or four different spacer RNA sequences for directing KAISER 2 or KAISER 4 respectively with interspaced direct repeats were ordered commercially as synthesized DNA and cloned into pMBlamp_Spacer0 to replace the empty CRISPR array between BamHI and EcoRI to create different functional pMBlamp_Spacers$^{×2}$ or pMBlamp_Spacers$^{×4}$ plasmids. The final pMBlamp_Spacers plasmids were sequence verified by Sanger sequencing. A related version of pMBlerm_Spacers plasmids was prepared replacing the ampicillin resistance marker in pMBlamp_Spacers with erythromycin resistance marker.

The BAC holding the synthetic DNA was constructed by assembling multiple fragments. The BAC backbone is based on pBeloBAC11 (from New England BioLab) from nucleotide 1542 to 7041 with the addition of the double selection cassette −2/+2 and the negative selection marker −1, and assembled using Gibson Assembly Master Mix (from New England BioLab). An alternative arrangement utilises −1/+1 coupled with −2. The BAC backbone for holding long synthetic DNA (20 kb or longer) also incorporates a Saccharomyces cerevisiae replication centromere CEN and selection marker URA3 (from S. cerevisiae vector pRS316) for assembly, selection and amplification in S. cerevisiae. The synthetic DNA was always flanked by AvrII sites, which also function as PAM and part of protospacer for CRISPR/Cas9 to guide excision of synthetic DNA in KAISER 2 and KAISER 4.

Assembling Short Synthetic DNA onto BAC Using Gibson Assembly

The pBAC_HR(89.061)-sC-HR(89.587)_r was constructed by assembling three PCR fragments using Gibson Assembly: the first fragment being the 2.2 kb long −2/+2 sacB-Cm$^R$ cassette flanked with HR1 (89,012-89,061, all numbering is from the MG1655 reference sequence) and HR2 (89.587-89.636) and further flanked with two AvrII sites, the second fragment being the −1 rpsL gene with rrnC terminator, and the third fragment being the pBeloBAC11 backbone from nucleotide 1542 to 7041. The successfully assembled pBAC_HR(89,061)-sC-HR(89.587)_r was selected on LB agar plates with 18 μg/ml chloramphenicol and sequence verified by Sanger sequencing. The pBAC_HR(89,061)-rK-HR(89,587)_s was constructed in a similar way using −1/+1 rpsL-Kan$^R$ cassette flanked with HR1(89.012-89,061) and HR2(89,587-89,636) and further flanked with two AvrII sites. −2 sacB gene with rrnC terminator, and the pBcloBACII backbone. The pBAC_HR (89,061)-T5Lux-sC-HR(89,587)_r was constructed by inserting a PCR product of an artificial lux operon between the HR1 and the −2/+2 sacB-Cn cassette in the pBAC_HR (89,061)-sC-HR(89,587)_r. The total length of the artificial lux operon plus the −2/+2 sacB-Cm$^R$ cassette is around 9 kb.

Assembling Long Synthetic DNA onto BAC Using Recombination in S. cerevisiae

Long synthetic DNA fragments (≥20 kb) were assembled by in vivo recombination in S. cerevisiae. The pBeloBAC11 backbone was converted into a BAC/YAC shuttle vector by introducing a S. cerevisiae replication centromere CEN and URA3 selection marker (from S. cerevisiae vector pRS316 from Addgene). The BAC/YAC shuttle vector holding long synthetic DNA was assembled from 5-16 DNA fragments by in vivo recombination in S. cerevisiae's. The DNA fragments were designed to overlap each other by 38-45 bp for recombination and the fragments are generated by PCR or restriction digestion. Uracil-auxotroph S. cerevisiae (strain BY4741) cells were digested with zymolyase to obtain highly competent spheroblasts and transformed with 60 fmol of each DNA fragment. Cells were recovered in uracil-free agar at 30° C. for three days and then genotyped by colony-PCR. Clones with correctly assembled BAC/YAC were grown in uracil-free media and the constructs were extracted by treatment with zymolyase and SDS, followed by isopropanol precipitation[18].

The pBAC_HR(89,061)-20 kb-sC-HR(106.508)_r for 20 kb genomic recoding was assembled from five fragments: a 7 kb PCR fragment of URA3-pBAC-HR1(89,061), a 3.7 kb PCR fragment of sacB-Cm$^R$-HR2(106,508)-rpsL-CEN, and three AvrII-digested fragments (2 to 9 kb) of synthetic DNAs constituting the 20 kb recoded sequence corresponding to the MDS42 genomic region 89.062 to 192,743, in which all TCA$^{Ser}$, TCG$^{Ser}$ and TAG amber are recoded to their synonyms. A total of 83 codons and 247 nt were recoded in each 20 kb synthetic sequence. All five fragments were designed to overlap each other with 38 bp for recombination in S. cerevisiae.

The pBAC_HR(89,061)-90 kb/Lux-sC-HR(89.587)_r for 90 kb insertion was assembled as above from 13 fragments: a 7 kb PCR fragment of URA3-pBAC-HR1(89,061), a 3.7 kb PCR fragment of sacB-Cm$^R$-HR2(106,508)-rpsL-CEN, and eight 10 kb PCR-fragments of E. coli DH 10b genomic DNA (1,398,251 to 1,480,230) and the lux operon.

The pBAC_HR(89,061)-100 kb/Lux-sC-HR(192.744)_r for 100 kb genomic replacement was assembled as above from 17 fragments: a 7 kb PCR fragment of URA3-pBAC-HR1(89,061), a 3.7 kb PCR fragment of sacB-Cm$^R$-HR2 (106,508)-rpsL-CEN, ten 10 kb PCR fragments of E. coli MDS42 genomic DNA (89,062 to 192,743), and five PCR fragments of luxA, B, C, D, E genes flanked by 45 bp overlaps for recombination.

Classical Recombination and DOSER Protocol

The sacB-Cm$^R$ cassette was PCR amplified using primers with HR1 and HR2 attached to the 5 end correspondingly. The purified linear dsDNA has the sacB-Cm$^R$ cassette in the middle flanked by HR1 and HR2 on each end.

In classical recombination, 3 µg of this linear dsDNA holding sacB-Cm$^R$ cassette was transformed into 100 µl of electro-competent MDS42$^{rK}$ cells, which are pre-transformed with the pRed/ET plasmid and induced to express the λ Red components. The cells were recovered in 4 ml SOB media for 1 hour at 37° C. and then diluted to 100 ml LB and incubated for 4 hours at 37° C. with shaking. The culture was then spun down and re-suspended in 4 ml of LB and spread in serial dilutions on selection plates of LB agar with 18 µg/ml chloramphenicol.

In DOSER, 3 µg of the same linear dsDNA holding sacB-Cm$^R$ cassette was transformed into 100 µl of electro-competent MDS42$^{rK}$ cells, which is pre-transformed with the pRed/ET plasmid and induced to express the λ Red components. The cells were recovered in 4 ml SOB media for 1 hour at 37° C. and then diluted to 100 ml LB and incubated for 4 hours at 37° C. with shaking. The culture was then spun down and re-suspended in 4 ml LB and spread in serial dilutions on selection plates of LB agar with 18 µg/ml chloramphenicol and 50 µg/ml streptomycin.

Multiple colonies from classical recombination and DOSER were picked for colony-PCR using primer pair (craf and mraZr) flanking the genomic locus 89,061 to 89,587. Four out of eight colonies from classical recombination showed a higher band corresponding to replacement of genomic rpsL-Kan$^R$ with sacB-Cm$^R$ at this defined genomic locus, and the other four showed the PCR band corresponding to a genomic rpsL-Kan$^R$ at this locus. All eight colonies from DOSER showed PCR band corresponding to genomic sacB-Cm$^R$ replacing rpsL-Kan$^R$ at this locus. Colony-PCRs from MDS42$^{rK}$, MDS42$^{rpsLK43R}$, and Milli-Q filtered water with no resuspended colony were included as controls. All PCR products were run in parallel to NEB 2-Log DNA Ladder (from New England BioLab). All colony PCR products were purified using QIAGEN PCR purification column, and sequence verified by Sanger sequencing KAISER Protocol MDS42$^{rK}$ cells were double transformed with pCDFtet_pAraRedCas9_tracrRNA and pBAC_HR(89,061)-sC-HR(89.587)_r and plated on LB agar plates supplemented with 2% glucose, 10 µg/ml tetracycline and 18 µg/ml chloramphenicol. Individual colonies were picked and inoculated into LB media with 10 µg/ml tetracycline and 18 µg/ml chloramphenicol, and grown overnight at 37° C. with shaking. The overnight culture was diluted in LB media with 10 µg/ml tetracycline and 18 µg/ml chloramphenicol to OD$_{600}$=0.05 and grown at 37° C. with shaking for around 3 hours until OD$_{600}$≈0.3. Arabinose powder was added to the culture to reach a final concentration of 0.5% and the culture was incubated for one additional hour at 37° C. with shaking. The cells were harvested at OD$_{600}$≈0.6, and made electro-competent in $\frac{1}{500}^{th}$ of the culture volume.

3 µg pMBlamp_Spacers$^{\times 2}$ or pMBlamp_Spacers$^{\times 4}$ plasmid was electroporated into the pre-induced MDS42$^{rK}$ cell with pCDFtet_pAraRedCas9_tracrRNA and pBAC_HR(89,061)-sC-HR(89.587)_r. The cells were recovered in 4 ml SOB media for 1 hour at 37° C. and then diluted to 100 ml LB supplemented with 50 µg/ml ampicillin and 10 µg/ml tetracycline and incubated for 4 hours at 37° C. with shaking. The culture was spun down and re-suspended in 4 ml LB and spread in serial dilutions on selection plates of LB agar with 18 µg/ml chloramphenicol and 50 µg/ml streptomycin. The plates were incubated at 37° C. overnight, and the efficiency was calculated by counting viable colonies on the plates. Multiple colonies were picked, resuspended in Milli-Q filtered water, and arrayed on LB agar plates or LB agar plates supplemented with 18 µg/ml chloramphenicol, or supplemented with 50 µg/ml kanamycin. Colony-PCR was also performed from resuspended colonies using the primer pair (craf and mraZr) flanking the genomic locus 89,061 to 89,587 (FIG. 5 (Extended Data FIG. 1a,b)).

The resulting colonies with the −2/+2 sacB-Cm$^R$ cassette replacing the −1/+1 rpsL-Kan$^R$ cassette at the genomic locus 89.062 to 89.586 were incubated in LB without ampicillin, to lose the pMBlerm_Spacers$^{\times 2}$ or pMBlerm_Spacers$^{\times 4}$ plasmid. The resulting cells were double transformed with pCDFtet_pAraRedCas9_tracrRNA and pBAC_HR(89,061-rK-HR(89,587)_s and selected on LB agar plates supplemented with 2% glucose. 10 µg/ml tetracycline and 25 µg/ml kanamycin. An individual colony was picked and inoculated into LB media with 10 µg/ml tetracycline and 25 µg/ml kanamycin, and grown at 37° C. until OD$_{600}$≈0.3. Arabinose powder was added to the culture to a final concentration of 0.5% and the culture was incubated for one additional hour at 37° C. with shaking. The cells were harvested at OD$_{600}$≈0.6, and made electro-competent in $\frac{1}{500}^{th}$ of the culture volume. 3 µg pMBlerm_Spacers$^{\times 2}$ or pMBlerm_Spacers$^{\times 4}$ plasmid was electroporated into the pre-induced cell. The cells were recovered in 4 ml SOB media for 1 hour at 37° C. and then diluted to 100 ml LB supplemented with 100 µg/ml erythromycin and 10 µg/ml tetracycline and incubated for 4 hours at 37° C. with shaking. The culture was spun down and re-suspended in 4 ml LB and spread in serial dilutions on selection plates of LB agar with 3% sucrose and 25 µg/ml kanamycin. The plates were incubated at 37° C. overnight, and efficiency was calculated by counting viable colonies on the plates. Multiple colonies were picked, resuspended in Milli-Q filtered water, and arrayed on LB agar plates, or LB agar plates supplemented with 18 µg/ml chloramphenicol or 50 µg/ml kanamycin Colony-PCR was performed from resuspended colonies using the primer pair (craf and mraZr) flanking the genomic locus 89,061 to 89.587 (FIG. 5 (Extended Data FIG. 1a,c)). Our use of positive and negative selection markers in the DNA integrated into the genome allows the result of one round of KAISER to act as a template for the next round of KAISER (FIG. 5 (Extended Data Figure ta)). We anticipate that this will allow iterative genomic changes and re-synthesis of the genome in a small number of steps in a process we call Genome Stepwise Interchange synthesis (GENESIS) (FIG. 5 (Extended Data FIG. 1d)).

The pBAC_HR(89,061)-T5Lux-sC-HR(89,587)_r, pBAC_HR(89,061)-90 kb/Lux-sC-HR(89,587)_r, pBAC_HR(89,061)-100 kb/Lux-sC-HR(192,744)_r, and pBAC_HR(89,061)-20 kb-sC-HR(106,508)_r with matching pMBlamp_Spacers$^{\times 2}$ or pMBlamp_Spacers$^{\times 4}$ plasmids were used in the other KAISER experiments following the same protocol. Colony PCR of the lux operon and the coupled −2/+2 sacB-Cm cassette inserted at the genomic locus 89,061 to 89,587 using the primer pair (craf and mraZr) flanking the genomic locus generated a 9 kb band for successful insertion and 1.5 kb for the MDS42$^{rK}$ control. Colony PCR flanking the entire inserted or replaced region cannot be performed for 90 kb insertion or 100 kb replacement. Instead, primer pairs flanking the 5' or 3' end of the inserted/replaced DNA were used, which generates a PCR band for correct insertion/replacement, and no band or band of the wrong size with MDS42$^{rK}$ control. Colony PCR using primers for the internal watermarks were also performed, verifying the integrity of the inserted/replaced synthetic DNA. The 20 kb recoded region (from 89,062 to 106,507) was PCR amplified from purified genomic DNA using QIAGEN DNeasy Blood & Tissue Kit and primer pair (craf and lpxCr) flanking the whole region. The 20 kb PCR product was purified using Bio-Rad PCR Kleen Columns and fully sequenced by Sanger sequencing.

Choice of 20 kb Recoding Region

To identify the best candidate region to test our synonymous recoding schemes, we focused on regions that contain a large number of essential genes as well as large numbers of the codons targeted for recoding, specifically TCA$^{Ser}$ and TCG$^{Ser}$ and TAG amber. We applied a sliding window approach, in which we counted the number of target codons within all essential genes within a 10 kilobase region of the MDS42 genome. Starting from the first 10 kb of the genome sequence, we iteratively shifted the window by 100 nt and performed the codon analysis until the end of the MDS42 genome sequence. Gene essentiality was defined by absence from the KEIO collection, which identifies individually non-essential genes in E. coli[30].

Choice of Recoding Rules

We analysed the translation efficiency of the target codons TCA$^{Ser}$ and TCG$^{Ser}$ with the aim of identifying synonymous mutations that would minimally affect protein translation. Accordingly we characterised all serine codons using the codon adaptation index (cAi)[27] and the tRNA adaptation index (tAi)[28,29]. In case of cAi, we used the relative adaptiveness of each codon i (expressed as cAiw$_i$) as a metric. In case of tAi, we used the relative adaptiveness value of each codon i (expressed as tAiw$_i$) in Table S2 from the paper by Tuller et al.[28,29]. To identify the synonymous mutations that we expect to affect protein translation least, we compare cAiw$_i$ and tAiw$_i$ for codons TCA$^{Ser}$ and TCG$^{Ser}$ to the values of all remaining serine codons. We defined ideal substitutions such that the difference in cAiw$_i$ and tAiw$_i$ of the target and the substituted codon is minimal. Comparing cAiw$_i$ and tAiw$_i$ for all codons, we noticed that the two metrices do not correlate well (Pearson's $R^2$=0.24) and decided to propose a third metric that would integrate our assumptions about the translation efficiency of each codon. In particular, we speculated that translation efficiency increases proportionally with increasing isoacceptor tRNA concentration and decreases proportionally with increasing numbers of competing codons that am translated by the same isoacceptor tRNA. On this basis we defined the translation efficiency (t.E) of codon i as follows:

$$t.E_i = \sum_j \left( \frac{k_{ij} \times [tRNA_j]}{\sum_m q_m k_{mj}} \right),$$

$$k_{ij}, k_{mj} \in \begin{Bmatrix} \text{cognate: } 1.0 \\ G-U/U-G \text{ wobble: } 0.5 \\ C/U - xo^5U: 0.25 \\ C/U - \text{inosine: } 0.1 \\ A - \text{inosine: } 0.05 \end{Bmatrix},$$

where codon i is translated by tRNAs j, $k_{ij}$ denotes the interaction strength between codon i and tRNA j, m denotes each codon translated by tRNA j, and $k_{ml}$ denotes the interaction strength between codon m and tRNA j. The interaction strengths were defined in five groups: i) "cognate" for codons that are reverse complements to the respective tRNA anticodon as well as AUA$^{Ile}$-k$^2$CAU$^{tRNA}$, ii) "G-U/U-G wobble" for codons where a third position G or U interacts with a (modified) tRNA U or G, respectively, iii) "C/U-xo$^5$U" for codons where a third position C or U interacts with an xo$^5$-modified undine in the tRNA anticodon, iv) "C/U-inosine" where a third position C or U in the codon interacts with an inosine in the tRNA anticodon (an interaction shown to be 3-8-fold weaker than G-U wobbling[44]), and v) "A-inosine" for the reportedly weak interaction between the third position A in a codon with an inosine in the tRNA anticodon[45]. We obtained the tRNA concentrations [tRNA$_j$] from reported measurements performed on E. coli cultures, expressed as a fraction of tRNA out of total tRNA in percent[46]. To determine the relative transcriptomic codon frequency q for each codon i we first calculated the codon's absolute transcriptomic frequency $r_i$:

$$r_i = p_x g_{ix} \times t_x,$$

where $g_{ix}$ is the frequency of codon i in gene x and $t_x$ is the transcript abundance of gene x according to empirical data (DNA array data for wild type E. coli grown at 0.5 h$^{-1}$)[42]. Finally $r_i$ was transformed into $q_i$ by dividing $r_i$ by the maximal value found for r across all codons:

$$q_i = \frac{r_i}{\max(r)}.$$

Using the three coding metrics, we constructed Extended Data Table 4 by assigning the closest substitutions (in pink) for synonymous recoding of TCA$^{Ser}$ and TCG$^{Ser}$ (in grey).

Growth Rate Measurements and Analysis

Glycerol stocks of the assayed bacterial clones were used to inoculate 5 mL LB in absence of antibiotics for overnight incubation at 37° C. with shaking. The overnight cultures were used to inoculate triplicates of 1 mL of LB in a deep-well preculture plate at a ratio of 1:100, followed by incubation at 37° C. for 6 hours with shaking. Each replicate on the preculture plate is used to inoculate 200 μL of LB in a 96-well measurement plate at a ratio of 1:100. The measurement plate was incubated at 37° C. for 16 hours with shaking at 400 rpm in an M200 Pro Plate Reader (Tecan). Readings of OD$_{600}$ were taken for each well every 10 min. Plate reader absorbance data was adjusted to correspond to spectrophotometer readings by collecting measurements from a dilution series of bacterial cultures and fitting the plate reader data y with a polynomial to the spectrophotometer values x: y=2.053 $x^2$+2.2 x+0.061. Average and standard deviation were calculated across the triplicates and represented using the Matlab functions plot and errorbar.

Example 1: Genome as Target

To improve integration at a target locus for classical lambda red mediated recombination in E. coli, we first inserted a double selection cassette, −1/+1, a fusion between a negative selection marker (−1, rpsL, encoding the essential ribosomal protein S12 and conferring sensitivity to streptomycin) and a positive selection marker (+1, $Kan^R$, encoding the kanamycin resistance gene neomycin phosphotransferase II) into E. coli $MDS42^{rpsLK43R}$, which is insensitive to streptomycin. Integration of this cassette created E. coli $MDS42^{rK}$, in which rpsL-$Kan^R$ is integrated between 89.061 and 89,587 in $MDS42^{rpsLK43R}$.

We used a PCR product with synthetic DNA containing a second double selection cassette −2/+2, a fusion between a negative selection marker (−2, sacB, conferring sensitivity to sucrose) and a positive selection marker (+2, $Cm^R$, encoding the chloramphenicol resistance gene chloramphenicol acetyl transferase) for lambda red mediated recombination, targeting the region of rpsL-$Kan^R$ insertion in $MDS42^{rK}$ (FIG. 1a). Selection for integration of the PCR product on chloramphenicol led to 50% integration at the target locus, while selection for both chloramphenicol resistance and streptomycin resistance, resulting from both integration of the PCR product and replacement of the target locus, led to 100% integration at the target locus (FIG. 1b, c). We named this approach DOSER (double selection recombination) (FIG. 1). We conclude that the use of both positive and negative selection markers in DOSER can substantially increase integration of synthetic DNA at a target locus via recombination. We note that for a single insertion, a negative selection marker in the genome and a positive selection marker in the inserted sequence should be sufficient. However, our use of positive and negative selection markers in the DNA integrated into the genome allows the result of one round of recombination to act as a template for the next round of recombination (FIG. 5 (Extended Data FIG. 1a)). We anticipate that this will allow iterative genomic changes and, in combination with the developments described herein, re-synthesis of the genome in a small number of steps (FIG. 5 (Extended Data FIG. 1d)).

The efficiency of classical recombination protocols decreases drastically as a function of dsDNA length. The overall efficiency is the product of the transformation efficiency for linear dsDNA and the efficiency with which the linear dsDNA mediates intracellular recombination. We hypothesized that the decrease in efficiency of classical recombination for long linear dsDNA results from challenges in efficiently delivering dsDNA into cells, and we therefore investigated routes for generating linear dsDNA for recombination in vivo.

Example 2: BAC

We created a bacterial artificial chromosome (BAC) in which the −2/+2 cassette is flanked by HR1 and HR2 sequences and Cas9 target sites (containing protospacer-PAM sequences), and transformed this BAC into E. coli $MDS42^{rK}$ expressing lambda red (alpha/beta/gamma)[14], $Cas9^{16}$, and $tracrRNA^{16}$, creating a population of cells in which every cell contains the BAC and a Cas9 system poised for activation upon addition of spacer RNAs (FIG. 2a). Addition of a plasmid, encoding spacer RNAs targeting the protospacers[16] within the BAC target sites, and selection for the gain of resistance to both chloramphenicol (gain of +2) and streptomycin (loss of −1 from the genome, and loss of the backbone of the BAC) led to replacement of the sequence between HR1 and HR2 in the genome, with the sequence between HR1 and HR2 from the BAC (FIG. 5 (Extended Data FIG. 1b)).

The genomic replacement was strictly dependent on the CRISPR/Cas9 system, and components of lambda red recombination machinery (FIG. 2b), and was targeted to the desired genomic locus (FIG. 2c). Our data are consistent with the CRISPR/Cas9 mediated excision of the dsDNA between HR1 and HR2 in the BAC, and lambda red mediated integration of this sequence between HR1 and HR2 in the genome. We named our approach KAISER 2 (Kai's enhanced recombination, two cuts).

To investigate the dependence of KAISER 2 on the length of DNA inserted into the genome, we created a BAC with 9 kb or 90 kb of DNA inserted between HR1 and −2/+2 (FIG. 2d, e, f). The 9 kb insertion contains a designed luxABCDE operon derived from Photorhabdus luminescens[17], which is necessary and sufficient to generate bioluminescence in E. coli. We transformed this BAC into E. coli $MDS42^{rK}$ and implemented the KAISER 2 protocol. All cells selected on chloramphenicol and streptomycin integrated the lux operon at the correct locus (between 89.061 and 89,587), and were bioluminescent (FIG. 2d). Moreover, while the efficiency of DOSER, and classical recombination, drops dramatically from $10^4$ colony forming units (c.f.u.) for a 2 kb insertion to less than 10 c.f.u. for a 9 kb insertion (FIG. 2f) the efficiency of KAISER 2 is constant, at $10^4$ c.f.u. for 2 kb or 9 kb insertions.

Example 3: Very Large Nucleic Acid Insertions

To test the integration of longer DNA via KAISER 2 we designed a new insert in which the lux operon from P. luminescens is placed in the middle (between 1.439.005 and 1,439,006) of 80 kb of DNA from E. coli MG1655 (1,398, 251 and 1,480,230, previously deleted in creating $MDS42^{15}$). This led to a 90 kb insert that was assembled into the BAC between HR1 and −2/+2, via homologous recombination in S. cerevisiae[18]. We implemented KAISER 2 with the resulting BAC to integrate the 90 kb of synthetic DNA into the genome of $MDS42^{rK}$. All cells selected on chloramphenicol and streptomycin integrated the lux operon at the correct locus (between 89.061 and 89,587), were bioluminescent, and contained the entire insert (FIG. 2e). Moreover, the efficiency of KAISER 2 is maintained, at $10^4$ c.f.u. for a 90 kb insertion (FIG. 2r). We conclude that KAISER 2 provides the first route to efficient, length independent insertion of very long synthetic DNA into target genomic loci in E. coli.

Example 4: KAISER 4

Next we asked whether the overall efficiency of KAISER 2 could be improved by creating double strand breaks in the genome between HR1 and HR2 (FIG. 2a), leading to a total of 4 cuts (two in the BAC and two in the genome). To achieve this process, which we named KAISER 4, we transformed the BAC containing −2/+2 between HR1 and HR2 into E. coli $MDS42^{rK}$ expressing lambda red (gamma/beta/alpha), Cas9, and tracrRNA, creating a population of cells in which every cell contains the BAC and a Cas9 system poised for activation upon addition of spacer RNAs. We added a plasmid encoding four spacer RNAs, two spacer RNAs directed to the BAC target sites, as in KAISER 2, and two additional spacer RNAs directed between HR1 and HR2 in the genome, and selected for the gain of resistance to both chloramphenicol (gain of +2) and streptomycin (loss of −1 from the genome, and loss of the backbone of the BAC). This selection led to replacement of the sequence between HR1 and HR2 in the genome, with the sequence between HR1 and HR2 from the BAC (Extended Data FIG. 1b), and destruction of all four protospacers. KAISER 4 yielded $10^7$ c.f.u, was strictly dependent on both the CRISPR Cas9 system and the lambda red recombination machinery (FIG. 2b), and led to integration at the correct locus (FIG. 2c). To investigate the length dependence of KAISER 4 we repeated the 9 kb and 90 kb insertion using the KAISER 4 strategy (FIG. 2d,e). The efficiency of KAISER 4 was length independent and yielded $10^3$ times more c.f.u. than KAISER 2 for all integrations (FIG. 2f). These results demonstrate that the genomic cuts in the KAISER 4 strategy further increase the efficiency of synthetic DNA insertion with respect to KAISER 2, while maintaining insertion at the correct locus.

Example 5: 100 Kb Insertions/Replacements

Next, we demonstrated that KAISER 2 and KAISER 4 allow us to efficiently replace 100 kb of the *E. coli* genome. We targeted the region from mraZ to pyrH (89,062 to 192.743) for replacement. We defined a 50 nucleotide HR1 sequence (from 89.012 to 89,061, immediately 5' of the target region), and we inserted the −1/+1 selection cassette immediately Y to HR1 in the genome (between 89,061 and 89,062). We defined a 63 nt sequence 100 kb downstream of this HR1 in the genome as HR2 (from 192.744 to 192,806).

Figure 3:
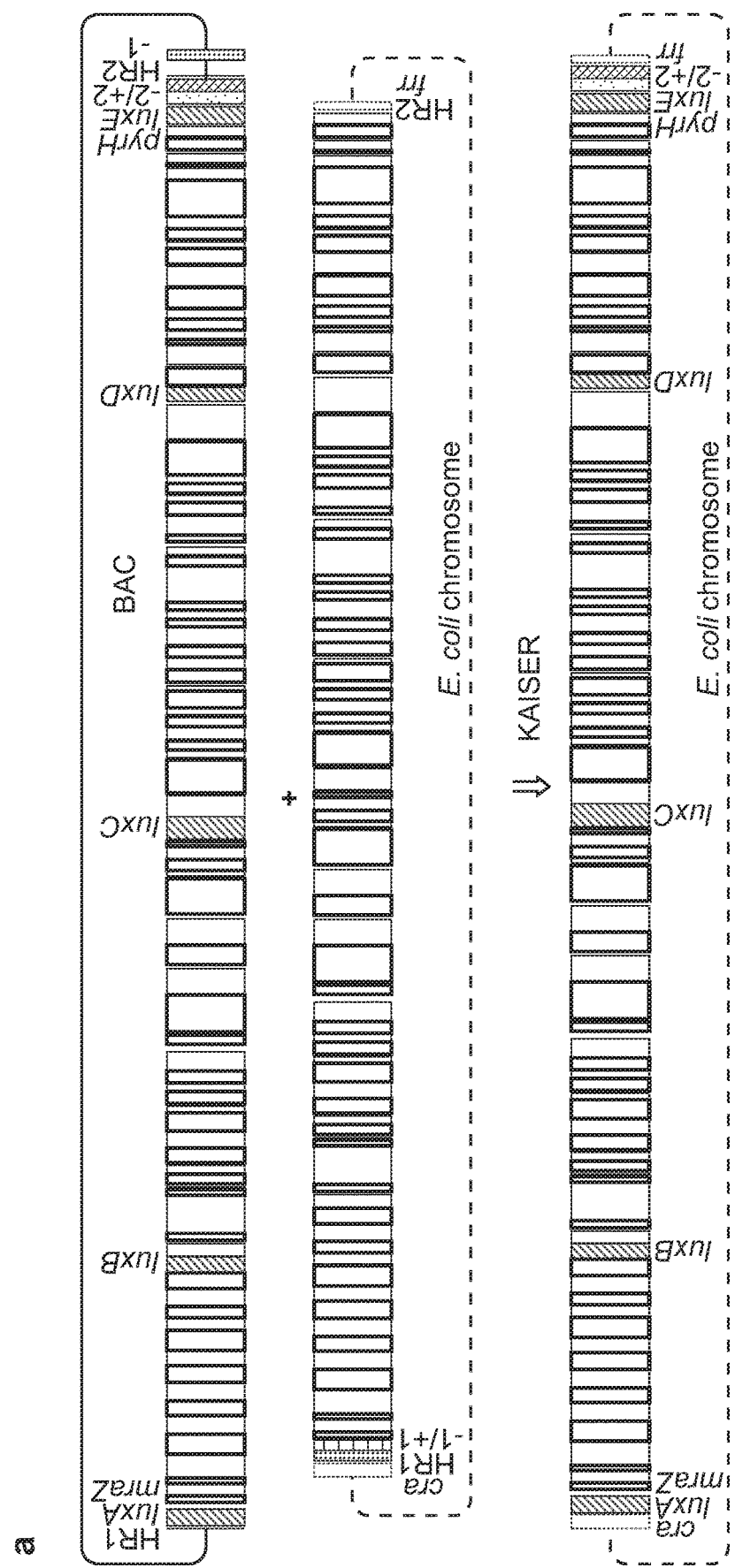
FIG. 3 shows Efficient replacement of 100 kb of genomic DNA with synthetic DNA via KAISER 2. a. Replacing 100 kb genomic DNA with 100 kb of DNA watermarked with lux genes via KAISER. The open reading frames (ORF) of genes in this region are represented by boxes with two alternating shades of grey, and the length of each box is scaled to the length of its ORF. The five genes of the lux operon (pink) are spaced out through the 100 kb in the BAC as watermarks for genomic replacement with synthetic DNA. Complete replacement leads to stable transfer of all five lux genes (luxA, R, C, D, E) into the genome, resulting in bioluminescent cells. A partial replacement would result in the loss of one or multiple lux genes resulting in non-bioluminescent cells. b. Efficient replacement of entire 100 kb genomic DNA using KAISER 2. Both KAISER 2 and KAISER 4 yield bioluminescent cells as demonstrated by superimposing white light pictures with luminescent pictures of the double selection plates. Bioluminescent colonies from KAISER 2 and KAISER 4 are resistant to chloramphenicol and sensitive to kanamycin and genotyping confirms replacement of genomic DNA with sequences containing each watermark.
Figure 6:
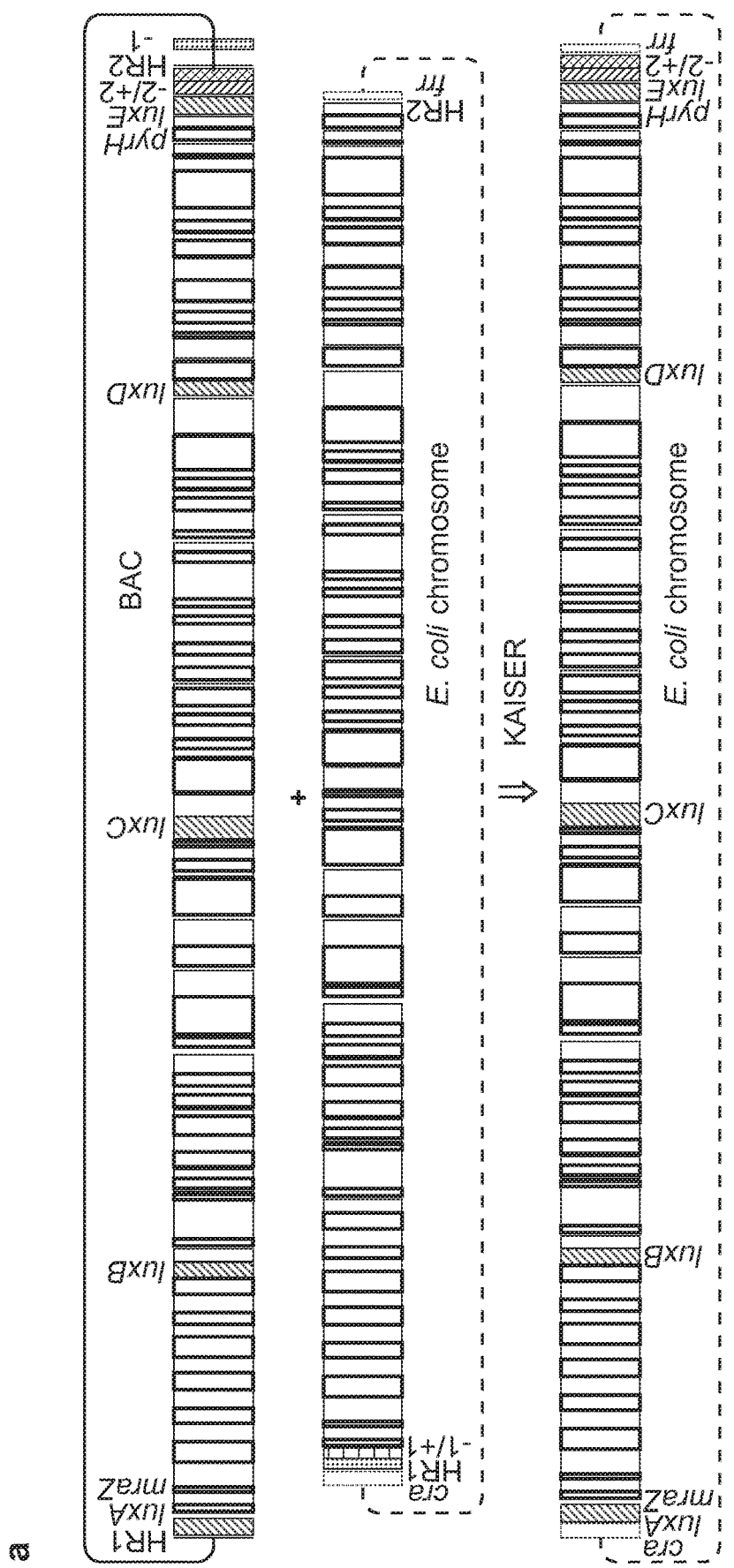
FIG. 6 (Extended Data FIG. 2) shows Replacement of 100 kb of genomic DNA with synthetic DNA with lux gene watermarks via KAISER. a. Replacing 100 kh genomic DNA with 100 kb of DNA watermarked with lux genes via KAISER. The open reading frames (ORF) of genes in this region are represented by boxes with two alternating shades of grey with the length of each box scaling to the length of each ORF. The five genes of the lux operon (pink) are spaced out through the 100 kb in the BAC as watermarks for genomic replacement with synthetic DNA. Complete replacement leads to stable transfer of all five lux genes (luxA, B, C, D, E) into the genome resulting in bioluminescent cells. A partial replacement would mean the loss of one or multiple lux genes resulting in non-bioluminescent cells. b. Complete or partial replacement of 100 kb genomic DNA with lux gene watermarks. All colonies from KAISER, whether bioluminescent or not, are resistant to chloramphenicol and sensitive to kanamycin. All bioluminescent colonies are confirmed to contain all five lux watermarks indicating replacement of the 100 kb genomic DNA with watermarked synthetic sequence. All non-bioluminescent colonies have the first (luxA) and the last (luxE) watermarks but are missing at least one of the watermarks in the middle (luxB, C, D). None of the non-bioluminescent colonies contain the second watermark (luxB), indicating potential detrimental sequences around this region in the synthetic DNA.
Figure 6:
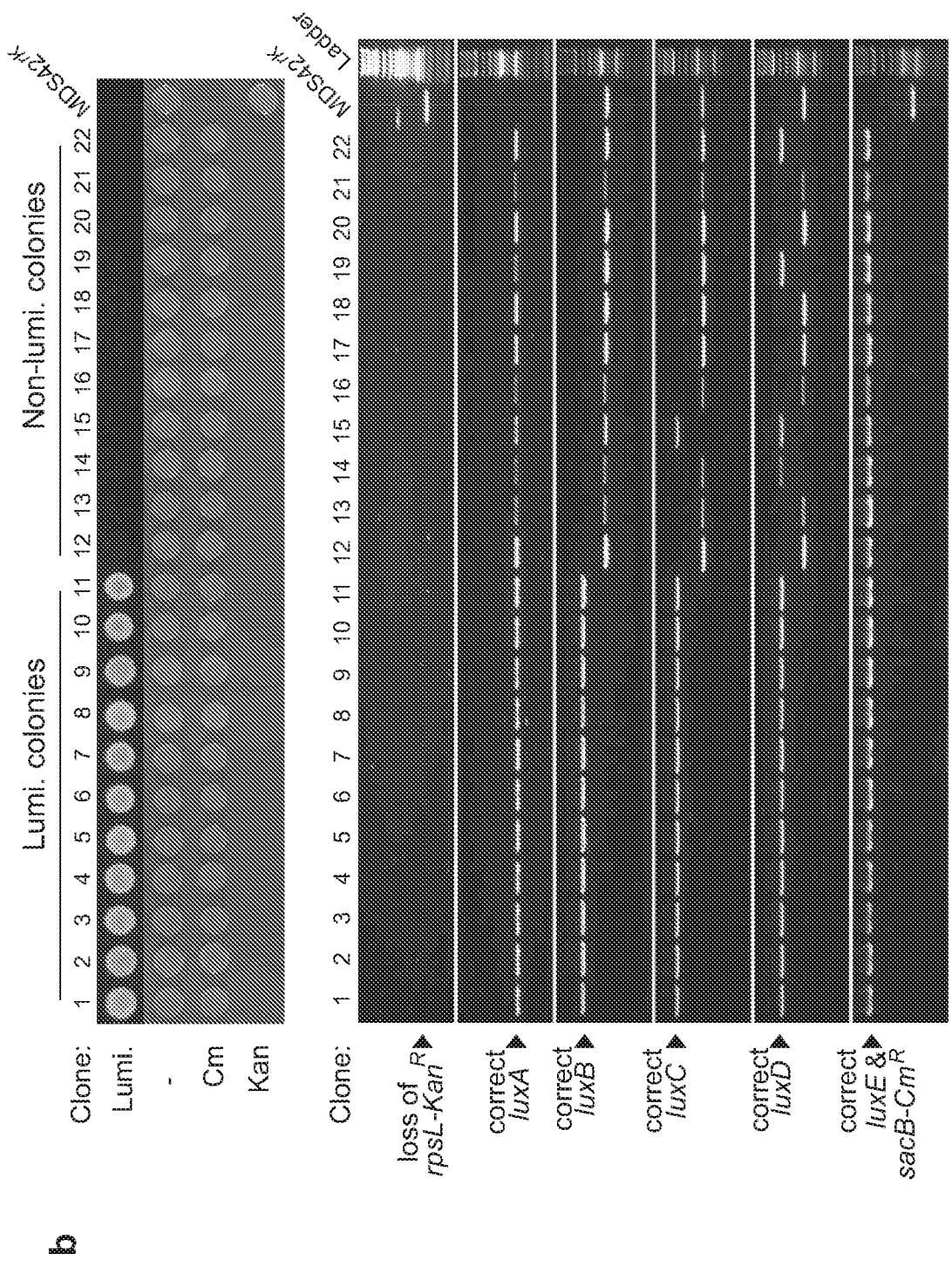

We designed an insert for the BAC, for insertion between HR1 and −2/+2 on the BAC, in which the 100 kb region between mraZ and pyrH is watermarked by the insertion of individual genes from the lux operon (luxA, luxB, luxC, luxD and luxE) along its length (FIG. 3a). The desired BAC was assembled by fragment assembly in *S. cerevisiae*[18]. KAISER 2 yielded $4×10^3$ c.f.u. per reaction, of which 55% were bioluminescent, while KAISER 4 yielded $2×10^3$ c.f.u. per reaction, of which 10% were bioluminescent (FIG. 3b). Further characterization confirmed the integration of the synthetic operon at the desired locus for all bioluminescent colonies, while non-bioluminescent colonies contained chimeras of the parent sequence and the lux watermarks (FIG. 3b, FIG. 6 (Extended Data FIG. 2)). These results demonstrate that KAISER enables the replacement of genomic regions with long synthetic DNA. Moreover, they reveal that replacements containing the lux genes, which may not be phenotypically silent, can be recombined out in a fraction of clones. By mapping regions in synthetic DNA that are consistently not transferred to the genome, in this case luxB (FIG. 6 Extended Data FIG. 2)), detrimental sequences in designed synthetic DNA may be defined.

Example 6: Recoding

The synonymous recoding of particular codons and removal of their cognate tRNA from the genome may enable the reassignment of these codons to new orthogonal aminoacyl-tRNA synthetase pairs that direct the incorporation of new chemical building blocks in response to sense codons, and facilitate genetic code reprogramming for the in vivo synthesis of unnatural polymers[9]. Arbitrary synonymous recoding may change translation speed[19,20], mRNA folding[7], and transcriptional[21] or translational[22] control elements, leading to alterations in co-translational folding[23,24] and protein expression level[7]. Combinatorial recoding of a given codon with all possible synonyms at all positions in the genome is impossible. For example, combinatorial exploration of the synonyms of the rarest sense codon in *E. coli* (AGG) at all (1491) positions in the genome would require exploration of $10^{1042}$ genomes; exceeding the number of atoms estimated in the observed universe ($10^{80}$). Such considerations highlight the importance of discovering general recoding rules, which define synonymous recodings that are allowed at many positions in the genome.

Numerous experiments have investigated the recoding of individual genes with libraries of synonymous mutations[7,25]. However, there are no experiments investigating the consequences of simultaneously recoding numerous essential genes in an essential genomic region with well-defined synonymous recoding rules, as required for well defined genome recoding. We used KAISER 2 to address this challenge and investigate synonymous recoding rules that would create codons that could be assigned to unnatural monomers, following deletion of the relevant tRNA genes, if applied genome-wide.

We focused on removing serine codons, as they are one of three codon sets (Ala, Leu, Ser), for which the aminoacyl-tRNA synthetase does not recognize the anticodon sequence of its cognate tRNAs and where introduction of an orthogonal tRNA that co-opts a serine anticodon will not lead to mis-aminoacylation by seryl-tRNA synthetase[26]. We identified target serine codons that i) when removed from the genome enable the removal of all their decoding tRNAs, and where ii) removal of these tRNAs would not remove all decoding of the remaining synonymous codons in the genome; these are the minimum criteria for removing a sense codon from the genome to enable its unambiguous reassignment.

We then defined the best synonymous replacements for the target serine codons by identifying the closest match for the target codons, as judged by either codon adaptation index (cAi)[27], tRNA adaptation index (tAi)[28,29], or a third metric that we propose, combining codon abundance and measured tRNA concentrations (translation efficiency, t.E) (Extended Data Table, Methods). These considerations led to three recoding schemes (FIG. 4a) in which i) TCG and TCA codons are both replaced with AGT codons (cAi, recoding scheme 1), ii) TCG and TCA codons are both replaced with AGC codons (tAi, recoding scheme 21, and iii) TCG codons are replaced with AGC codons and TCA codons are replaced with AGT codons (t.E, recoding scheme 3).

Figure 7:
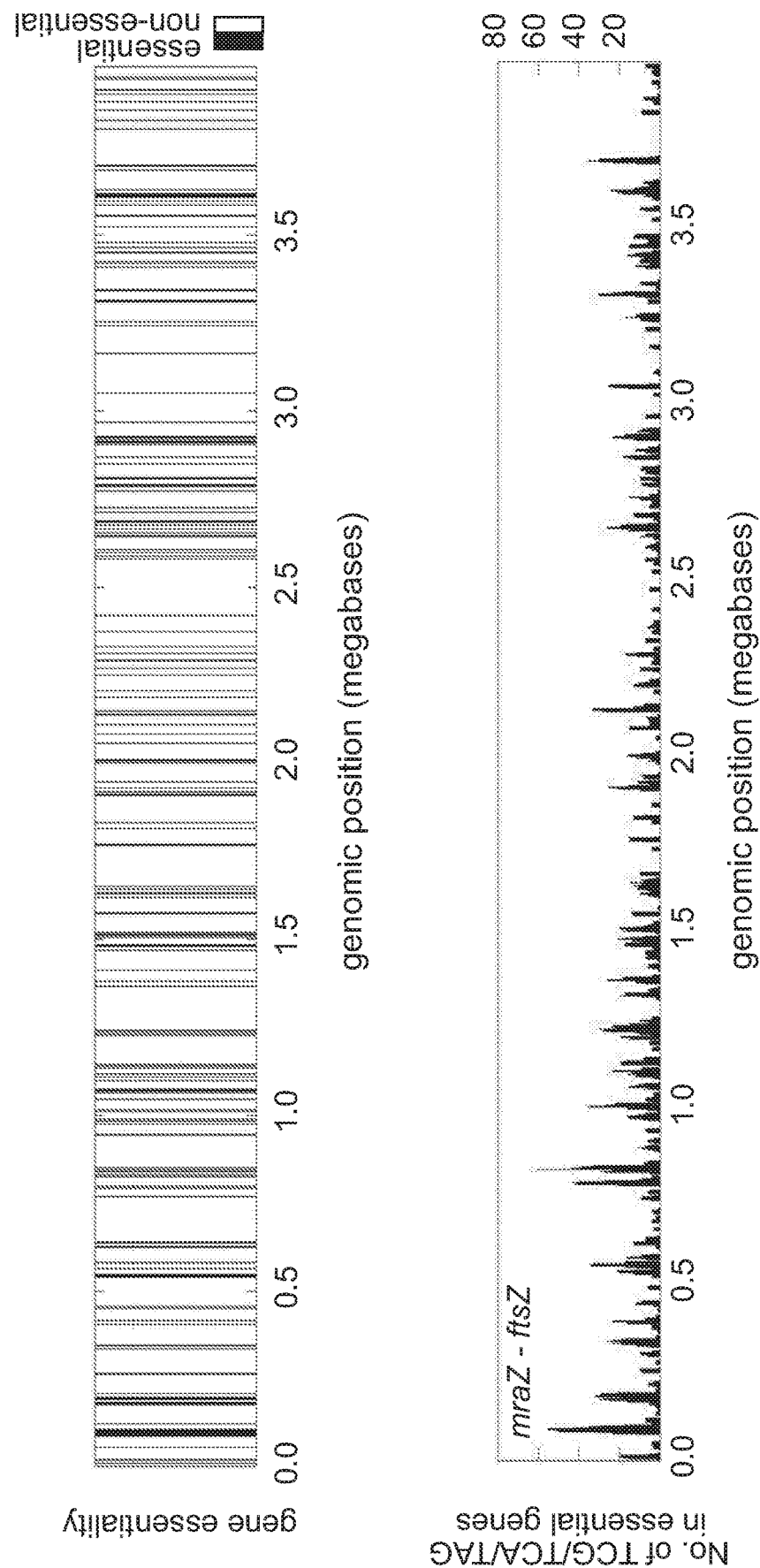
FIG. 7 (Extended Data FIG. 3) shows Choice of 20 kb recoding region and design of recoded synthetic sequence. a. Choice of 20 kb recoding region. To identify the best candidate region to test our synonymous recoding schemes, we focused on regions that contain a large number of essential genes as well as large numbers of the codons targeted for recoding, specifically $TCA^{Ser}$ and $TCG^{Ser}$ and TAG amber. We first identified essential genes based on their absence in the KEIO collection, which identifies individually non-essential genes in E. coli. The positions of essential genes were mapped on to the MDS42 genome. We then applied a sliding window approach, where we counted the number of target codons within all essential genes within a 10 kb region of the MDS42 genome. Starting from the first 10 kb of the genome sequence, we iteratively shifted the window by 100 nt and performed the codon analysis until the end of the MDS42 genome sequence. We identified the mraZ to ftsZ region, which corresponds to the cell division operon, as the highest scoring 20 kh region across MDS42 genome in our sliding window approach. b. Design of recoded synthetic sequence with new architecture and new decoding rules. The mraZ to ftsZ region contains fifteen genes, five of which overlap in distinct reading frames. To allow independent recoding of each gene while leaving potential cis-regulatory regions within the overlap intact, we designed a new architecture in which 200 nt upstream of the start codon of each overlapping ORF is duplicated (indicated as duplicated regions, d.r.). We designed a DNA sequence in which recoding scheme 1 is implemented within all of the fifteen genes in this new architecture, as well as sequences in which recoding schemes 2 or 3 are implemented within the new architecture. The DNA for each scheme was synthesized de novo, and assembled into a BAC in S. cerevisiae to test genomic recoding with each scheme via KAISER 2.
Figure 7:
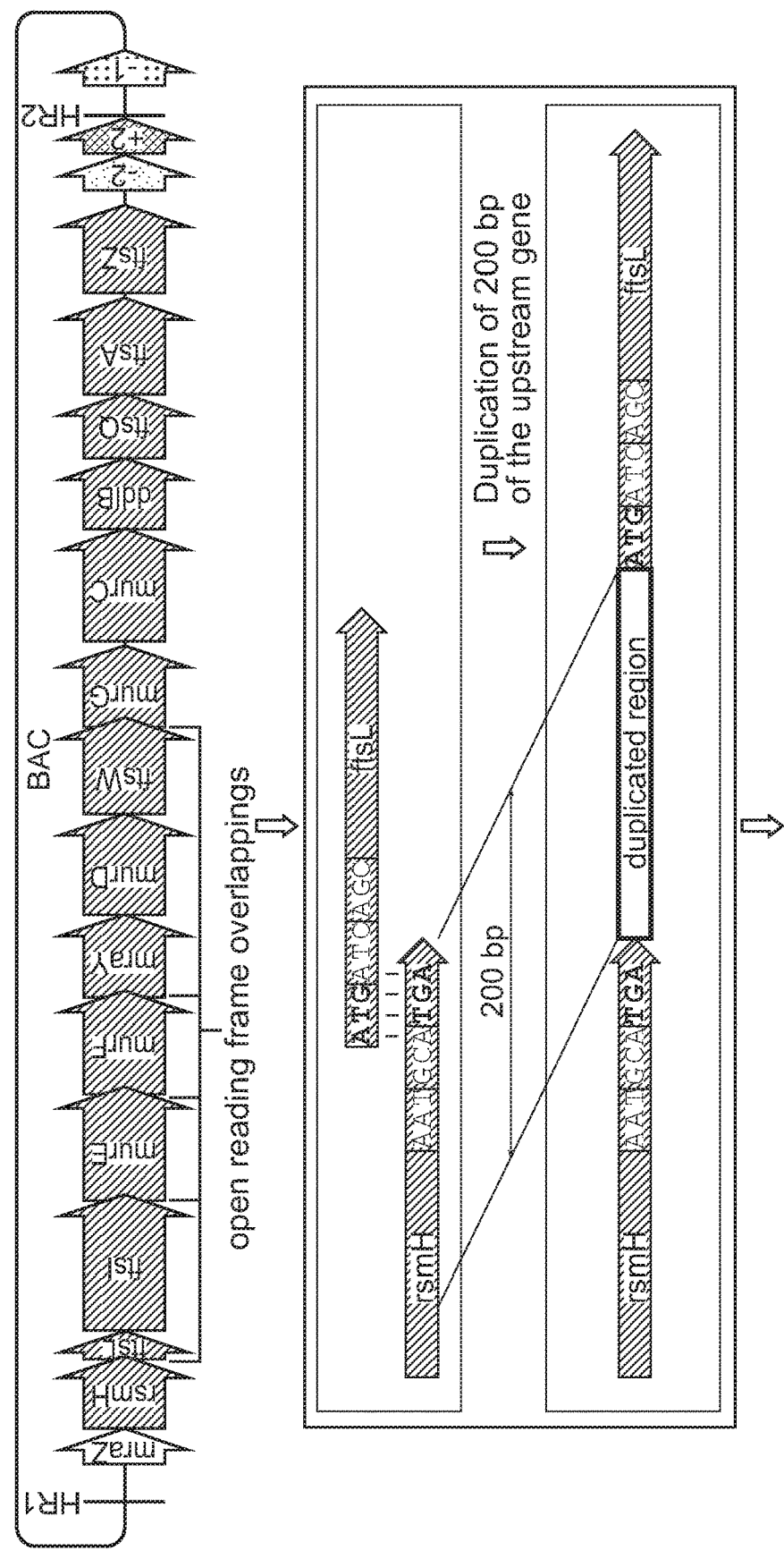

We identified the *E. coli* cell division operon (from 89,062 to 106,507) as an ideal target to test these synonymous recoding schemes because it i) is rich in essential genes (12 out of 15 genes in the region are essential)[30], ii) contains proteins expressed at a range of levels[31-36], iii) includes membrane proteins[37-34], iv) includes several proteins for which the ratios of expression are distinct and crucial[33,34], and v) is rich in the target codons (FIG. 7 (Extended Data FIG. 3a)). We anticipated that these features would ensure that deleterious synonymous recodings had clear effects, and that the genes reflect the range of expression levels and protein localizations in the proteome, more accurately than highly expressed genes, such as ribosomal genes[25].

The 20 kb region (from 89,062 to 106,507) of interest contains fifteen genes, five of which overlap in distinct reading frames. To allow independent recoding of each gene, while leaving potential cis-regulatory regions within the overlap intact, we designed a new architecture in which 200 nucleotides upstream of the start codon of each overlapping ORF are duplicated (FIG. 4b). We designed a DNA sequence in which recoding scheme 1 is implemented within all of the fifteen genes in this new architecture, as well as sequences in which recoding scheme 2 or 3 are implemented within the new architecture. Overall the three schemes introduce 741 nucleotide changes, 247 nucleotide changes for each scheme (FIG. 4c). The DNA for each scheme was synthesized de novo, and assembled into a BAC in S. cerevisiae to test genomic recoding with each scheme via KAISER 2 (FIG. 4b).

Figure 4:
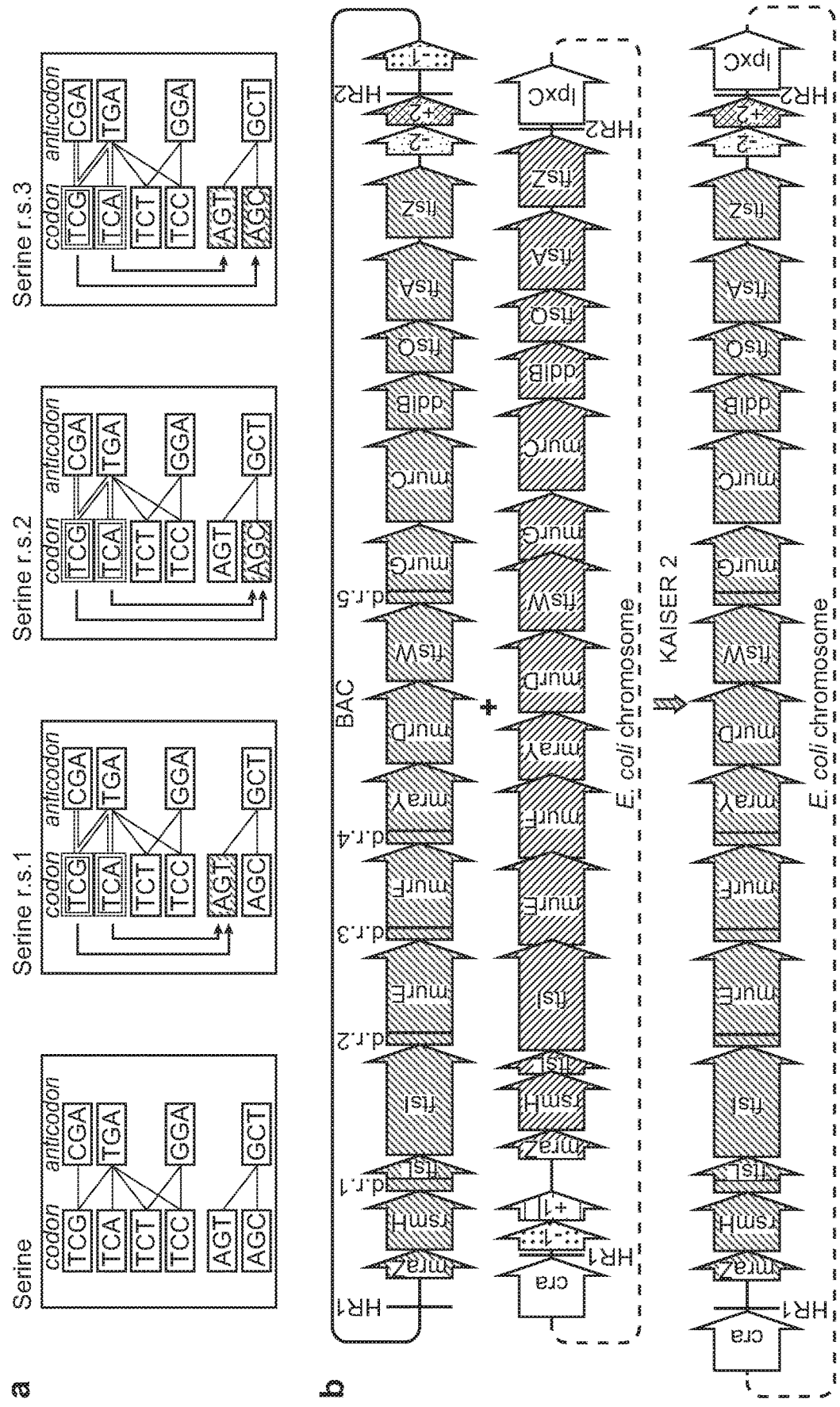
FIG. 4 shows Testing systematic synonymous codon reassignment on a 20 kb region of the *E. coli* genome rich in essential genes. a. The codon-anticodon interactions for *E. coli* serine tRNAs. and three recoding schemes (r.s). Lines indicate codon anticodon interactions. Grey lines indicate decoding events removed in the target region by synonymous recoding. Codons targeted for removal are shown in grey, and their replacements are shown in pink. Arrows link the codons targeted for removal with their replacements. Application of one of these recoding schemes genome-wide would allow the TCG codon to be reassigned to a new amino acid using a tRNA with a CGA anticodon. b. The region from 89.062 to 106.507 was engineered by duplicating the five overlapping reading frame sequences, creating duplicated region (d.r.) 1-5. The genes were then recoded according to synonymous recoding scheme (r.s.) 1, 2 or 3 to create three BACs. +2 is $Cm^R$, -2 is sacB, +1 is $Kan^R$, -1 is rpsL, which were used for KAISER 2. c. The sequence between HR1 and HR2 is indicated by the pink bar, and the position of every codon targeted for replacement is shown by a red line. For each recoding scheme ten clones were sequenced. Grey bars indicate wt genomic sequence, and pink bars indicated genomic sequence that has been recoded with the indicated scheme.
Figure 4:
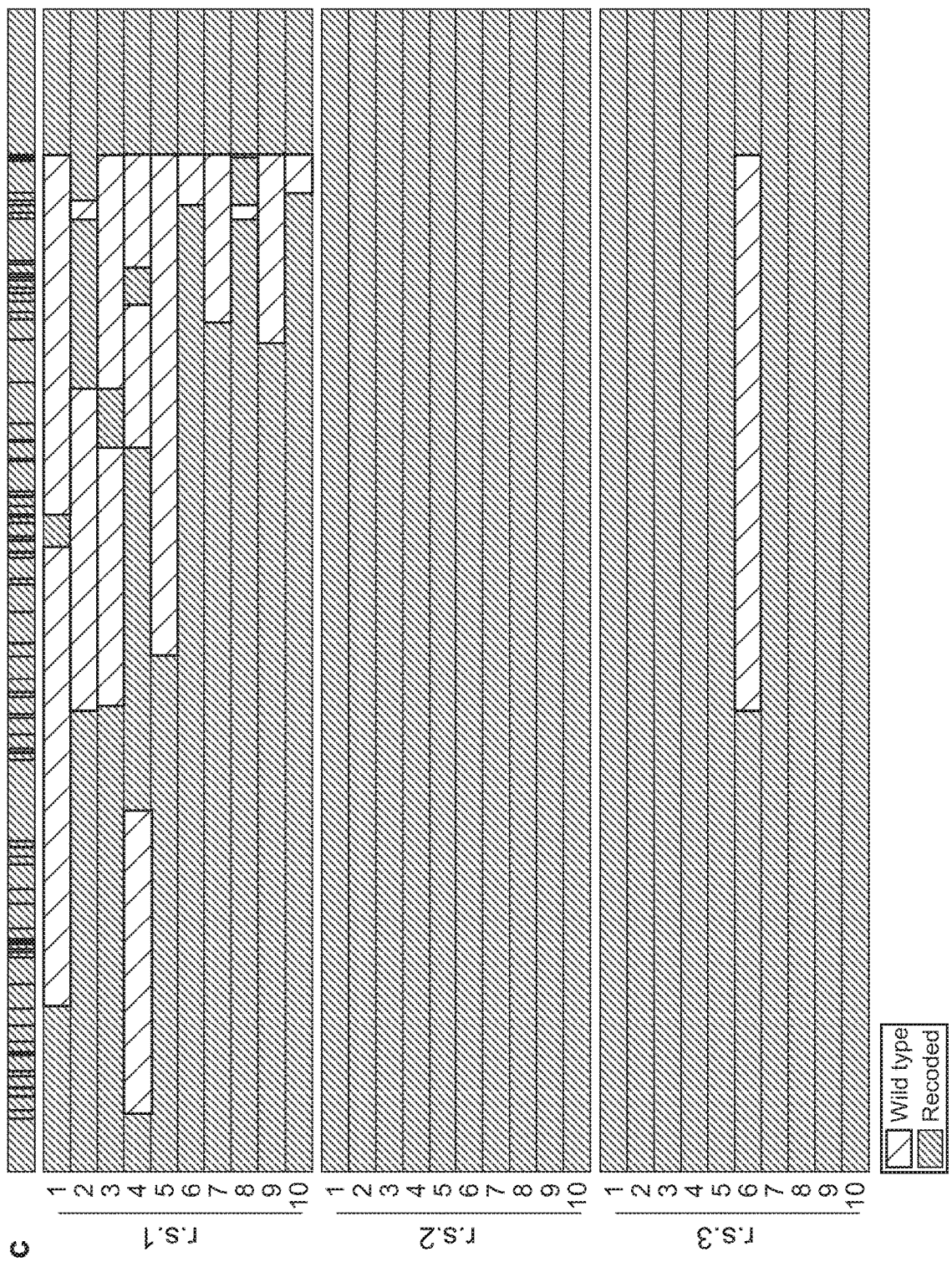
Figure 8:
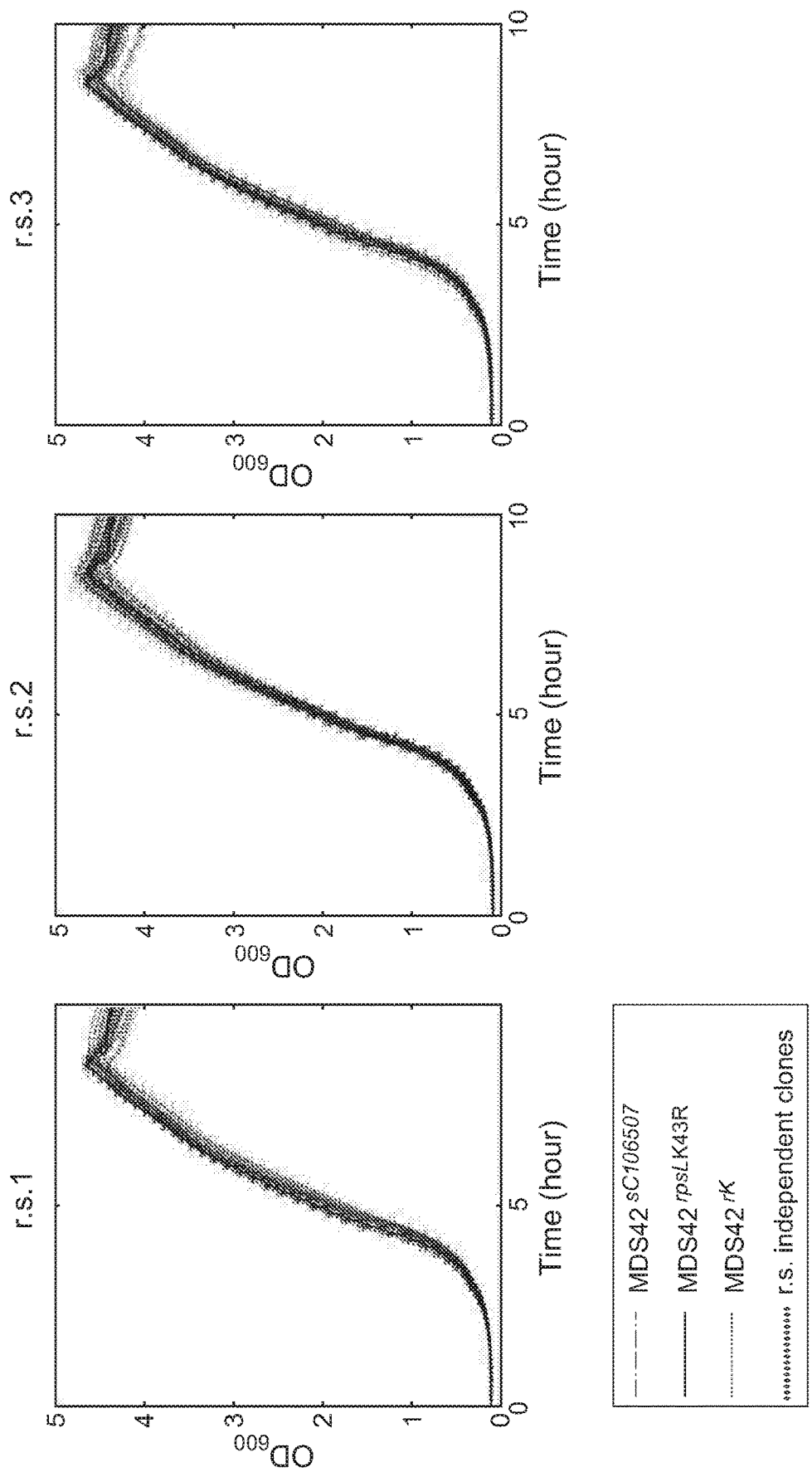
FIG. 8 (Extended Data FIG. 4) shows Culture growth of synonymously recoded clones. The growth of individual clones resulting from each 20 kb recoding by KAISER was monitored. For each clone, $OD_{600}$ was measured in triplicate, in intervals of 10 min, until culture saturation. As controls, the $MDS42^{rpsLK43R}$, $MDS42^{iK}$, and $MDS42^{sC106507}$ (with sacB-$Cm^R$ inserted between 106.507 and 106,508 to mimic the positions of sacB-$Cm^R$ in the recoded clones) were grown alongside the recoded clones. The calculation and comparison of maximal exponential growth rates did not indicate a significant difference between control $MDS42^{sC106507}$ and any of the tested recoding clones (two-sample t-test, p-value >0.01). Errorbars: mean±standard deviation.

We sequenced ten independent clones from each scheme following recoding by KAISER 2 (FIG. 4c). For scheme 1 we observed chimeras between the wild-type genomic DNA and the recoded DNA, consistent with recombination-mediated crossover. In contrast, for scheme 2 we observed complete conversion of the genomic sequence to the recoded sequence and for scheme 3 nine out of ten clones were completely recoded. The doubling times for all clones were comparable to each other and to E. coli MDS42 (FIG. 8 (Extended Data FIG. 4)), indicating that growth rates were unaffected by genome recoding. Our data demonstrate that scheme 2 recoding is allowed, while scheme 1 recoding is not, even though the codons used for replacement in scheme 1 and scheme 2 recoding differ by only a single base (AGT vs AGC), and are decoded by the same tRNA (with anticodon GCT) via wobble and Watson Crick decoding respectively (FIG. 4a).

Moreover, because the approach provides chimeric sequences when recoding of every codon within the targeted region is not permitted, it may provide information on the precise genomic location of problematic nucleotide changes. Indeed, aligning ten chimeras from scheme 1 reveals a single position at which the wild type sequence is maintained, codon 407 in ftsA. The wild type codon at this position is TCG, and this is converted to AGT in scheme 1 and AGC in scheme 2 and 3. This analysis identifies a single base change (T to C) at the third position of codon 407 in ftsA as the common feature of failed recodings.

Figure 18:
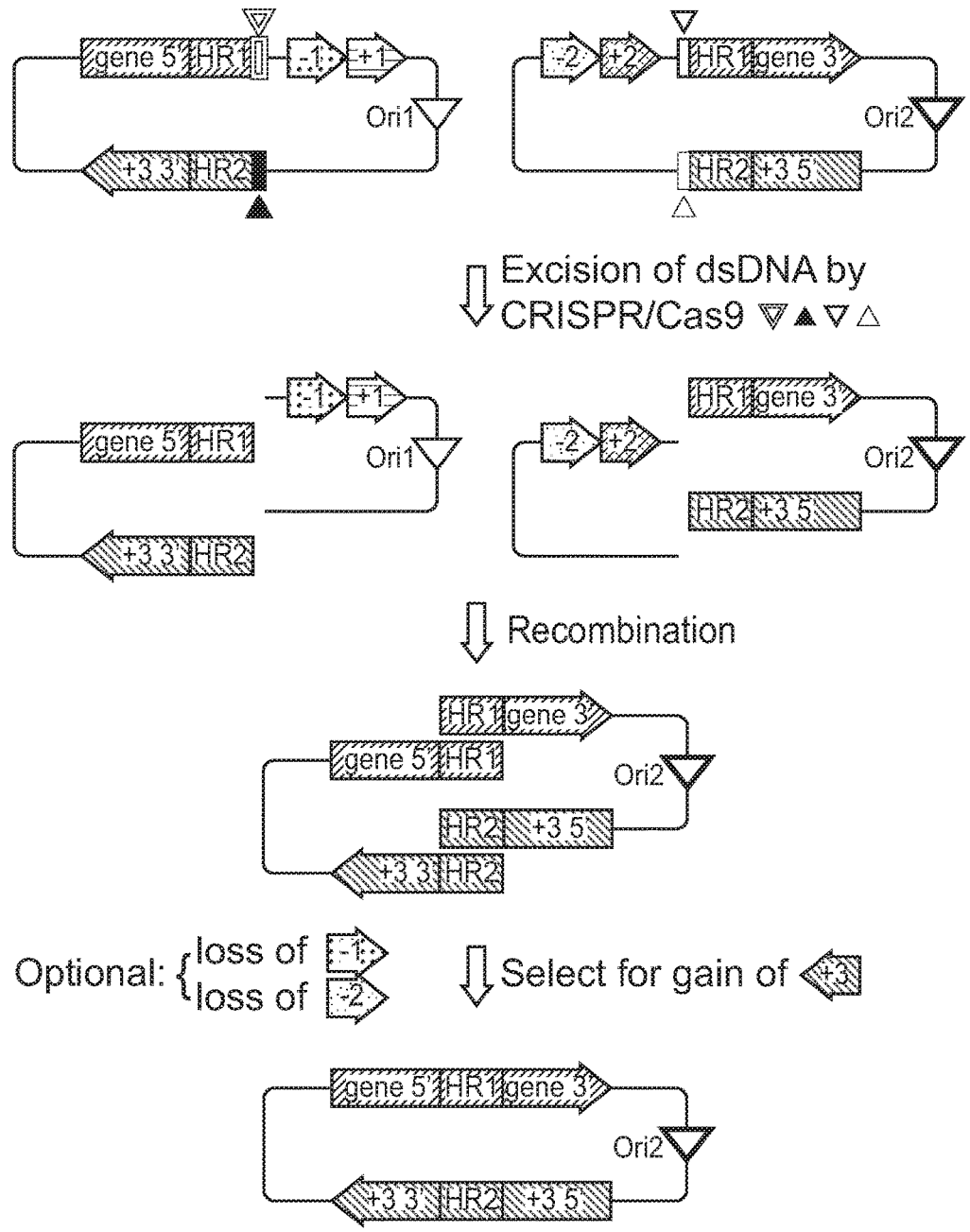
FIG. 18 shows a diagram of a recombination and selection scheme.

In addition, it should be noted that the invention can be applied to making of libraries. Reference is made to FIG. 18, showing a scheme according to the invention. Regarding the manufacture of plasmids and/or libraries according to the invention, we refer to FIG. 18, which shows making a library with $10^{10}$ diversity by combining 2 half-libraries of $10^5$ diversity by 'KAISER 4p'.

Summary of Examples 1 to 6

In conclusion, we have demonstrated approaches that generate donor nucleic acids such as linear synthetic dsDNA in vivo via in vivo excision from an episomal replicon, to enable insertion of 90 kb of synthetic DNA into the E. coli genome or replacement of 100 kb of the E. coli genome with synthetic DNA in a single step. The approach can be iterated, and enables replacement of the entire E. coli genome with synthetic DNA in no more than 40 steps (FIG. 5 (Extended Data FIG. 1d)), with each step taking a few days. The invention (e.g. KAISER) has enabled defined decoding rules to be tested simultaneously on numerous essential genes in the genome for the first time. These experiments reveal that well-defined synonymous replacements can be discovered that may allow complete and concerted synonymous recoding of the genome.

Example 7: Efficient Single Step Replacement

Overview

Previous work has investigated the role of synonymous codon choice in individual genes expressed in E. coli. Initial experiments combinatorially recoded the GFP gene with synonymous codons and demonstrated that protein expression levels varied in recoded genes[7]. More recently individual genes within the E. coli ribosomal operon were targeted for recoding by classical recombination[25]. These experiments aimed to replace sense codons in one gene at a time with a randomly weighted distribution of synonymous codons (FIG. 5 (Extended Data FIG. 1)). Certain codons were targeted for exclusion from the recoded gene, but exclusion of these codons would not be sufficient to enable codon reassignment (FIG. 5 (Extended Data FIG. 1)). 12 ribosomal genes could not be individually recoded to remove all occurrences of the targeted codons. Moreover, the strains that could be recoded had substantial growth defects.

Because previous approaches replace codons with randomly chosen synonyms, they do not systematically test the effect of replacing a particular target codon with a particular synonymous substitution at many positions within the gene, as would be required to define precise rules for allowed and disallowed synonymous substitutions in a gene. Moreover, because previous work recoded individual genes[7,25], it does not capture the consequences of epistatic interactions amongst codons in distinct genes in an operon. Epistasis amongst codons in distinct genes within an operon will be important because, for example, proteins within an operon, the levels of which are defined by codon choice, ma, interact at precisely defined ratios to effect biological function.

Here we endow E. coli with machinery that enables the efficient insertion of very long synthetic DNA, and the replacement of genomic DNA with very long synthetic DNA. In our approach, named REXER (replicon excision for enhanced genome engineering through recombination), the programmed in vivo excision of double stranded DNA from an episomal replicon by CRISPR/Cas9 is triggered to enable lambda red mediated recombination at a precisely targeted locus. We insert 90 kb of synthetic DNA into the E. coli genome in a single step, replace 100 kb of the E. coli genome with synthetic DNA in a single step, and demonstrate that the method may be iterated for the stepwise replacement of longer genomic regions. The ability to replace long stretches of genomic DNA with synthetic DNA enables us to recode an operon in the E. coli genome that contains fifteen genes, including twelve essential genes involved in cell division. We simultaneously recode all the genes in this operon using eight different well-defined synonymous recoding rules. Each recoding rule removes every occurrence of each target codon tested and replaces it with a defined synonym that, following genome wide application and cognate tRNA deletion, would enable unambiguous codon reassignment. Using this approach we simultaneously remove all occurrences of target codons in the region of interest, leading to the removal of target codons at upto 374 positions. We define synonymous substitutions that are deleterious at many positions and lead to poorly tolerated recoding schemes, and we define other synonymous substitutions for the same target codons that are allowed at all positions. Our results reveal dramatic differences in the extent to which different synonymous replacements for the same target codons are allowed in a group of genes encoding interacting proteins. Our approach enables the identification of idiosyncratic positions where a precise codon substitution that is allowed at all other positions in the operon is disallowed. Moreover, we demonstrate that alternative recoding of idiosyncratic positions can rescue a recoding scheme.

Example 7A—100 kb Replacement

Next, we demonstrated that REXER 2 and REXER 4 allow us to efficiently replace 100 kb of the E. coli genome in a single step (FIG. 3a). The desired BAC was assembled by fragment assembly in S. cerevisiae[18]. REXER 2 yielded $2 \times 10^4$ c.f.u. per reaction, of which 80% were bioluminescent, while REXER 4 yielded $5 \times 10^6$ c.f.u. per reaction, of which 50% were bioluminescent (FIG. 3b). Further characterization confirmed the integration of the lux gene watermarks at the desired loci for all bioluminescent colonies (FIG. 3b), while non-bioluminescent colonies contained chimeras of the parent sequence and the lux watermarks. These results demonstrate that REXER enables the replacement of genomic regions with long synthetic DNA. Moreover, they reveal that replacements containing the lux genes, which may not be phenotypically silent, can be recombined out in a fraction of clones. By mapping regions in synthetic DNA that are consistently not transferred to the genome, in this case luxB, detrimental sequences in designed synthetic DNA may be defined and potentially targeted for repair.

Example 7B—Iterative Application

Figure 5:
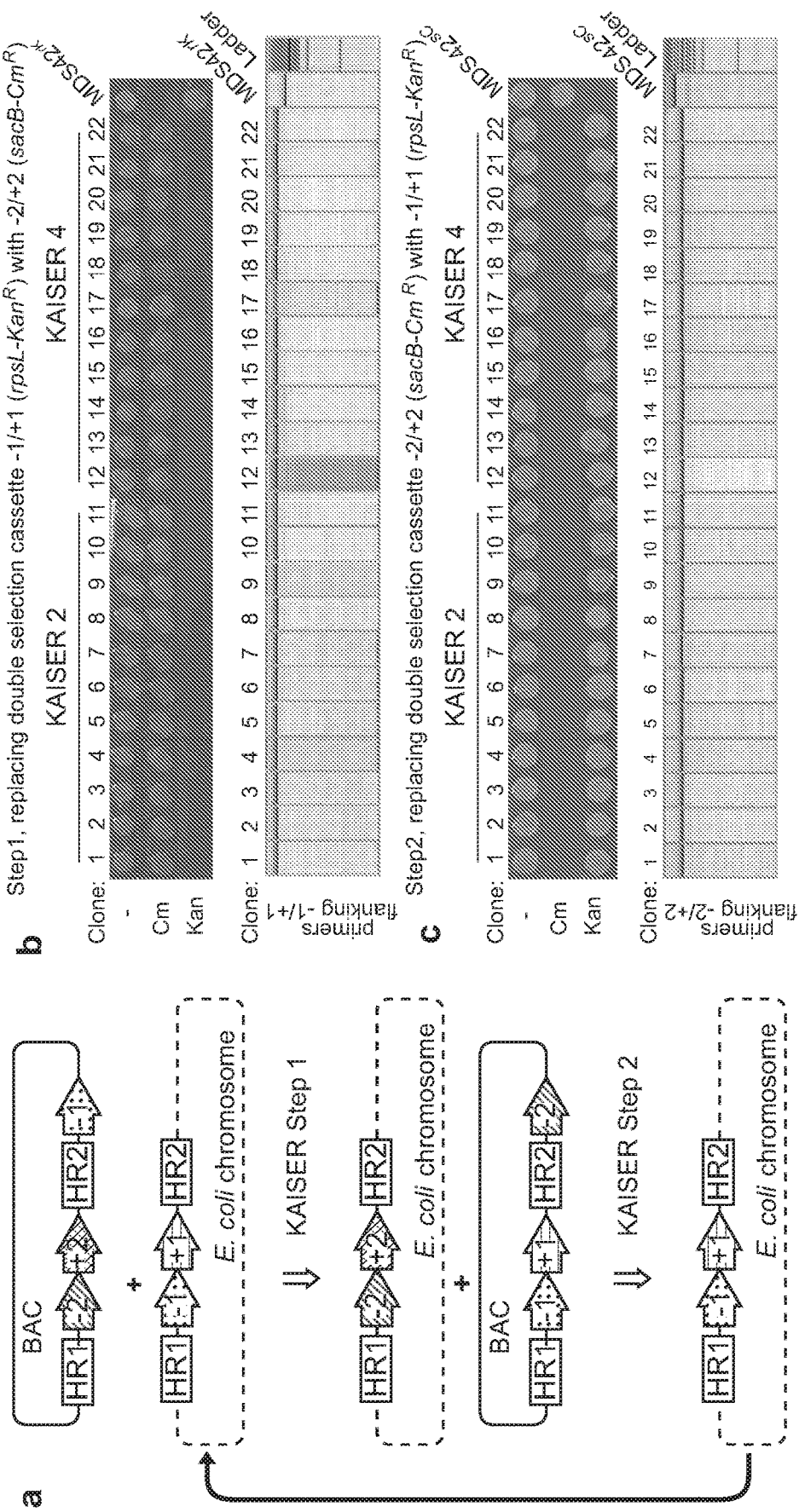
FIG. 5 (Extended Data FIG. 1) shows Iterative genomic changes by KAISER to enable Genome Stepwise Interchange synthesis (GENESIS). a. Iterative genomic changes by KAISER. Our alternating use of two distinct double selection cassettes −1/+1 (rpsL-$Kan^R$) and −2/+2 (sacB-$Cm^R$) with one cassette marked at defined locus on the genome and the other cassette on the BAC coupled with synthetic DNA allows the result of one round of KAISER to act as a template for the next round of KAISER. b. Efficient replacement of genomic rpsL-$Kan^R$ with BAC bound sacB-$Cm^R$ using KAISER$^2$ and KAISER$^4$. The sacB-$Cm^R$ is integrated into the genomic locus (between 89.061 and 89,587) marked with rpsL-$Kan^R$ using KAISER 2 and KAISER 4. 11 colonies each from KAISER 2 and KAISER 4 were shown to be correct by phenotype, colony PCR and DNA sequencing. c. Efficient iterative replacement of genomic sacB-$Cm^R$ with BAC bound rpsL-$Kan^R$ using KAISER 2 and KAISER 4. The rpsL-$Kan^R$ is integrated into the genomic locus (between 89.061 and 89.587) of clones from (b) using KAISER 2 and KAISER 4. 11 colonies each from KAISER 2 and KAISER 4 were shown to be correct by phenotype, colony PCR and DNA sequencing. The product of (c) can serve as template for (b) again. d. Genome Stepwise Interchange Synthesis (GENESIS). With the ability to perform 100 kb genomic replacement a step of wildtype fragment with synthesized fragment using KAISER and the ability to iterate consecutive KAISER steps using the product of the previous step as the template for the next step, we propose the Genome Stepwise Interchange synthesis (GENESIS) to replace the entire *E. coli* genome with synthetic DNA in around 40 steps.
Figure 5:
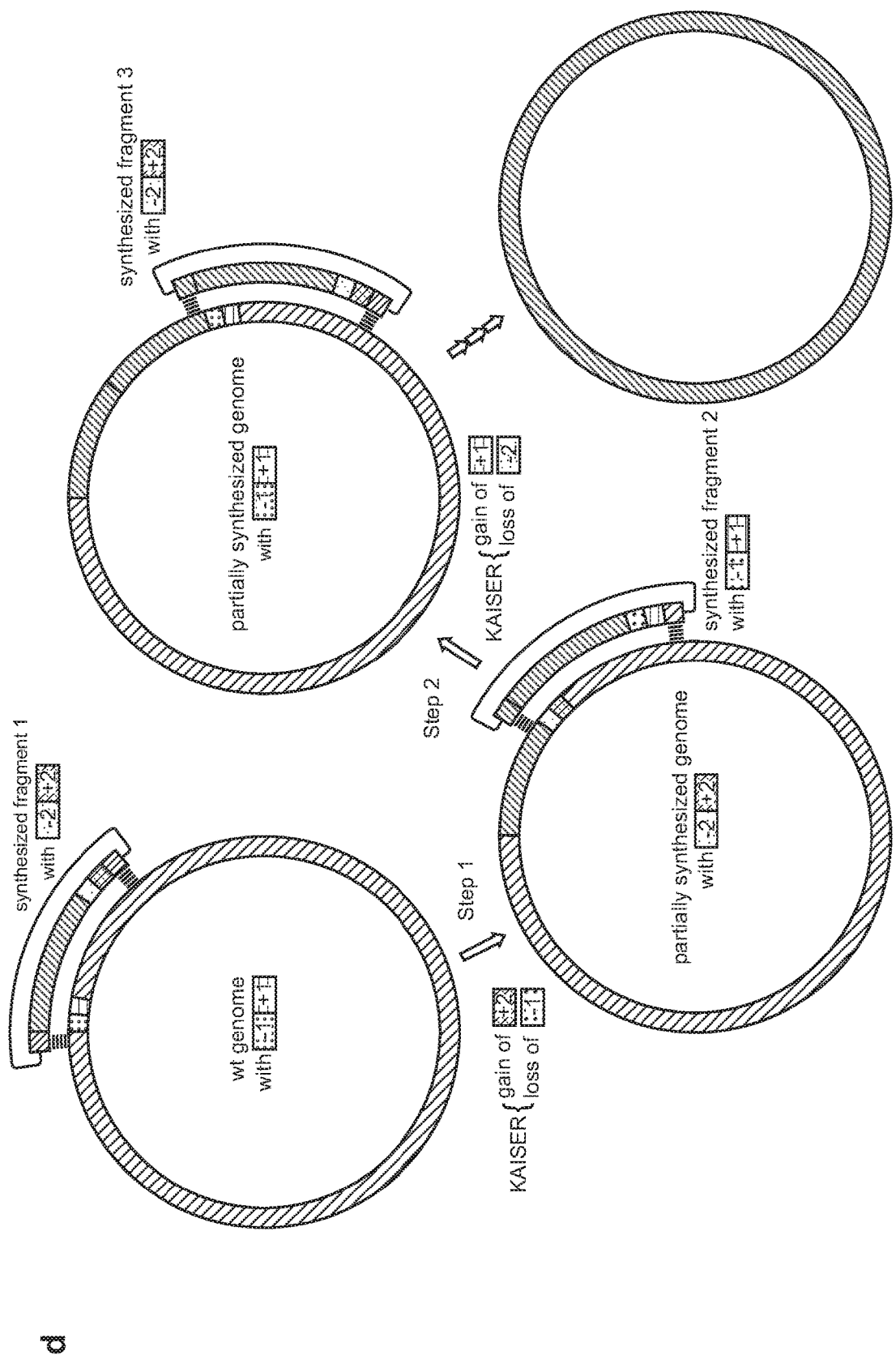

Next we showed that our approach for genome engineering can be iterated (FIG. 5 (Extended data FIG. 1a) and FIG. 9a (supplementary FIG. 2a)) to enable the stepwise replacement of even larger genomic regions. We first demonstrated that the genome created in a first round of REXER, that introduces the positive and negative selection markers +2 and −2, provides a direct template for a second round of REXER, using a BAC that contains distinct, but compatible, positive and negative selection markers (+1,−1) (FIG. 9b,c (supplementary FIG. 2b,c)). The product of the second round of REXER is a template for third round of REXER using the same combination of markers as used in the first round; thus the approach can be iterated (FIG. 9a (supplementary FIG. 2b,c)).

Example 7C: Replacement of Long Genomic Regions

To demonstrate that REXER can be iterated for the stepwise replacement of long regions of genomic DNA with synthetic DNA we used cells in which we had replaced the 100 kb genomic region between mraZ and pyrH by REXER (FIG. 3a,b & FIG. 9d (supplementary FIG. 2d)) for a second step of REXER. The second step introduces 124 kb of synthetic DNA spanning from frr to mhpT (192.744 to 376.670) and the hygromycin B phosphotransferase gene (hph), which confers resistance to hygromycin B. Following iterations of REXER, cells had the expected phenotype and genotype (FIG. 9e,f (supplementary FIG. 2e,f)), confirming successful replacement of 220 kb of the genome with 230 kb of synthetic DNA in two steps. This compares favourably with the largest replacement in the naturally recombinogenic S. cerevisiae (270 kb, 11 steps)[6]. Iteratively replacing large sections of the genome with synthetic DNA will enable the stepwise replacement of the whole genome with synthetic DNA (FIG. 14 (Extended Data FIG. 6)).

Example 7D: Recoding—Identification of Poorly Tolerated/Disallowed Mutations

Having established robust methods for replacing large sections of the E. coli genome, we used REXER to empirically define synonymous substitutions that are disallowed and poorly tolerated and synonymous substitutions that are allowed and can be implemented at many positions in the genome. To define a system for experimental investigation we i) identified the codons to target for removal, ii) defined recoding rules by identifying the codons with which the target codons might be replaced and iii) identified a region of the genome in which to test the recoding rules identified.

We chose target codons for removal that i) when removed from the genome would enable the removal of all the tRNAs that decode them, and where ii) removal of these tRNAs would not remove all decoding of the remaining synonymous codons in the genome; these are the minimum criteria for removing a sense codon from the genome to enable its unambiguous reassignment (FIG. 15 (Extended Data FIG. 7)). We focused on removing serine, leucine and alanine codons that fulfill these criteria, as these are the three codon sets for which the aminoacyl-tRNA synthetase does not recognize the anticodon sequence of their cognate tRNAs. This means that introduction of an orthogonal tRNA that co-opts an anticodon normally used to encode Ser, Leu or Ala will not lead to mis-aminoacylation of the orthogonal tRNA by an endogenous synthetase[26]. We defined candidate synonymous replacements for the target codons by identifying the closest match for the target codons, as judged by either codon adaptation index (cAi)[27], tRNA adaptation index (tAi)[28,29], or a third metric we define (translation efficiency, t.E), that combines cAi and intracellular tRNA level (Extended Data Table 4, Methods). These considerations led us to investigate eight recoding schemes (FIG. 10a (supplementary FIG. 3a)).

We identified the E. coli cell division operon (from 89,062 to 106.507) as an ideal target to test these synonymous recoding schemes because it i) is rich in essential genes (12 out of 15 genes in the region are essential)[30], ii) contains proteins expressed at a range of levels[31-36], iii) includes membrane proteins[37-43] (a class of proteins for which co-translational folding and function is known to be affected by synonymous codon choice), iv) includes several proteins that interact and for which the ratios of proteins expressed are distinct and crucial[33,34] (which will favour epistatic interactions amongst codons in different genes), and v) is rich in the target codons (FIG. 10b (supplementary FIG. 3b), Extended Data Table 5). We anticipated that these features would ensure that the genes reflect the range of expression levels and protein localizations in the proteome, more accurately than other regions, such as ribosomal operons[25], that contain very few of the target codons, primarily contain highly expressed genes (Extended Data Table 5) and are heavily biased towards a subset of codons. Moreover we anticipated that these features would ensure that deleterious synonymous recoding within the operon had clear effects.

We designed DNA sequences in which each of the recoding schemes is implemented within all of the fifteen genes simultaneously. The schemes introduce up to 374 codon changes, and overall they investigate the consequences of 1,468 codon changes and 2,347 nucleotide changes (FIG. 10c (supplementary FIG. 3c)). The DNA for each scheme was synthesized de novo, assembled into a BAC in S. cerevisiae and genomic recoding via REXER investigated (FIG. 11a (supplementary FIG. 4a)).

Following REXER we sequenced 16 independent clones from each recoding scheme. We observed chimeras between the wild-type genomic DNA and the recoded DNA in several cases, consistent with recombination-mediated crossover between the recoded sequence and the wild-type genome, these chimeras defined a recoding landscape. We aligned the individual recoding landscapes to create a "compiled recoding landscape" (FIG. 11b (supplementary FIG. 4b)) that reveals peaks and plateaus for synonymous substitutions that are allowed and valleys or troughs for synonymous substitutions that are consistently disallowed. We observe clear differences in the extent to which replacement of the same codons by different synonymous codons are tolerated (FIG. 11b (supplementary FIG. 4b), FIG. 12 (supplementary FIG. 5), FIG. 16 (Extended Data FIG. 8)).

We first investigated the serine recoding schemes 1-3 (FIG. 12a (supplementary FIG. 5a)). For scheme 1 we observed chimeras between the wild-type genomic DNA and the recoded DNA, consistent with recombination-mediated crossover, and 0% of clones are completely recoded. In stark contrast, for scheme 2 and scheme 3 88% of clones were fully recoded. In contrast, we find that none of the leucine recoding schemes tested (schemes 4-6) led to complete recoding, and for scheme 4 and 5 recoding fails catastrophically, indicating that the synonymous substitutions have phenotypic consequences at man) sites in the operon (FIG. 12b (supplementary FIG. 5b)). Finally, we find that the two alanine recoding schemes tested (schemes 7-8) have dramatically different outcomes (FIG. 12c (supplementary FIG. 5c)). Recoding scheme 7 leads to 75% of clones being completely recoded at all 374 positions while no clones are fully recoded by scheme 8. The doubling times for all fully-recoded clones were comparable to each other and to a control *E. coli* strain (FIG. 13 (supplementary FIG. 6)), indicating that growth rates were unaffected by genome recoding. Overall, this work successfully removes up to 374 sense codons across 20 kb from the operon in a single strain. Thus the scale of sense codon removal is much greater than that previously reported for a release factor 2 gene (prfB), where 46 codons, spanning 1.1 kb, were removed in a single strain. The maximum number of codons simultaneously removed from a ribosomal gene (rpsA), in previous work, was 16[25].

Our data reveal the drastic differences between precisely defined recoding schemes in an operon of interacting essential genes. This information cannot be obtained when the choice of synonymous substitution is randomized in single genes. For serine recoding, scheme 2 and 3 recoding is allowed, while scheme 1 recoding is not; even though the codons used for replacement in scheme 1 and scheme 2 and 3 recoding differ by only a single base (AGT vs AGC), and are decoded by the same tRNA (with anticodon GCT) via wobble and Watson Crick decoding, respectively (FIG. 10a (supplementary FIG. 3a)). Similarly for alanine codons, scheme 7 recoding is allowed while scheme 8 fails catastrophically. These recoding schemes differ only in the conversion of a single base (GCT vs GCC) in the allowed and disallowed substitution for GCA. Again, both of the new codons are decoded by the same set of tRNAs (FIG. 10a (supplementary FIG. 3a)). cAI, tAi and tE all produce at least one successful recoding, but no single metric predicts which synonymous recoding will be successful. These observations underscore the importance of empirically determining the best systematic and well-defined synonymous recoding scheme for each codon within an operon rich in essential genes.

Aligning the chimeric genomic sequences resulting from performing REXER with recoding scheme 1 reveals that, *E. coli* consistently rejects a single codon mutation (TCG to AGT) at codon 407 of ftsA (FIG. 12a (supplementary figure 5a)). Attempts to introduce the ftsA 407 TCG to AGT mutation (without additional recoding at other positions in the genome) failed (FIG. 13a (supplementary FIG. 6a)). In contrast, we were able to quantitatively recode ftsA 407 TCG to the synonymous TCT codon (FIG. 13a (supplementary FIG. 6a)). These results demonstrate that the ftsA 407 TCG to AGT mutation is deleterious.

Example 7E: Testing Alternate Mutations and Repair of Recoding Schemes

Figure 17:
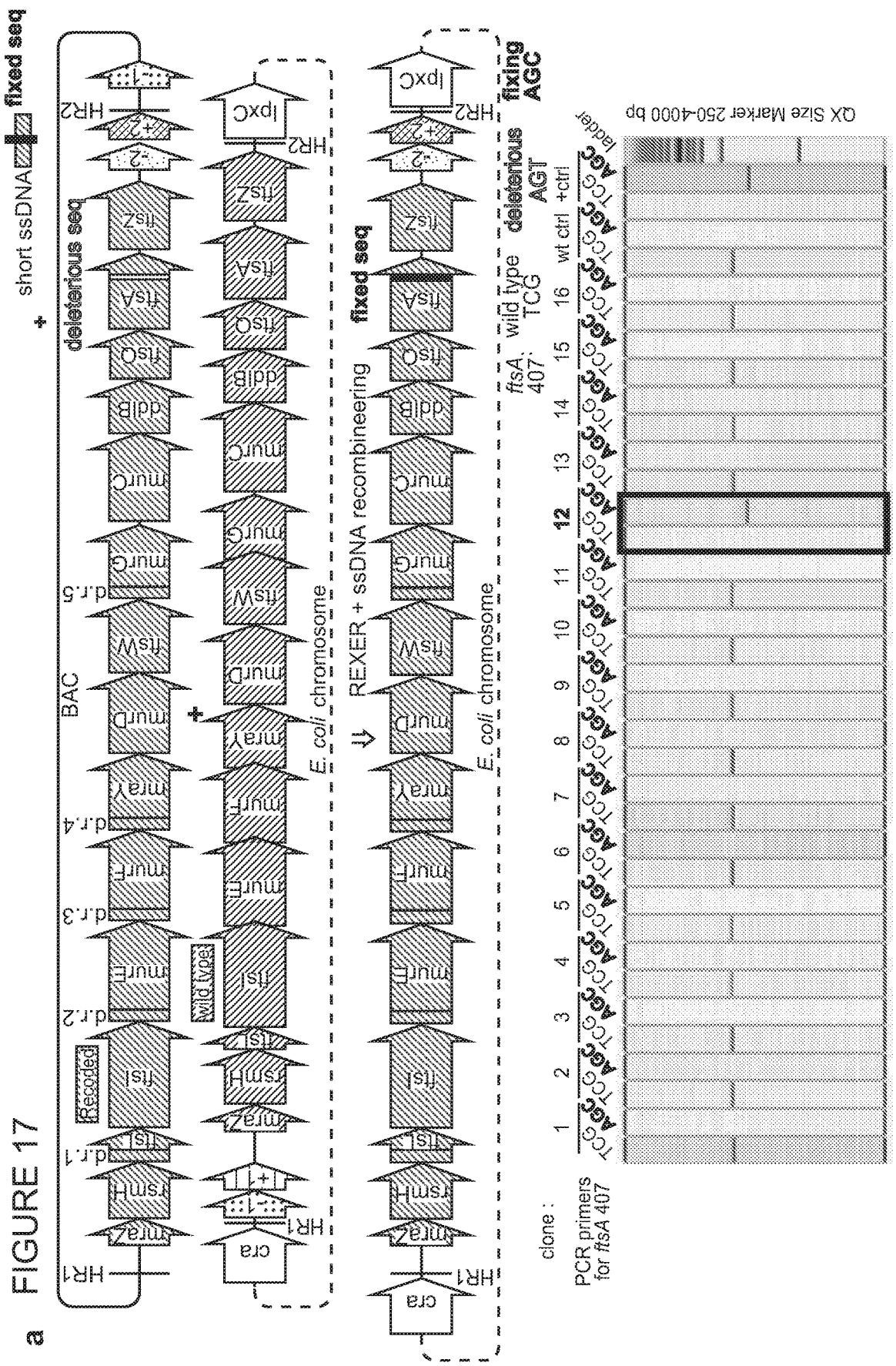
FIG. 17 (Extended Data FIG. 9) shows REXER can be combined with single strand DNA recombineering to fix short deleterious sequence on synthetic DNA. a. Using single stand DNA recombineering in combination with REXER to fix short deleterious stretch within the synthetic sequence. An single stand oligo of a total length of 90 nt was designed and synthesized to change the deleterious sequence of AGT in ftsA codon position 407 on the synthetic sequence to a tolerated sequence, AGC. The oligo sequence was designed based on the reverse strand of the synthetic sequence to bind the forward strand with the single nucleotide change positioned in the middle (45 from nt 5' end). The last two nucleotides in the 5' end of the oligo were substituted with phosphorothioate backbone to protect the oligo from unspecific exonuclease degradation. 0.2 nmol of the oligo was co-transformed into E. coli during the REXER experiment, and normal REXER procedure was carried out without any modification. b. Fixing short deleterious sequence on synthetic DNA with REXER+ssDNA recombineering. 16 clones from REXER double selection plates were randomly picked and subject to single nucleotide polymorphism (SNP) genotyping using primers specific for either the wildtype sequence in ftsA codon position 407 (TCG) or the fixed sequence (AGC). Primers specific for the wildtype sequence in ftsA codon position 407 (TCG) will only yield a PCR product of 437 bp for wildtype genomic template and no PCR product if the wildtype sequence TCG is changed to the fixed sequence AGC on this genomic locus. Primers specific for the fixed sequence in ftsA codon position 407 (AGC) will only yield a PCR product of 385 bp for the fixed genomic template and no PCR product if the wildtype sequence TCG remains on the locus. MDS42$^{rpsLK43IrK}$ was used as the wildtype control and a fully recoded clone from serine r.s.3 with verified ftsA 407 AGC as the positive control. SNP genotyping at ftsA codon position 407 identified one clone (clone 12, highlighted in orange) out of a total of 16 clones tested with fixed sequence AGC, which was then fully sequenced across the entire 20 kb recoding region and confirmed as fully recoded at all 83 targeted codon positions. All PCR products were analysed on QIAGEN QIAxcel Advanced machine using QIAxcel DNA Screening Kit with QX Alignment Marker 15 bp/5 kb and QX Size Marker 250-4000 bp.

We next demonstrated that mutation of the codon at position 407 in ftsA from AGT to AGC (the codon found at this position in recoding schemes 2 and 3) is sufficient to repair recoding scheme 1 (FIG. 13 b,c,d (supplementary FIG. 6b,c,d)). This mutation dramatically alters REXER mediated recoding, increasing the fraction of fully recoded sequences from 0% to 94% and the fraction of recoding at codon 407 of ftsA from 0% to 100% (FIG. 13 b,c,d (supplementary FIG. 6b,c,d)). We also successfully introduced this mutation into recoding scheme 1 by combining single stranded DNA recombineering with REXER (FIG. 17 (Extended Data FIG. 9)). The growth of *E. coli* was not affected by the successful recoding schemes (FIG. 13e (Supplementary FIG. 6e)). These results demonstrate that the major defect in recoding scheme 1 results from AGT being disallowed at position 407 of ftsA. Since TCG. TCT and AGC are allowed at position 407 of ftsA but AGT (which shares nucleotides with allowed codons at each position of the triplet) is disallowed, we conclude that the problem at this codon lies in the entire triplet rather than in the identity of specific nucleotides within the triplet. These experiments exemplify how REXER may be used to i) identify idiosyncratic positions in the genome that are refractory to recoding by otherwise well-tolerated recoding schemes. and ii) repair the recoding scheme by the introduction of alternative codons at these idiosyncratic positions.

In conclusion, we have generated an approach to enable both the programmed insertion of large synthetic DNA sequences into the *E. coli* genome and the replacement of sections of the *E. coli* genome with synthetic DNA. The approach combines the creation of a linear synthetic dsDNA cassette, via in vivo excision from an episomal replicon by CRISPR/Cas9, with lambda red mediated recombination coupled to simultaneous positive and negative selection to ensure integration at the target locus. The approach is very efficient, can be iterated, and will enable replacement of the entire *E. coli* genome with synthetic DNA in no more than 40 steps (FIG. 14 (Extended Data FIG. 6)), with each step taking a few days. The length of DNA that can be inserted in a single step exceeds that incorporated in naturally recombinogenic organisms. As both CRISPR systems and lambda red mediated recombination are active in other organisms we anticipate that the approach may be extended beyond *E. coli* and facilitate genome engineering in other organisms.

We have simultaneously recoded the genes in an essential operon using eight different well-defined synonymous recoding rules. Each recoding rule removes every occurrence of each target codon tested and replaces it with a defined synonym that, following genome wide application and cognate tRNA deletion, would enable unambiguous codon reassignment. We have defined synonymous substitutions that are deleterious at many positions and lead to poorly tolerated recoding schemes, and we have also defined other synonymous substitutions for the same target codons that are allowed at all positions investigated. Our results reveal dramatic differences in the extent to which different synonymous replacements for the same target codons are allowed in a group of genes encoding interacting proteins. Our approach also enables both the identification and repair of idiosyncratic positions within the 'recoding landscape' where a precise codon substitution that is allowed at many other positions in the operon is disallowed. Moreover we demonstrate that alternative recoding of idiosyncratic positions, that maintains target codon removal, can rescue a recoding scheme. Our investigation of precisely defined schemes for sense codon removal and synonymous replacement in many genes simultaneously enables the elimination of those recoding schemes that cannot be applied for genome recoding, and the identification of recoding schemes that are promising for genome-wide application.

Extended Data TABLE 4

Defining recording rules by codon adaptation index (cAi), tRNA adaptation index (tAi), and translation efficiency (t.E).

| | $cAiw_i$ | | $tAiw_i$ | | t.E | |
|---|---|---|---|---|---|---|
| Codon | Metric | Substitution | Metric | Substitution | Metric | Substitution |
| $TCG^{Ser}$ | 0.017 | $AGT^{Ser}$ | 0.165 | $AGC^{Ser}$ | 0.086 | $AGC^{Ser}$ |
| $TCA^{Ser}$ | 0.077 | $AGT^{Ser}$ | 0.125 | $AGC^{Ser}$ | 0.049 | $AGT^{Ser}$ |

Extended Data TABLE 4-continued

Defining recording rules by codon adaptation index (cAi), tRNA adaptation index (tAi), and translation efficiency (t.E).

| | $cAiw_i$ | | $tAiw_i$ | | t.E | |
|---|---|---|---|---|---|---|
| Codon | Metric | Substitution | Metric | Substitution | Metric | Substitution |
| $TCT^{Ser}$ | 1.000 | | 0.110 | | 0.034 | |
| $TCC^{Ser}$ | 0.744 | | 0.250 | | 0.057 | |
| $AGT^{Ser}$ | 0.085 | | 0.055 | | 0.044 | |
| $AGC^{Ser}$ | 0.410 | | 0.125 | | 0.088 | |

Extended Data Table 5. Protein functions, localizations, expression levels, and lengths of the genes in the essential cell division operon all simultaneously recoded in this work (a), and of individually recoded ribosomal and release factor 2 genes reported previously (b). In more detail, protein functions, localizations, expression levels (in parts per million), and lengths (both ORF length in bp and peptide length in amino acid count) of the genes in the essential cell division operon all simultaneously recoded in this work (a), and of individually recoded ribosomal and release factor 2 genes reported previously (b)[25] The numbers of codons targeted for removal according to different recoding schemes are also reported. The expression level data is from www.pax-db.org.

TABLE 5

| Gene | Function | Localisation | Protein level ppm | ORF length | Peptide length | Number of target codons | | | | | | | |
|---|---|---|---|---|---|---|---|---|---|---|---|---|---|
| | | | | | | r.s.1 | r.s.2 | r.s.3 | r.s.4 | r.s.5 | r.s.6 | r.s.7 | r.s.8 |
| a | | | | | | | | | | | | | |
| mraZ | Transcription factor | cytosol, nucleoid | 11.3 | 459 | 153 | 4 | 4 | 4 | 9 | 9 | 9 | 4 | 4 |
| rsmH | Methyltransferase | cytosol | 122.0 | 942 | 314 | 8 | 8 | 8 | 4 | 4 | 4 | 13 | 13 |
| ftsL | Cell division | membrane | 1.9 | 366 | 122 | 2 | 2 | 2 | 5 | 5 | 5 | 4 | 4 |
| ftsI | Cell division | membrane | 9.7 | 1767 | 589 | 9 | 9 | 9 | 15 | 15 | 15 | 38 | 38 |
| murE | Cell division | cytosol | 121.3 | 1488 | 496 | 5 | 5 | 5 | 10 | 10 | 10 | 47 | 47 |
| murF | Cell division | sytosol | 67.1 | 1359 | 453 | 7 | 7 | 7 | 12 | 12 | 12 | 34 | 34 |
| mraY | Cell division | membrane | 13.7 | 1083 | 361 | 5 | 5 | 5 | 9 | 9 | 9 | 16 | 16 |
| murD | Cell division | cytosol | 67.5 | 1317 | 439 | 3 | 3 | 3 | 12 | 12 | 12 | 36 | 36 |
| ftsW | Cell division | membrane | 2.7 | 1245 | 415 | 13 | 13 | 13 | 19 | 19 | 19 | 27 | 27 |
| murG | Cell division | membrane | 21.5 | 1068 | 356 | 5 | 5 | 5 | 11 | 11 | 11 | 34 | 34 |
| murC | Cell division | cytosol | 83.4 | 1476 | 492 | 2 | 2 | 2 | 12 | 12 | 12 | 29 | 29 |
| ddlB | Cell wall synthesis | cytosol | 33.1 | 921 | 307 | 7 | 7 | 7 | 15 | 15 | 15 | 24 | 24 |
| ftsQ | Cell division | membrane | 5.4 | 831 | 277 | 3 | 3 | 3 | 12 | 12 | 12 | 15 | 15 |
| ftsA | Cell division | membrane | 113.6 | 1263 | 421 | 10 | 10 | 10 | 9 | 9 | 9 | 23 | 23 |
| ftsZ | Cell division | cytosol | 633.6 | 1152 | 384 | 0 | 0 | 0 | 3 | 3 | 3 | 30 | 30 |
| | | Total number of target codons: | | | | 83 | 83 | 83 | 157 | 157 | 157 | 374 | 374 |
| b | | | | | | | | | | | | | |
| rpmH | Protein translation | cytosol | 4075.7 | 141 | 47 | 0 | 0 | 0 | 0 | 0 | 0 | 9 | 9 |
| rpmD | Protein translation | cytosol | 3046.3 | 180 | 60 | 0 | 0 | 0 | 2 | 2 | 2 | 20 | 20 |
| rpmC | Protein translation | cytosol | 5980.0 | 192 | 64 | 0 | 0 | 0 | 1 | 1 | 1 | 12 | 12 |
| rpsR | Protein translation | cytosol | 5806.5 | 228 | 76 | 0 | 0 | 0 | 0 | 0 | 0 | 2 | 2 |
| rpmB | Protein translation | cytosol | 5502.1 | 237 | 79 | 0 | 0 | 0 | 1 | 1 | 1 | 5 | 5 |
| rpsP | Protein translation | cytosol | 6611.2 | 249 | 83 | 3 | 3 | 3 | 2 | 2 | 2 | 16 | 16 |
| rpsQ | Protein translation | cytosol | 2179.3 | 255 | 85 | 1 | 1 | 1 | 0 | 0 | 0 | 3 | 3 |
| rpmA | Protein translation | cytosol | 4380.7 | 258 | 86 | 0 | 0 | 0 | 0 | 0 | 0 | 3 | 3 |
| rpsS | Protein translation | cytosol | 3094.6 | 279 | 93 | 0 | 0 | 0 | 0 | 0 | 0 | 3 | 3 |
| rplW | Protein translation | cytosol | 2091.7 | 303 | 101 | 0 | 0 | 0 | 1 | 1 | 1 | 7 | 7 |
| rpsN | Protein translation | cytosol | 4612.5 | 306 | 102 | 2 | 2 | 2 | 0 | 0 | 0 | 9 | 9 |
| rplU | Protein translation | cytosol | 1856.1 | 312 | 104 | 0 | 0 | 0 | 4 | 4 | 4 | 10 | 10 |
| rpsJ | Protein translation | cytosol | 3472.7 | 312 | 104 | 0 | 0 | 0 | 1 | 1 | 1 | 9 | 9 |
| rplX | Protein translation | cytosol | 4456.0 | 315 | 105 | 1 | 1 | 1 | 2 | 2 | 2 | 5 | 5 |
| rplV | Protein translation | cytosol | 7848.2 | 333 | 111 | 0 | 0 | 0 | 1 | 1 | 1 | 5 | 5 |
| rplS | Protein translation | cytosol | 3859.3 | 348 | 116 | 0 | 0 | 0 | 0 | 0 | 0 | 4 | 4 |
| rplR | Protein translation | cytosol | 6367.3 | 354 | 118 | 0 | 0 | 0 | 0 | 0 | 0 | 8 | 8 |
| rplT | Protein translation | cytosol | 3291.4 | 357 | 119 | 0 | 0 | 0 | 0 | 0 | 0 | 9 | 9 |
| rpsM | Protein translation | cytosol | 5733.1 | 357 | 119 | 1 | 1 | 1 | 0 | 0 | 0 | 10 | 10 |
| rplL | Protein translation | cytosol | 14543.5 | 366 | 122 | 0 | 0 | 0 | 0 | 0 | 0 | 8 | 8 |

TABLE 5-continued

| Gene | Function | Localisation | Protein level ppm | ORF length | Peptide length | Number of target codons | | | | | | | |
|---|---|---|---|---|---|---|---|---|---|---|---|---|---|
| | | | | | | r.s.1 | r.s.2 | r.s.3 | r.s.4 | r.s.5 | r.s.6 | r.s.7 | r.s.8 |
| rplN | Protein translation | cytosol | 8866.6 | 372 | 124 | 1 | 1 | 1 | 2 | 2 | 2 | 3 | 3 |
| rpsL | Protein translation | cytosol | 5532.8 | 375 | 125 | 0 | 0 | 0 | 1 | 1 | 1 | 10 | 10 |
| rplQ | Protein translation | cytosol | 4272.8 | 384 | 128 | 0 | 0 | 0 | 1 | 1 | 1 | 5 | 5 |
| rpsK | Protein translation | cytosol | 2900.5 | 390 | 130 | 1 | 1 | 1 | 0 | 0 | 0 | 5 | 5 |
| rpsH | Protein translation | cytosol | 3828.3 | 393 | 131 | 0 | 0 | 0 | 0 | 0 | 0 | 1 | 1 |
| rpsI | Protein translation | cytosol | 3410.8 | 393 | 131 | 0 | 0 | 0 | 2 | 2 | 2 | 5 | 5 |
| rplP | Protein translation | cytosol | 3778.1 | 411 | 137 | 0 | 0 | 0 | 2 | 2 | 2 | 9 | 9 |
| rplM | Protein translation | cytosol | 4268.0 | 429 | 143 | 0 | 0 | 0 | 0 | 0 | 0 | 9 | 9 |
| rplO | Protein translation | cytosol | 5111.6 | 435 | 145 | 1 | 1 | 1 | 1 | 1 | 1 | 3 | 3 |
| rplJ | Protein translation | cytosol | 7731.6 | 498 | 166 | 1 | 1 | 1 | 2 | 2 | 2 | 3 | 3 |
| rpsE | Protein translation | cytosol | 7657.3 | 504 | 168 | 0 | 0 | 0 | 1 | 1 | 1 | 11 | 11 |
| rplF | Protein translation | cytosol | 5012.1 | 534 | 178 | 0 | 0 | 0 | 0 | 0 | 0 | 5 | 5 |
| rpsG | Protein translation | cytosol | 8660.2 | 540 | 180 | 0 | 0 | 0 | 2 | 2 | 2 | 11 | 11 |
| rplE | Protein translation | cytosol | 3489.1 | 540 | 180 | 0 | 0 | 0 | 2 | 2 | 2 | 5 | 5 |
| rplD | Protein translation | cytosol | 3469.9 | 606 | 202 | 0 | 0 | 0 | 1 | 1 | 1 | 5 | 5 |
| rpsD | Protein translation | cytosol | 5187.4 | 621 | 207 | 1 | 1 | 1 | 3 | 3 | 3 | 9 | 9 |
| rplC | Protein translation | cytosol | 4460.3 | 630 | 210 | 0 | 0 | 0 | 0 | 0 | 0 | 6 | 6 |
| rpsC | Protein translation | cytosol | 5755.0 | 702 | 234 | 0 | 0 | 0 | 0 | 0 | 0 | 2 | 2 |
| rpsB | Protein translation | cytosol | 4324.5 | 726 | 242 | 0 | 0 | 0 | 0 | 0 | 0 | 1 | 1 |
| rplB | Protein translation | cytosol | 5658.4 | 822 | 274 | 1 | 1 | 1 | 1 | 1 | 1 | 16 | 16 |
| prlB | Protein translation | cytosol | 570.9 | 1099 | 366 | 0 | 0 | 0 | 0 | 0 | 0 | 8 | 8 |
| rpsA | Protein translation | cytosol | 2649.1 | 1674 | 558 | 0 | 0 | 0 | 0 | 0 | 0 | 3 | 3 |
| | | | | Total number of target codons: | | 14 | 14 | 14 | 36 | 36 | 36 | 292 | 292 |

REFERENCES

1. Cello, J., Paul, A V. & Wimmer. E. Chemical synthesis of poliovirus cDNA: generation of infectious virus in the absence of natural template. Science 297, 1016-1018 (2002).
2. Chan. L. Y., Kosuri, S. & Endy, D. Refactoring bacteriophage T7. Molecular Systems Biology 1, 2005.0018-E10 (2005).
3. Itaya. M., Tsuge, K., Koizumi, M. & Fujita, K. Combining two genomes in one cell: stable cloning of the Synechocystis PCC6803 genomic in the Bacillus subtilis 168 genome, Proc. Natl. Acad. Sci. U.S.A. 102, 15971-15976 (2005).
4. Gibson. D. G. et al. Complete chemical synthesis, assembly, and cloning of a Mycoplasma genitalium genome. Science 319, 1215-1220 (2008).
5. Gibson, D. G. et al. Creation of a Bacterial Cell Controlled by a Chemically Synthesized Genome. Science 329, 52-56 (2010).
6. Annaluru, N. et al. Total synthesis of a functional designer eukaryotic chromosome. Science 344, 55-58 (2014).
7. Kudla, G., Murray. A. W., Tollervey. D. & Plotkin. J. B. Coding-sequence determinants of gene expression in Escherichia coli. Science 324, 255-258 (2009).
8. Ro, D.-K. et al. Production of the antimalarial drug precursor artemisinic acid in engineered yeast. Nature 440, 940-943 (2006).
9. Chin, J. W. Reprogramming the genetic code. Science 336, 428-429 (2012).
10. Mukai, T. et al. Reassignment of a rare sense codon to a non-canonical amino acid in Escherichia coli. Nucleic Acids Research 43, 8111-8122 (2015).
11. Mandell, D. J. et al. Biocontainment of genetically modified organisms by synthetic protein design. Nature 518, 55-60 (2015).
12. Lajoie, M. J. et al. Genomically Recoded Organisms Expand Biological Functions. Science 342, 357-360 (2013).
13. Wang, H. H. et al. Programming cells by multiplex genome engineering and accelerated evolution. Nature 460, 894-898 (2009)
14. Datsenko, K. A. & Wanner, B. L. One-step inactivation of chromosomal genes in Escherichia coli K-12 using PCR products. Proc. Natl. Acad. Sci. U.S.A. 97, 6640-6645 (2000).
15. Pósfai, G. et al. Emergent properties of reduced-genome Escherichia coli. Science 312, 1044-1046 (2006).
16. Jiang. W., Cox, D., Zhang. F., Bikard, D. & Marraffini, L. A. RNA-guided editing of bacterial genomes using CRISPR-Cas systems. Nature Biotechnology 31, 233-239 (2013).
17. Bryksin, A. V. & Matsumura, I. Rational Design of a Plasmid Origin That Replicates Efficiently in Both Gram-Positive and Gram-Negative Bacteria. PLoS ONE 5, e13244 (2010).
18. Kouprina, N., Noskov, V. N. & Larionov, V. Selective isolation of large chromosomal regions by transformation-associated recombination cloning for structural and functional analysis of mammalian genomes. Methods Mo. Biol. 349, 85-101 (2006).
19. Sorensen, M. A. & Pedersen, S. Absolute in vivo translation rates of individual codons in Escherichia coli. The two glutamic acid codons GAA and GAG are translated with a threefold difference in rate. Journal of Molecular Biology 222, 265-280 (1991).
20. Curran. J. F. & Yarus, M. Rates of aminoacyl-tRNA selection at 29 sense codons in vivo. Journal of Molecular Biology 209, 65-77 (1989).
21. Cho, B.-K. et al. The transcription unit architecture of the Escherichia coli genome. Nature Biotechnology 27, 1043-1049 (2009).
22. Li, G.-W., Oh, E. & Weissman, J. S. The anti-Shine-Dalgarno sequence drives translational pausing and codon choice in bacteria. Nature 484, 538-541 (2012).
23. Kimchi-Sarfaty, C. et al. A 'Silent' Polymorphism in the MDR1 Gene Changes Substrate Specificity. Science 315, 525-528 (2007).

24. Zhang. G., Hubalewska, M. & Ignatova, Z. Transient ribosomal attenuation coordinates protein synthesis and co-translational folding. *Nat Struct Mol Biol* 16, 274-280 (2009).
25. Lajoie, M. J. et al. Probing the Limits of Genetic Recoding in Essential Genes. *Science* 342, 361-363 (2013).
26 Wang. K. et al. Optimized orthogonal translation of unnatural amino acids enables spontaneous protein double-labelling and FRET. *Nature Chemistry* 6, 393-403 (2014).
27. Sharp. P. M. & Li, W. H. The codon Adaptation Index—a measure of directional synonymous codon usage bias, and its potential applications. *Nucleic Acids Research* 15, 1281-1295 (1987).
28. Reis, dos, M., Savva, R. & Wemisch. L. Solving the riddle of codon usage preferences: a test for translational selection. *Nucleic Acids Research* 32, 5036-5044 (2004).
29. Tuller, T., Waldman, Y. Y., Kupiec, M. & Ruppin, E. Translation efficiency is determined by both codon bias and folding energy. *Proceedings of the National Academy of Sciences* 107, 3645-3650 (2010).
30. Baba, T et al. Construction of *Escherichia coli* K-12 in-frame, single-gene knockout mutants: the Keio collection. *Molecular Systems Biology* 2, 2006.0008-1 (2006).
31. Pratviel-Sosa, F., Mengin-Lecreulx. D. & van Heijenoort, J. Over-production, purification and properties of the uridine diphosphate N-acetylmuramoyl-L-alanine:D-glutamate ligase from *Escherichia coli*. *Eur. J. Biochem.* 202, 1169-1176 (1991).
32 Carson, M. J., Barondess. J. & Beckwith, J. The FtsQ protein of *Escherichia coli*: membrane topology, abundance, and cell division phenotypes due to overproduction and insertion mutations. *J Bacteriol* 173, 2187-2195 (1991).
33. Dai, K. & Lutkenhaus, J. The proper ratio of FtsZ to FtsA is required for cell division to occur in *Escherichia coli*. *J Bacteriol* 174, 6145-6151 (1992).
34. Dewar, S. J., Begg. K. J. & Donachie, W. D. Inhibition of cell division initiation by an imbalance in the ratio of FtsA to FtsZ. *J Bacteriol* 174, 6314-6316 (1992).
35. Weiss. D. S. et al. Localization of the *Escherichia coli* cell division protein FtsI (PBP3) to the division site and cell pole. *Mol Microbiol* 25, 671-681 (1997).
36. Eraso. J. M. et al. The highly conserved MraZ protein is a transcriptional regulator in *Escherichia coli*. *J Bacteriol* 196, 2053-2066 (2014)
37. Geis. A. & Plapp, R. Phospho-N-acetylmuramoyl-pentapeptide-transferase of *Escherichia coli* K12. Properties of the membrane-bound and the extracted and partially purified enzyme. *Biochim. Biophys. Acta* 527, 414-424 (1978).
38. Pla. J., Dopazo, A. & Vicente. M. The native form of FtsA, a septal protein of *Escherichia coli*, is located in the cytoplasmic membrane. *J Bacteriol* 172, 5097-5102 (1990).
39. Nguyen-Distèche, M., Fraipont, C., Buddelmeijer, N. & Nanninga, N. The structure and function of *Escherichia coli* penicillin-binding protein 3. *Cell. Mol. Life Sci.* 54, 309-316 (1998).
40. Ha. S., Walker. D., Shi, Y. & Walker, S. The 1.9 A crystal structure of *Escherichia coli* MurG, a membrane-associated glycosyltransferase involved in peptidoglycan biosynthesis. *Protein Sci.* 9, 1045-1052 (2000).
41. Urbanus, M. L. et al. Sec-dependent membrane protein insertion: sequential interaction of nascent FtsQ with SecY and YidC. *EMBO Rep* 2, 524-529 (2001).
42. Fraipont, C. et al. The integral membrane FtsW protein and peptidoglycan synthase PBP3 form a subcomplex in *Escherichia coli*. *Annut Rev Microbiol* 157, 251-259 (2011).
43. Khadna, A S. & Senes. A. The transmembrane domains of the bacterial cell division proteins FtsB and FtsL form a stable high-order oligomer. *Biochemistry* 52, 7542-7550 (2013).
44. Grosjean, H. J, de Henau, S. & Crothers, D. M On the physical basis for ambiguity in genetic coding interactions. *Proc. Natl. Acad. Sci. U.S.A.* 75, 610-614 (1978).
45. Curran, J. F. Decoding with the A:I wobble pair is inefficient. *Nucleic Acids Research* 23, 683-688 (1995).
46. Dong, H., Nilsson, L. & Kurland, C. G. Co-variation of tRNA abundance and codon usage in *Escherichia coli* at different growth rates. *Journal of Molecular Biology* 260, 649-663 (1996).
47. Ishii. N. et al. Multiple high-throughput analyses monitor the response of *E. coli* to perturbations *Science* 316, 593-597 (2007).

Supplementary References for Example 7

Hutchison. C. A. et al. Design and synthesis of a minimal bacterial genome. Science 351, aad6253-aad6253 (2016).

Itaya. M., Fujita, K., Ikeuchi, M., Koizumi. M. & Tsuge, K. Stable positional cloning of long continuous DNA in the *Bacillus subtilis* genome vector. Journal of Biochemistry 134, 513-519 (2003).

Krishnakumar, R. et al. Simultaneous non-contiguous deletions using large synthetic DNA and site-specific recombinases. Nucleic Acids Research 42, e111-e111 (2014)

Quax, T. E. F. et al. Differential translation tunes uneven production of operon-encoded proteins. Cell Rep 4, 938-944 (2013).

Quax, T. E. F., Claassens. N. J., Söll, D. & van der Oost, J. Codon Bias as a Means to Fine-Tune Gene Expression. Mol. Cell 59, 149-161(2015).

Li. G.-W., Burkhardt, D., Gross. C. & Weissman, J. S. Quantifying absolute protein synthesis rates reveals principles underlying allocation of cellular resources. Cell 157, 624-635 (2014).

Giegé, R., Sissler, M. & Florentz, C. Universal rules and idiosyncratic features in tRNA identity. Nucleic Acids Research 26, 5017-5035 (1998).

Newton, C. R. et al. Analysis of any point mutation in DNA. The amplification refractory mutation system (ARMS). Nucleic Acids Research 17, 2503-2516 (1989).

Gallagher. R. R., Li, Z., Lewis. A. O. & Isaacs, F. J. Rapid editing and evolution of bacterial genomes using libraries of synthetic DNA. Nat Protoc 9, 2301-2316 (2014).

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

What is claimed:

1. A method comprising
   (a) providing a host cell
       said host cell comprising an episomal replicon,
       said episomal replicon comprising a donor nucleic acid sequence,
       said host cell further comprising a target nucleic acid;
   (b) providing helper protein(s) capable of supporting nucleic acid recombination in said host cell;
   (c) providing helper protein(s) and/or RNAs capable of supporting nucleic acid excision in said host cell
       wherein said donor nucleic acid sequence comprises in order: 5'-homologous recombination sequence 1-sequence of interest-homologous recombination sequence 2-3'
       wherein said sequence of interest comprises both a positive selectable marker and a first negative selectable marker;
   (d) inducing excision of said donor nucleic acid sequence;
   (e) incubating to allow recombination between the excised donor nucleic acid and said target nucleic acid; and
   (f) selecting for recombinants having incorporated said donor nucleic acid into said target nucleic acid.

2. The method according to claim 1, wherein said target nucleic acid comprises in order: 5'-homologous recombination sequence 1-second negative selectable marker-homologous recombination sequence 2-3'.

3. The method according to claim 2, wherein selecting for recombinants having incorporated said donor nucleic acid into said target nucleic acid comprises selection for gain of the positive selectable marker of the donor nucleic acid and loss of the second negative selectable marker of the target nucleic acid.

4. The method according to claim 3, wherein selection for gain of the positive selectable marker of the donor nucleic acid and loss of the second negative selectable marker of the target nucleic acid is carried out simultaneously.

5. The method according to claim 3, wherein selection for gain of the positive selectable marker of the donor nucleic acid and loss of the second negative selectable marker of the target nucleic acid comprises sequential selection for said positive and negative markers, or sequential selection for said negative and positive markers.

6. The method according to claim 1, further comprising the step of
   (ii) inducing at least one double stranded break in the target nucleic acid sequence, wherein said double stranded break is between said homologous recombination sequence 1 and said homologous recombination sequence 2.

7. The method according to claim 6, wherein at least two double stranded breaks are induced in the target nucleic acid sequence, wherein each said double stranded break is between said homologous recombination sequence 1 and said homologous recombination sequence 2.

8. The method according to claim 1, wherein said excised donor nucleic acid begins with said homologous recombination sequence 1 and ends with said homologous recombination sequence 2.

9. The method according to claim 1, wherein said episomal replicon comprises a negative selectable marker independent of the donor nucleic acid sequence.

10. The method according to claim 9, wherein said method comprises the further step of selecting for loss of the episomal replicon by selecting for loss of said negative selectable marker independent of the donor nucleic acid sequence.

11. The method according to claim 1, wherein said episomal replicon comprises in order: excision cut site 1-donor nucleic acid sequence-excision cut site 2.

12. The method according to claim 1, wherein said target nucleic acid possesses its own origin of replication capable of functioning within said host cell.

13. The method according to claim 1, wherein at least one of said episomal replicon and said target nucleic acid is a plasmid nucleic acid.

14. The method according to claim 13, wherein said episomal replicon is a first plasmid nucleic acid and said target nucleic acid is a second plasmid nucleic acid.

15. The method according to claim 1, wherein at least one of said episomal replicon and said target nucleic acid is a bacterial artificial chromosome (BAC).

16. The method according to claim 15, wherein said episomal replicon is a first bacterial artificial chromosome (BAC) and said target nucleic acid is a second bacterial artificial chromosome (BAC).

17. The method according to claim 1, wherein said target nucleic acid is the host cell genome.

18. The method according to claim 1, wherein the first negative selectable marker is selected from the group consisting of sacB or rpsL.

19. The method according to claim 1, wherein the positive selectable marker is selected from the group consisting of chloramphenicol resistance (CmR) or kanamycin resistance (KanR).

20. The method according to claim 1, wherein the step of selecting for recombinants comprises sequential selection for said positive and negative markers, sequential selection for said negative and positive markers, or simultaneous selection for said positive and negative markers.

21. The method according to claim 1, wherein said helper protein(s) and/or RNAs capable of supporting nucleic acid excision comprise CRISPR/Cas9 proteins/RNAs.

22. The method according to claim 1, wherein said helper protein(s) capable of supporting nucleic acid recombination comprise lambda Red proteins.

23. A method of assembling a synthetic genome, the method comprising performing the steps according to claim 1 with a first donor nucleic acid sequence, choosing further donor sequence(s) contiguous with said first donor nucleic acid sequence, and repeating said steps with said further donor nucleic acid sequence(s) until the synthetic genome has been assembled.

* * * * *

UNITED STATES PATENT AND TRADEMARK OFFICE
CERTIFICATE OF CORRECTION

| | | |
|---|---|---|
| PATENT NO. | : 11,667,933 B2 | Page 1 of 1 |
| APPLICATION NO. | : 16/311265 | |
| DATED | : June 6, 2023 | |
| INVENTOR(S) | : Fredens et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1104 days.

Signed and Sealed this
Nineteenth Day of August, 2025

Coke Morgan Stewart
*Acting Director of the United States Patent and Trademark Office*

SEQUENCE LISTING

<160> NUMBER OF SEQ ID NOS: 13

<210> SEQ ID NO 1
<211> LENGTH: 681
<212> TYPE: DNA
<213> ORGANISM: Coliphage lambda

<400> SEQUENCE: 1

```
atgacaccgg acattatcct gcagcgtacc gggatcgatg tgagagctgt cgaacagggg      60
gatgatgcgt ggcacaaatt acggctcggc gtcatcaccg cttcagaagt tcacaacgtg     120
atagcaaaac cccgctccgg aaagaagtgg cctgacatga aatgtccta ctttcacacc      180 ctgcttgctg aggtttgcac cggtgtggct ccggaagtta acgctaaagc actggcctgg     240
ggaaaacagt acgagaacga cgccagaacc ctgtttgaat tcacttccgg cgtgaatgtt     300
actgaatccc cgatcatcta tcgcgacgaa agtatgcgta ccgcctgctc tcccgatggt     360
ttatgcagtg acggcaacgg ccttgaactg aaatgcccgt ttacctcccg ggatttcatg     420
aagttccggc tcggtggttt cgaggccata agtcagctt acatggccca ggtgcagtac      480
agcatgtggg tgacgcgaaa aaatgcctgg tactttgcca actatgaccc gcgtatgaag     540
cgtgaaggcc tgcattatgt cgtgattgag cgggatgaaa agtacatggc gagttttgac     600
gagatcgtgc cggagttcat cgaaaaaatg gacgaggcac tggctgaaat tggttttgta     660
tttggggagc aatggcgata g                                               681
```

<210> SEQ ID NO 2
<211> LENGTH: 786
<212> TYPE: DNA
<213> ORGANISM: Coliphage lambda

<400> SEQUENCE: 2

```
atgagtactg cactcgcaac gctggctggg aagctggctg aacgtgtcgg catggattct      60
gtcgacccac aggaactgat caccactctt cgccagacgg catttaaagg tgatgccagc     120
gatgcgcagt tcatcgcatt actgatcgtt gccaaccagt acggccttaa tccgtggacg     180
aaagaaattt acgcctttcc tgataagcag aatggcatcg ttccggtggt gggcgttgat     240
ggctggtccc gcatcatcaa tgaaaaccag cagtttgatg gcatggactt tgagcaggac     300
aatgaatcct gtacatgccg gatttaccgc aaggaccgta atcatccgat ctgcgttacc     360
gaatggatgg atgaatgccg ccgcgaacca ttcaaaactc gcgaaggcag agaaatcacg     420
gggccgtggc agtcgcatcc caaacggatg ttacgtcata agccatgat tcagtgtgcc      480 cgtctggcct tcggatttgc tggtatctat gacaaggatg aagccgagcg cattgtcgaa     540
aatactgcat acactgcaga acgtcagccg gaacgcgaca tcactccggt taacgatgaa     600
accatgcagg agattaacac tctgctgatc gccctgata aaacatggga tgacgactta     660
ttgccgctct gttcccagat atttcgccgc gacattcgtg catcgtcaga actgacacag     720
gccgaagcag taaagctct tggattcctg aaacagaaag ccgcagagca gaaggtggca      780
gcatga                                                                786
```

<210> SEQ ID NO 3
<211> LENGTH: 417
<212> TYPE: DNA
<213> ORGANISM: Coliphage lambda

<400> SEQUENCE: 3

```
atggatatta atactgaaac tgagatcaag caaaagcatt cactaacccc ctttcctgtt      60
ttcctaatca gcccggcatt tcgcgggcga tattttcaca gctatttcag gagttcagcc     120
atgaacgctt attacattca ggatcgtctt gaggctcaga gctgggcgcg tcactaccag     180
cagctcgccc gtgaagagaa agaggcagaa ctggcagacg acatggaaaa aggcctgccc     240
cagcacctgt ttgaatcgct atgcatcgat catttgcaac gccacggggc cagcaaaaaa     300
tccattaccc gtgcgtttga tgacgatgtt gagtttcagg agcgcatggc agaacacatc     360
cggtacatgg ttgaaaccat tgctcaccac caggttgata ttgattcaga ggtataa       417
```

<210> SEQ ID NO 4
<211> LENGTH: 1422
<212> TYPE: DNA
<213> ORGANISM: Unknown
<220> FEATURE:
<223> OTHER INFORMATION: SacB

<400> SEQUENCE: 4

```
atgaacatca aaagtttgc aaaacaagca acagtattaa cctttactac cgcactgctg       60
gcaggaggcg caactcaagc gtttgcgaaa gaaacgaacc aaaagccata taggaaaaca     120
tacggcattt cccatattac acgccatgat atgctgcaaa tccctgaaca gcaaaaaaat     180
gaaaaatata agttcctga gttcgattcg tccacaatta aaaatatctc ttctgcaaaa     240
ggcctggacg tttgggacag ctggccatta caaaacactg acggcactgt cgcaaactat     300
cacggctacc acatcgtctt tgcattagcc ggagatccta aaaatgcgga tgacacatcg     360
atttacatgt tctatcaaaa agtcggcgaa acttctattg acagctggaa aaacgctggc     420
cgcgtcttta aagacagcga caaattcgat gcaaatgatt ctatcctaaa agaccaaaca     480
caagaatggt caggttcagc cacatttaca tctgacggaa aaatccgttt attctacact     540
gatttctccg gtaaacatta cggcaaacaa acactgacaa ctgcacaagt taacgtatca     600
gcatcagaca gctctttgaa catcaacggt gtagaggatt ataaatcaat ctttgacggt     660
gacggaaaaa cgtatcaaaa tgtacagcag ttcatcgatg aaggcaacta cagctcaggc     720
gacaaccata cgctgagaga tcctcactac gtagaagata aaggccacaa atacttagta     780
tttgaagcaa acactggaac tgaagatggc taccaaggcg aagaatcttt atttaacaaa     840
gcatactatg caaaagcac atcattcttc cgtcaagaaa gtcaaaaact tctgcaaagc     900
gataaaaaac gcacggctga gttagcaaac ggcgctctcg gtatgattga gctaaacgat     960
gattacacac tgaaaaaagt gatgaaaccg ctgattgcat ctaacacagt aacagatgaa    1020
attgaacgcg cgaacgtctt taaaatgaac ggcaaatggt acctgttcac tgactccgc     1080
ggatcaaaaa tgacgattga cggcattacg tctaacgata tttacatgct tggttatgtt    1140
tctaattctt taactggccc atacaagccg ctgaacaaaa ctggccttgt gttaaaaatg    1200
gatcttgatc ctaacgatgt aaccttact tactcacact tcgctgtacc tcaagcgaaa    1260
ggaaacaatg tcgtgattac aagctatatg acaaacagag gattctacgc agacaaacaa    1320
tcaacgtttg cgcctagctt cctgctgaac atcaaaggca agaaaacatc tgttgtcaaa    1380
gacagcatcc ttgaacaagg acaattaaca gttaacaaat aa                       1422
```

<210> SEQ ID NO 5
<211> LENGTH: 375
<212> TYPE: DNA

<213> ORGANISM: Unknown
<220> FEATURE:
<223> OTHER INFORMATION: rpsL

<400> SEQUENCE: 5

| | |
|---|---|
| atggcaacag ttaaccagct ggtacgcaaa ccacgtgctc gcaaagttgc gaaaagcaac | 60 |
| gtgcctgcgc tggaagcatg cccgcaaaaa cgtggcgtat gtactcgtgt atatactacc | 120 |
| actcctaaaa aaccgaactc cgcgctgcgt aaagtatgcc gtgttcgtct gactaacggt | 180 |
| ttcgaagtga cttcctacat cggtggtgaa ggtcacaacc tgcaggagca ctccgtgatc | 240 |
| ctgatccgtg gcggtcgtgt taaagacctc ccgggtgttc gttaccacac cgtacgtggt | 300 |
| gcgcttgact gctccggcgt taaagaccgt aagcaggctc gttccaagta tggcgtgaag | 360 |
| cgtcctaagg cttaa | 375 |

<210> SEQ ID NO 6
<211> LENGTH: 984
<212> TYPE: DNA
<213> ORGANISM: Unknown
<220> FEATURE:
<223> OTHER INFORMATION: PheS_T251A_A294G

<400> SEQUENCE: 6

| | |
|---|---|
| atgtcacatc tcgcagaact ggttgccagt gcgaaggcgg ccattagcca ggcgtcagat | 60 |
| gttgccgcgt tagataatgt gcgcgtcgaa tatttgggta aaaaagggca cttaacccct | 120 |
| cagatgacga ccctgcgtga gctgccgcca gaagagcgtc cggcagctgg tgcggttatc | 180 |
| aacgaagcga aagagcaggt tcagcaggcg ctgaatgcgc gtaaagcgga actggaaagc | 240 |
| gctgcactga atgcgcgtct ggcggcggaa acgattgatg tctctctgcc aggtcgtcgc | 300 |
| attgaaaacg gcggtctgca tccggttacc cgtaccatcg accgtatcga agtttcttc | 360 |
| ggtgagcttg gctttaccgt ggcaaccggg ccggaaatcg aagacgatta tcataacttc | 420 |
| gatgctctga acattcctgg tcaccacccg gcgcgcgctg accacgacac tttctggttt | 480 |
| gacactaccc gcctgctgcg tacccagacc tctggcgtac agatccgcac catgaaagcc | 540 |
| cagcagccac cgattcgtat catcgcgcct ggccgtgttt atcgtaacga ctacgaccag | 600 |
| actcacacgc cgatgttcca tcagatggaa ggtctgattg ttgataccaa catcagcttt | 660 |
| accaacctga aaggcacgct gcacgacttc ctgcgtaact ctttgagga agatttgcag | 720 |
| attcgcttcc gtccttccta cttcccgttt gccgaacctt ctgcagaagt ggacgtcatg | 780 |
| ggtaaaaacg gtaaatggct ggaagtgctg ggctgcggga tggtgcatcc gaacgtgttg | 840 |
| cgtaacgttg gcatcgaccc ggaagtttac tctggtttcg gcttcgggat ggggatggag | 900 |
| cgtctgacta tgttgcgtta cggcgtcacc gacctgcgtt cattcttcga aaacgatctg | 960 |
| cgtttcctca aacagtttaa ataa | 984 |

<210> SEQ ID NO 7
<211> LENGTH: 660
<212> TYPE: DNA
<213> ORGANISM: Unknown
<220> FEATURE:
<223> OTHER INFORMATION: cmR

<400> SEQUENCE: 7

| | |
|---|---|
| atggagaaaa aaatcactgg atataccacc gttgatatat cccaatggca tcgtaaagaa | 60 |
| cattttgagg catttcagtc agttgctcaa tgtacctata accagaccgt tcagctggat | 120 |
| attacggcct ttttaaagac cgtaaagaaa aataagcaca gtttatcc ggcctttatt | 180 |

```
cacattcttg cccgcctgat gaatgctcat ccggaattcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt tccctaaagg gtttattgag    420
aatatgtttt tcgtctcagc caatccctgg gtgagtttca ccagttttga tttaaacgtg    480
gccaatatgg acaacttctt cgccccgtt  ttcaccgtgg gcaaatatta tacgcaaggc    540
gacaaggtgc tgatgccgct ggcgattcag gttcatcatg ccgtctgtga tggcttccat    600
gtcggcagaa tgcttaatga attacaacag tactgcgatg agtggcaggg cggggcgtaa    660
```

```
<210> SEQ ID NO 8
<211> LENGTH: 795
<212> TYPE: DNA
<213> ORGANISM: Unknown
<220> FEATURE:
<223> OTHER INFORMATION: KanR

<400> SEQUENCE: 8
```

```
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caggacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795
```

```
<210> SEQ ID NO 9
<211> LENGTH: 30
<212> TYPE: DNA
<213> ORGANISM: Enterobacteria phage RB3

<400> SEQUENCE: 9
```

```
tatgtatctt ttgcgtgtac ctttaacttc                                     30
```

```
<210> SEQ ID NO 10
<211> LENGTH: 4107
<212> TYPE: DNA
<213> ORGANISM: Unknown
<220> FEATURE:
<223> OTHER INFORMATION: Cas9

<400> SEQUENCE: 10
```

```
atggataaga aatactcaat aggcttagat atcggcacaa atagcgtcgg atgggcggtg     60
atcactgatg aatataaggt tccgtctaaa aagttcaagg ttctgggaaa tacagaccgc    120
```

```
cacagtatca aaaaaaatct tatagggct cttttatttg acagtggaga gacagcggaa      180
gcgactcgtc tcaaacggac agctcgtaga aggtatacac gtcggaagaa tcgtatttgt      240
tatctacagg agatttttc aaatgagatg gcgaaagtag atgatagttt ctttcatcga      300
cttgaagagt ctttttggt ggaagaagac aagaagcatg aacgtcatcc tatttttgga      360
aatatagtag atgaagttgc ttatcatgag aaatatccaa ctatctatca tctgcgaaaa      420
aaattggtag attctactga taaagcggat ttgcgcttaa tctatttggc cttagcgcat      480
atgattaagt ttcgtggtca ttttttgatt gagggagatt taaatcctga taatagtgat      540
gtggacaaac tatttatcca gttggtacaa acctacaatc aattatttga agaaaaccct      600
attaacgcaa gtggagtaga tgctaaagcg attcttctg cacgattgag taaatcaaga      660
cgattagaaa atctcattgc tcagctcccc ggtgagaaga aaaatggctt atttgggaat      720
ctcattgctt tgtcattggg tttgaccct aattttaaat caaattttga tttggcagaa      780
gatgctaaat tacagctttc aaaagatact tacgatgatg atttagataa tttattggcg      840
caaattggag atcaatatgc tgatttgttt ttggcagcta agaattatc agatgctatt      900 ttactttcag atatcctaag agtaaatact gaaataacta aggctcccct atcagcttca      960
atgattaaac gctacgatga acatcatcaa gacttgactc ttttaaaagc tttagttcga     1020
caacaacttc cagaaaagta taagaaaatc ttttttgatc aatcaaaaaa cggatatgca     1080
ggttatattg atggggagc tagccaagaa gaattttata aatttatcaa accaattta      1140 gaaaaaatgg atggtactga ggaattattg gtgaaactaa atcgtgaaga tttgctgcgc     1200
aagcaacgga ccttttgacaa cggctctatt ccccatcaaa ttcacttggg tgagctgcat     1260 gctatttga gaagacaaga agactttat ccattttaa aagacaatcg tgagaagatt     1320
gaaaaaatct tgacttttcg aattccttat tatgttggtc cattggcgcg tggcaatagt     1380
cgttttgcat ggatgactcg gaagtctgaa gaaacaatta ccccatggaa ttttgaagaa     1440
gttgtcgata aggtgcttc agctcaatca tttattgaac gcatgacaaa ctttgataaa     1500
aatcttccaa atgaaaaagt actaccaaaa catagtttgc tttatgagta ttttacggtt     1560
tataacgaat tgacaaaggt caaatatgtt actgaaggaa tgcgaaaacc agcatttctt     1620
tcaggtgaac agaagaaagc cattgttgat ttactcttca aaacaaatcg aaaagtaacc     1680
gttaagcaat aaagaaga ttatttcaaa aaaatagaat gttttgatag tgttgaaatt     1740
tcaggagttg aagatagatt taatgcttca ttaggtacct accatgattt gctaaaaatt     1800
attaaagata aagattttt ggataatgaa gaaaatgaag atatcttaga ggatattgtt     1860
ttaacattga ccttatttga agataggag atgattgagg aaagacttaa aacatatgct     1920
cacctctttg atgataaggt gatgaaacag cttaaacgtc gccgttatac tggttgggga     1980
cgtttgtctc gaaaattgat taatggtatt agggataagc aatctggcaa aacaatatta     2040 gatttttga aatcagatgg ttttgccaat cgcaattta tgcagctgat ccatgatgat     2100
agtttgacat ttaaagaaga cattcaaaaa gcacaagtgt ctggacaagg cgatagttta     2160
catgaacata ttgcaaattt agctggtagc cctgctatta aaaaggtat tttacagact     2220 gtaaaagttg ttgatgaatt ggtcaaagta atggggcggc ataagccaga aaatatcgtt     2280
attgaaatgg cacgtgaaaa tcagacaact caaaagggcc agaaaaattc gcgagagcgt     2340
atgaaacgaa tcgaagaagg tatcaaagaa ttaggaagtc agattcttaa agagcatcct     2400
gttgaaaata ctcaattgca aaatgaaaag ctctatctct attatctcca aaatggaaga     2460
gacatgtatg tggaccaaga attagatatt aatcgtttaa gtgattatga tgtcgatcac     2520
```

```
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata agtacgtga gattaacaat     2940 taccatcatg cccatgatgc gtatctaaat gccgtcgttg gaactgcttt gattaagaaa    3000
tatccaaaac ttgaatcgga gtttgtctat ggtgattata agtttatga tgttcgtaaa     3060 atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatggaa agaagttcct ttgaaaaaaa tccgattgac    3540
tttttagaag ctaaaggata taaggaagtt aaaaaagact taatcattaa actacctaaa    3600
tatagtcttt ttgagttaga aaacggtcgt aaacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta acgatatac gtctacaaaa     4020 gaagttttag atgccactct tatccatcaa tccatcactg gtctttatga acacgcatt     4080 gatttgagtc agctaggagg tgactga                                         4107
```

<210> SEQ ID NO 11
<211> LENGTH: 461
<212> TYPE: DNA
<213> ORGANISM: Unknown
<220> FEATURE:
<223> OTHER INFORMATION: encoding tracrRNA

<400> SEQUENCE: 11

```
aaaaagttta aattaaatcc ataatgattt gatgatttca ataatagttt taatgaccct    60
cgaaattagt ttaatatgct ttaattttc tttttcaaaa tatctcttca aaaaatatta    120
cccaatactt aataataaat agattataac acaaaattct tttaaaaagt agtttatttt    180
gttatcattc tatagtatta agtattgttt tatggctgat aaatttcttt gaatttctcc    240
ttgattattt gttataaaag ttataaaata atcttgttgg aaccattcaa acagcatag    300 caagttaaaa taaggctagt ccgttatcaa cttgaaaaag tggcaccgag tcggtgcttt    360
```

```
ttttgatact tctattctac tctgactgca aaccaaaaaa acaagcgctt tcaaaacgct        420
tgttttatca tttttaggga aattaatctc ttaatcctttt t                          461

<210> SEQ ID NO 12
<211> LENGTH: 458
<212> TYPE: DNA
<213> ORGANISM: Artificial Sequence
<220> FEATURE:
<223> OTHER INFORMATION: encoding Spacers1_2_3_4

<400> SEQUENCE: 12
tatttcttaa taactaaaaa tatggtataa tactcttaat aaatgcagta atacaggggc        60
ttttcaagac tgaagtctag ctgagacaaa tagtgcgatt acgaaatttt ttagacaaaa       120
atagtctacg aggttttaga gctatgctgt tttgaatggt cccaaaaccg cggcttagct       180
acggctgagc acgcccctgt tttagagcta tgctgttttg aatggtccca aaacgtggga       240
ataaggggtg aggctggcat gcctgtttta gagctatgct gttttgaatg gtcccaaaac       300
cgcgaacaaa aatacgcgcc aggtgaaaat gttttagagc tatgctgttt tgaatggtcc       360
caaaacccac tttgccccac aatttcccac tgaccggttt tagagctatg ctgttttgaa       420
tggtcccaaa acttcagcac actgagactt gttgagtt                               458

<210> SEQ ID NO 13
<211> LENGTH: 18
<212> TYPE: DNA
<213> ORGANISM: Unknown
<220> FEATURE:
<223> OTHER INFORMATION: restriction enzyme I-SceI

<400> SEQUENCE: 13
tagggataac agggtaat                                                     18
```